(12) United States Patent
Boudreaux

(10) Patent No.: US 10,966,781 B2
(45) Date of Patent: *Apr. 6, 2021

(54) ELECTROSURGICAL SHEARS WITH KNIFE LOCK AND CLAMP-ACTUATED SWITCH

(71) Applicant: ETHICON LLC, Guaynabo, PR (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 371 days.

This patent is subject to a terminal disclaimer.

(21) Appl. No.: 15/989,430

(22) Filed: May 25, 2018

(65) Prior Publication Data
US 2019/0357969 A1    Nov. 28, 2019

(51) Int. Cl.
| *A61B 18/14* | (2006.01) |
| *A61B 90/00* | (2016.01) |
| *A61B 18/12* | (2006.01) |
| *A61B 17/00* | (2006.01) |
| *A61B 18/00* | (2006.01) |

(52) U.S. Cl.
CPC ...... *A61B 18/1445* (2013.01); *A61B 18/1206* (2013.01); *A61B 90/03* (2016.02); *A61B 2017/00407* (2013.01); *A61B 2018/0063* (2013.01); *A61B 2018/00601* (2013.01); *A61B 2018/126* (2013.01)

(58) Field of Classification Search
CPC ............ A61B 18/1206; A61B 18/1442; A61B 18/1445; A61B 2018/00589; A61B 2018/00601; A61B 2018/00619; A61B 2018/0063; A61B 2018/126; A61B 2018/1455; A61B 2017/00407; A61B 90/03
See application file for complete search history.

(56) References Cited

U.S. PATENT DOCUMENTS

| 6,500,176 B1 | 12/2002 | Truckai et al. |
| 7,112,201 B2 | 9/2006 | Truckai et al. |
| 7,125,409 B2 | 10/2006 | Truckai et al. |
| 7,169,146 B2 | 1/2007 | Truckai et al. |

(Continued)

OTHER PUBLICATIONS

U.S. Appl. No. 15/989,424, entitled "Method and Apparatus for Open Electrosurgical Shears," filed May 25, 2018.

(Continued)

*Primary Examiner* — Michael F Peffley
(74) *Attorney, Agent, or Firm* — Frost Brown Todd LLC

(57) ABSTRACT

A surgical instrument includes an end effector, a handle assembly, a knife drive assembly, an electrode activation assembly, and a lockout assembly. The end effector includes a first jaw, a second jaw, a knife, and an electrode assembly. The handle assembly includes a housing associated with the first jaw and an arm associated with the second jaw, where the arm is configured to pivot the second jaw between an open position and a closed position. The lockout assembly is may transition between a locked configuration and an unlocked configuration. The lockout assembly may prevent activation of the electrode and prevent actuation of the knife drive assembly while in the locked configuration. The lockout assembly may allow activation of the electrode and allow actuation of the knife drive assembly while in the unlocked configuration.

20 Claims, 45 Drawing Sheets

(56) References Cited

U.S. PATENT DOCUMENTS

| | | |
|---|---|---|
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,628,791 B2 * | 12/2009 | Garrison et al. ........ A61B 18/14 606/51 |
| 7,909,823 B2 * | 3/2011 | Moses et al. .......... A61B 18/14 606/51 |
| 7,922,718 B2 * | 4/2011 | Moses et al. .......... A61B 18/14 606/51 |
| 8,939,974 B2 | 1/2015 | Boudreaux et al. |
| 9,089,327 B2 | 7/2015 | Worrell et al. |
| 9,161,803 B2 | 10/2015 | Yates et al. |
| 9,402,682 B2 | 8/2016 | Worrell et al. |
| 9,545,253 B2 | 1/2017 | Worrell et al. |
| 9,610,114 B2 | 4/2017 | Baxter, III et al. |
| 9,877,720 B2 | 1/2018 | Worrell et al. |
| 2013/0296843 A1 | 11/2013 | Boudreaux et al. |
| 2014/0358142 A1 | 12/2014 | Miller et al. |
| 2016/0175030 A1 * | 6/2016 | Boudreaux ............ A61B 18/14 |
| 2016/0175031 A1 * | 6/2016 | Boudreaux ............ A61B 18/14 |
| 2017/0281211 A1 * | 10/2017 | Strobl et al. ........ A61B 17/3201 |

OTHER PUBLICATIONS

U.S. Appl. No. 15/989,433, entitled "Knife Drive Assembly for Electrosurgical Shears," filed May 25, 2018.

U.S. Appl. No. 15/989,438, entitled "Knife Auto-Return Assembly for Electrosurgical Shears," filed May 25, 2018.

U.S. Appl. No. 15/989,442, entitled "Compound Screw Knife Drive for Electrosurgical Shears," filed May 25, 2018.

U.S. Appl. No. 15/989,448, entitled "Firing and Lockout Assembly for Knife for Electosurgical Shears," filed May 25, 2018.

U.S. Appl. No. 15/989,452, entitled "Dual Stage Energy Activation for Electrosurgical Shears," filed May 25, 2018.

U.S. Appl. No. 15/989,455, entitled "Latching Clamp Arm for Electrosurgical Shears," filed May 25, 2018.

International Search Report and Written Opinion dated Nov. 20, 2019 for International Application No. PCT/IB2019/053692, 20 pages.

* cited by examiner

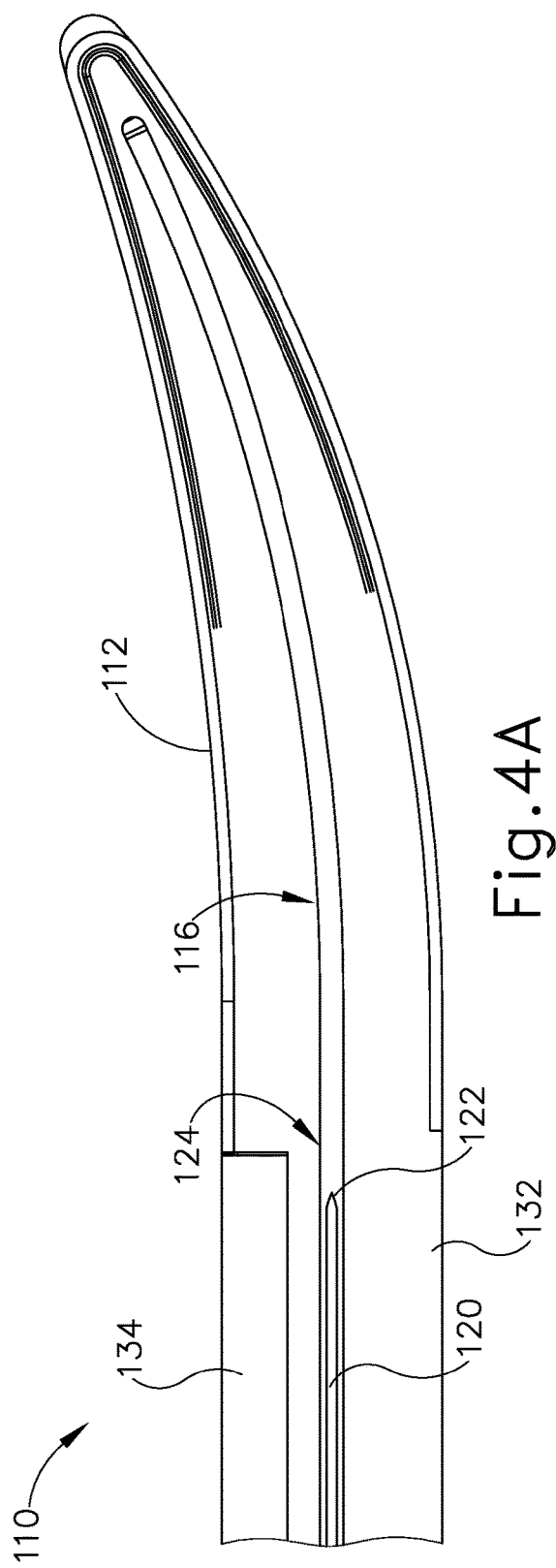
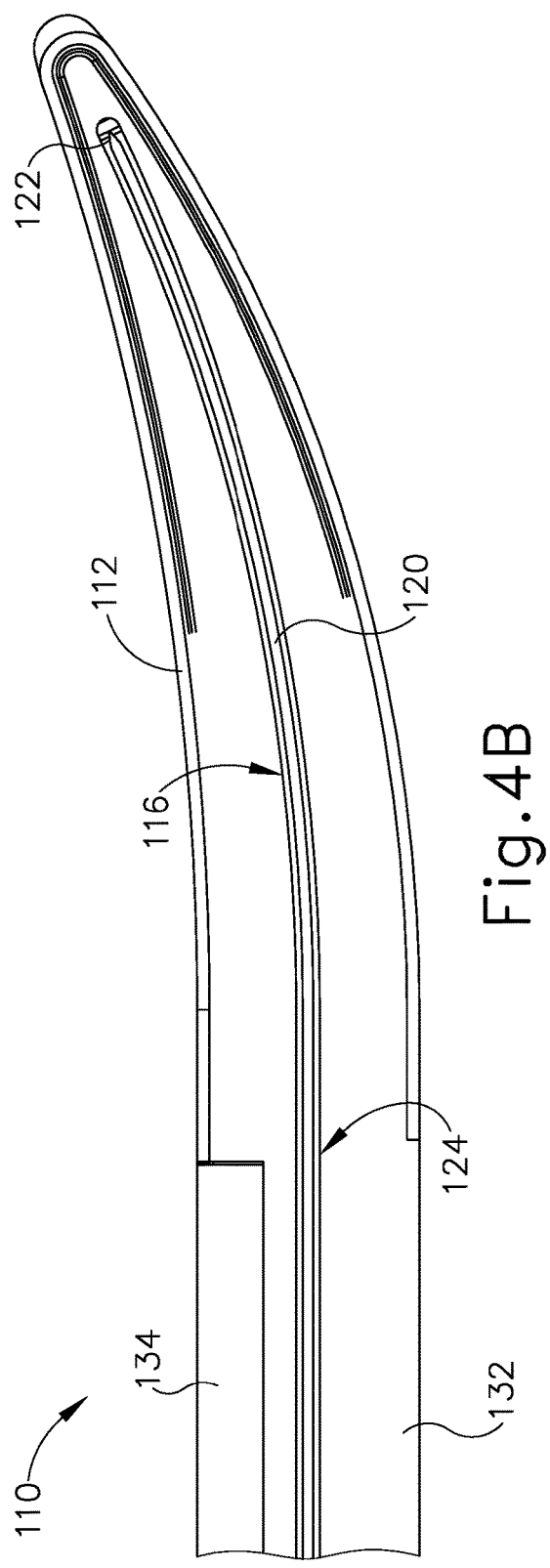
Fig.4A
Fig.4B

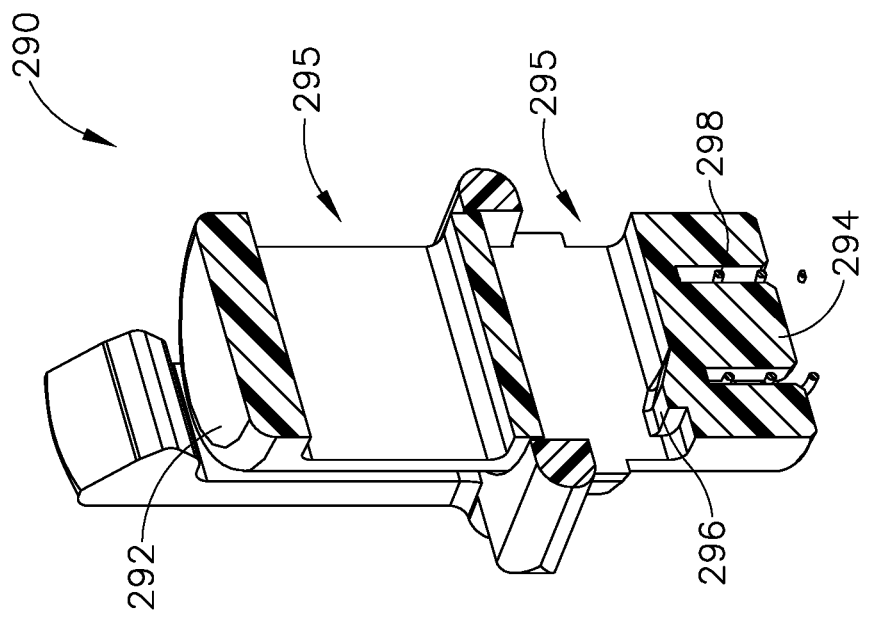
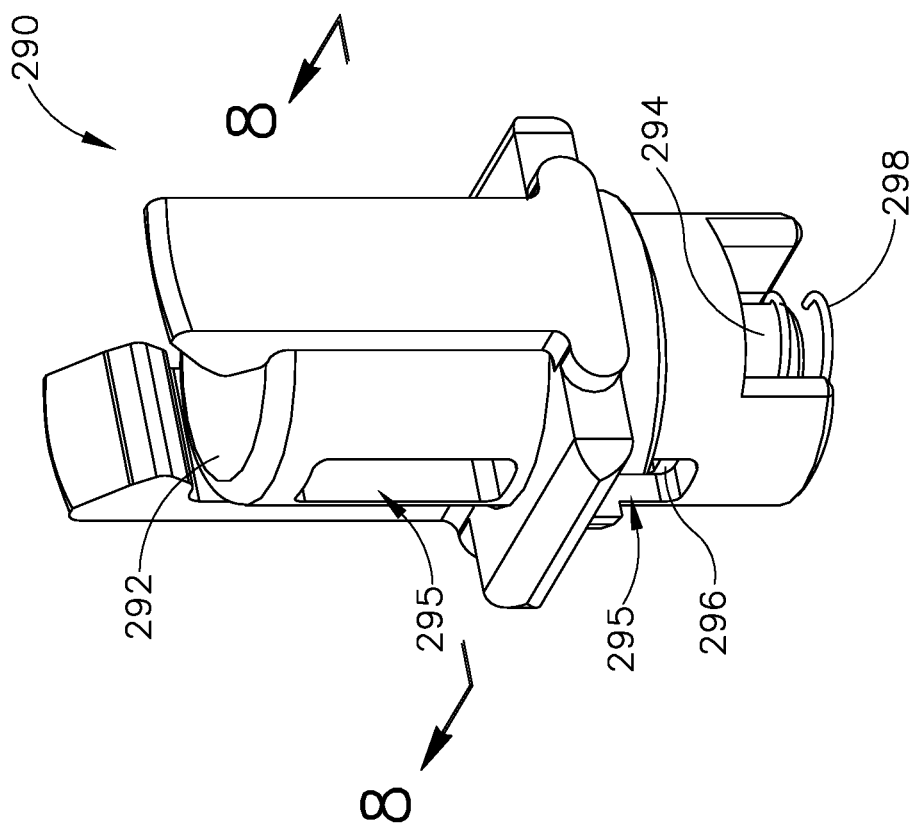

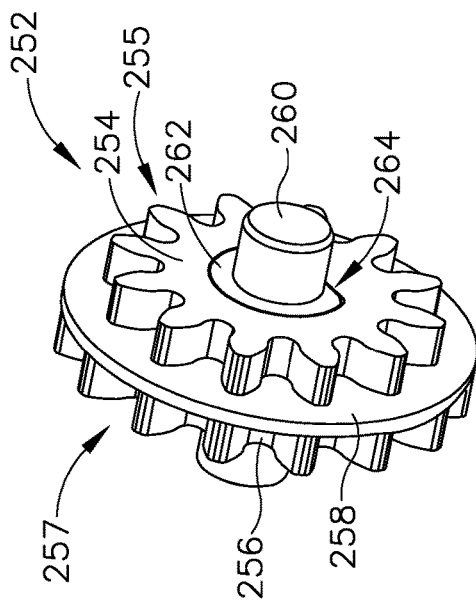
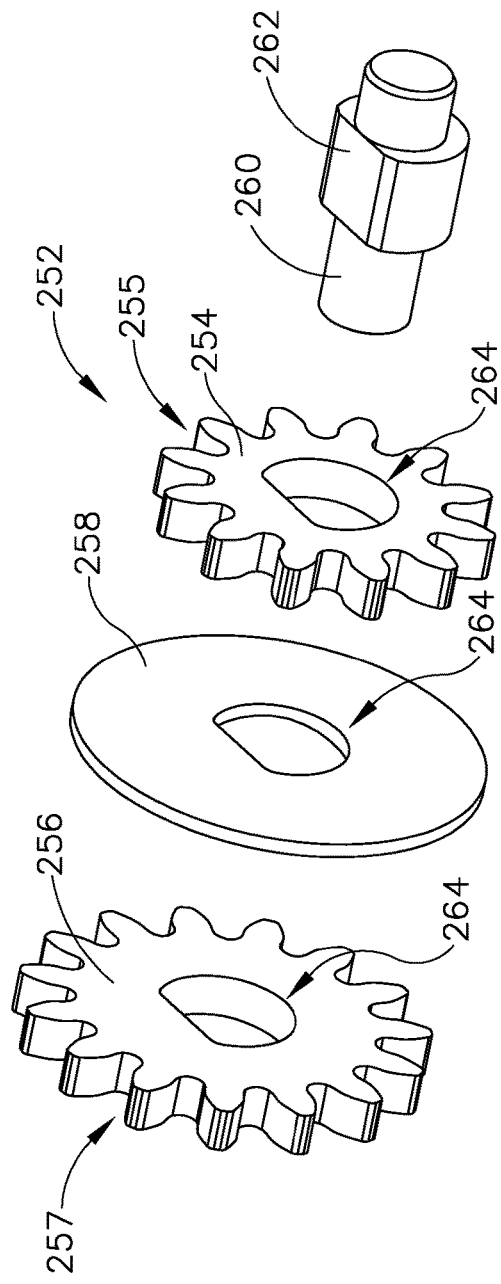

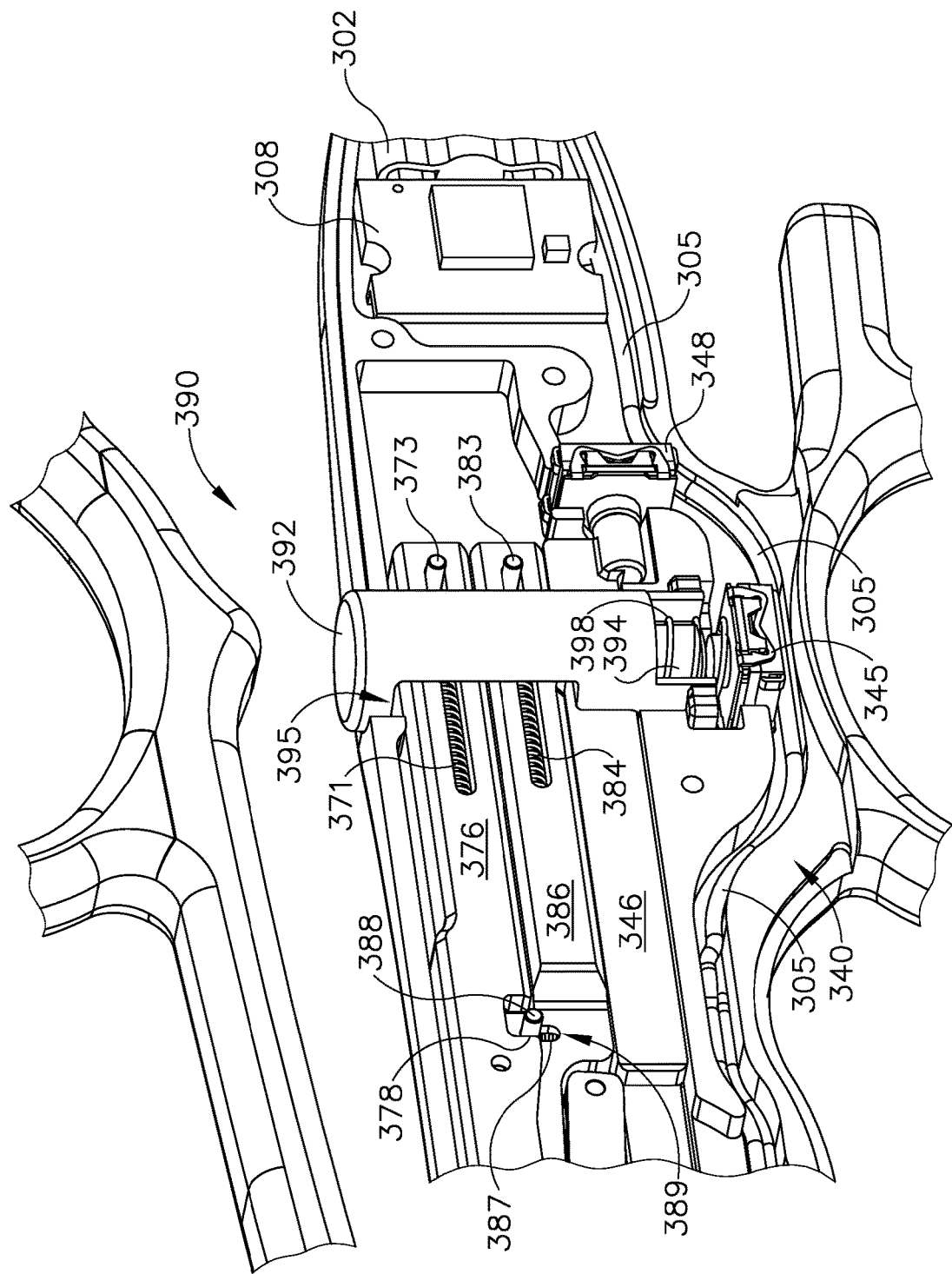

ELECTROSURGICAL SHEARS WITH KNIFE LOCK AND CLAMP-ACTUATED SWITCH

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

FIG. 7 depicts a perspective view of a lockout assembly of the electrosurgical forceps instrument of FIG. 5;

FIG. 8 depicts a cross-sectional view of the lockout assembly of FIG. 7, taken along line 8-8 of FIG. 7;

FIG. 12 depicts a perspective view of a rotary drive assembly of the firing assembly of FIG. 10;

FIG. 13 depicts an exploded perspective view of the rotary drive assembly of FIG. 12;

FIG. 21 depicts a perspective view of a portion of the forceps instrument of FIG. 17, with a portion of the handle assembly of FIG. 18 omitted for clarity, where the lockout assembly of FIG. 19 is in a locked configuration, where the resilient arm is in the relaxed position;

Figure 1:
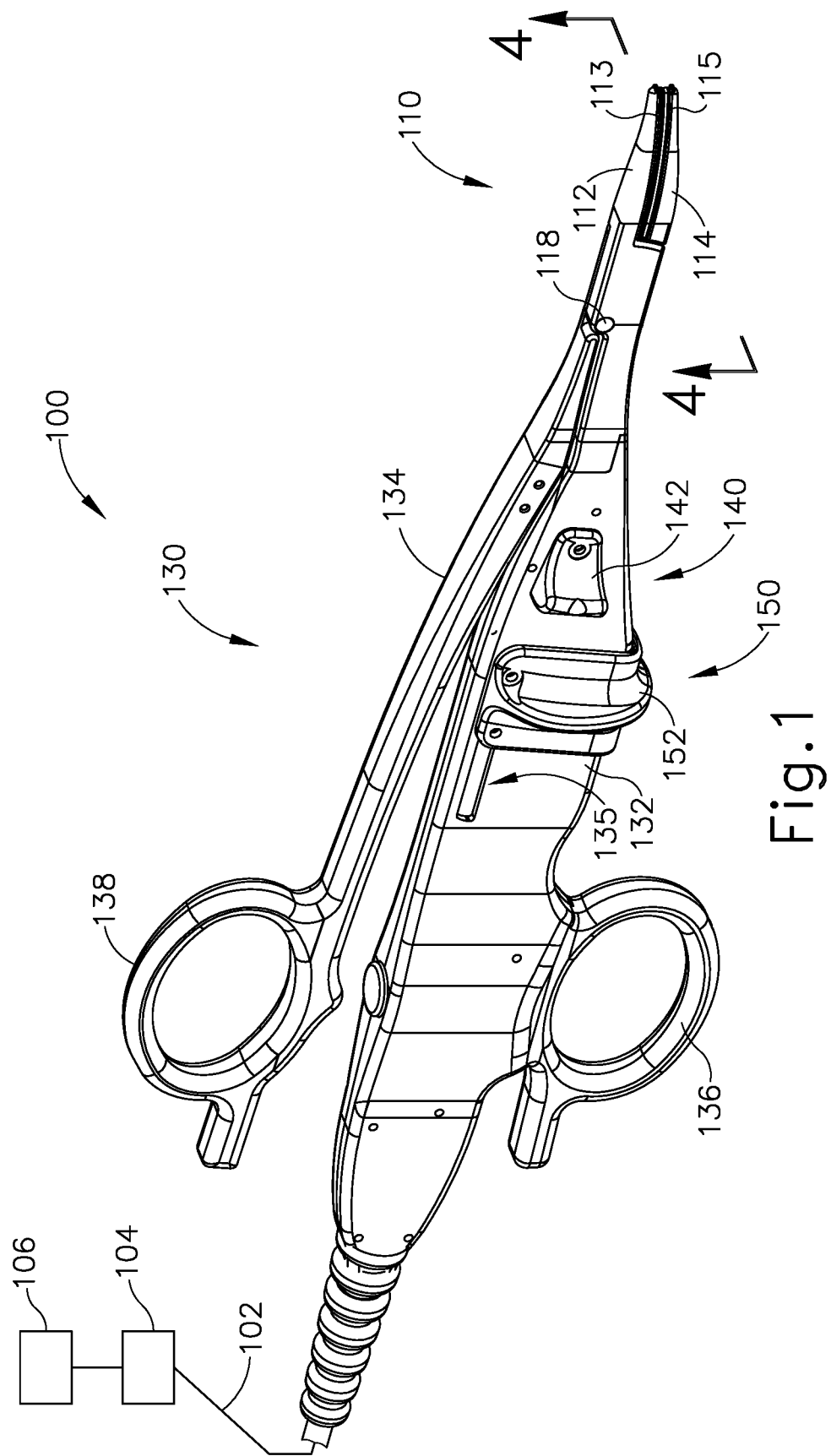
FIG. 1 depicts a perspective view of an exemplary electrosurgical forceps instrument, where an end effector is in a closed position, where a resilient arm is in a relaxed position.
Figure 2:
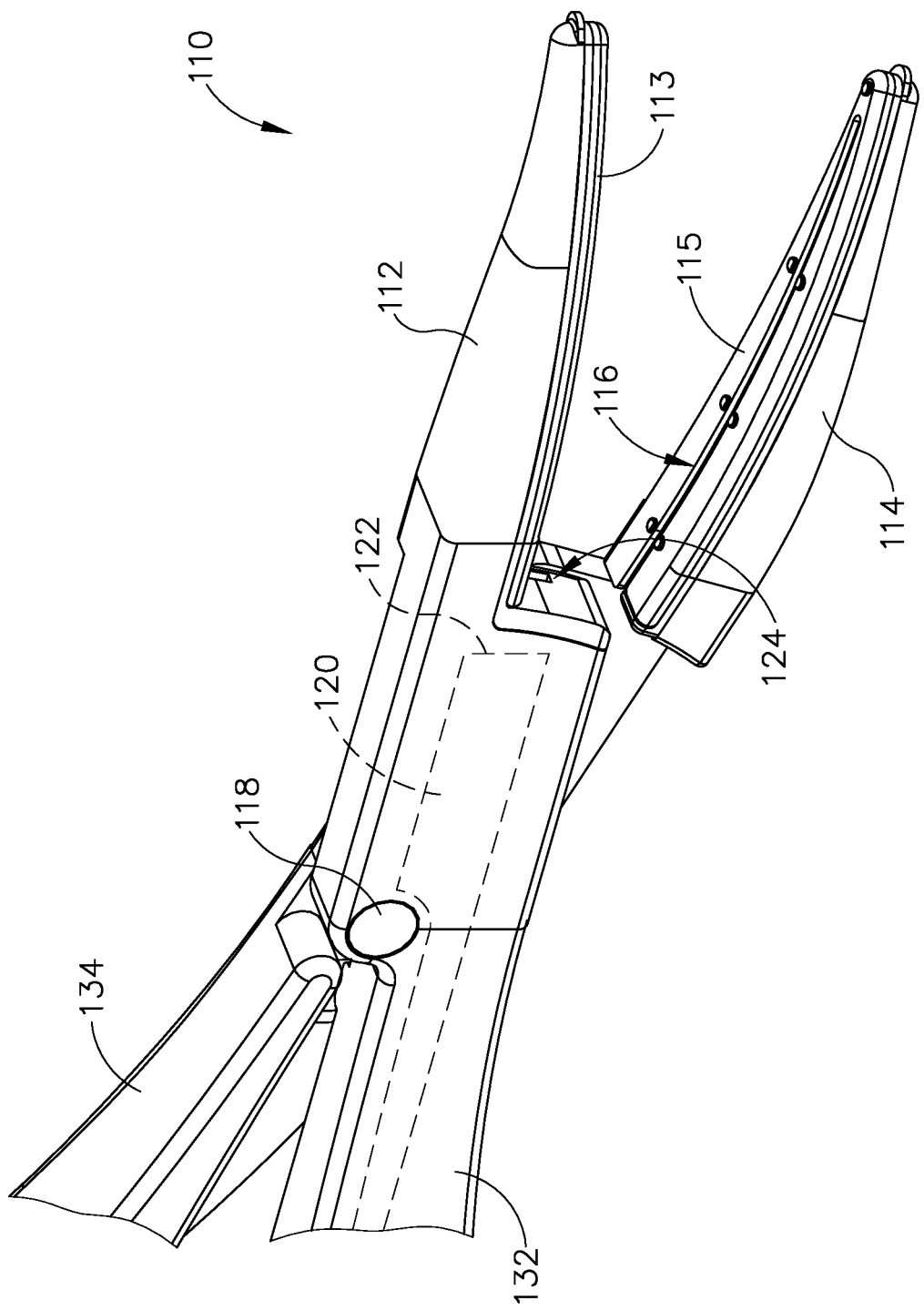
FIG. 2 depicts a perspective view of the end effector of FIG. 1 in an opened position, where a translating knife is in a proximal position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100).

Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112) and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134). Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternatively, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
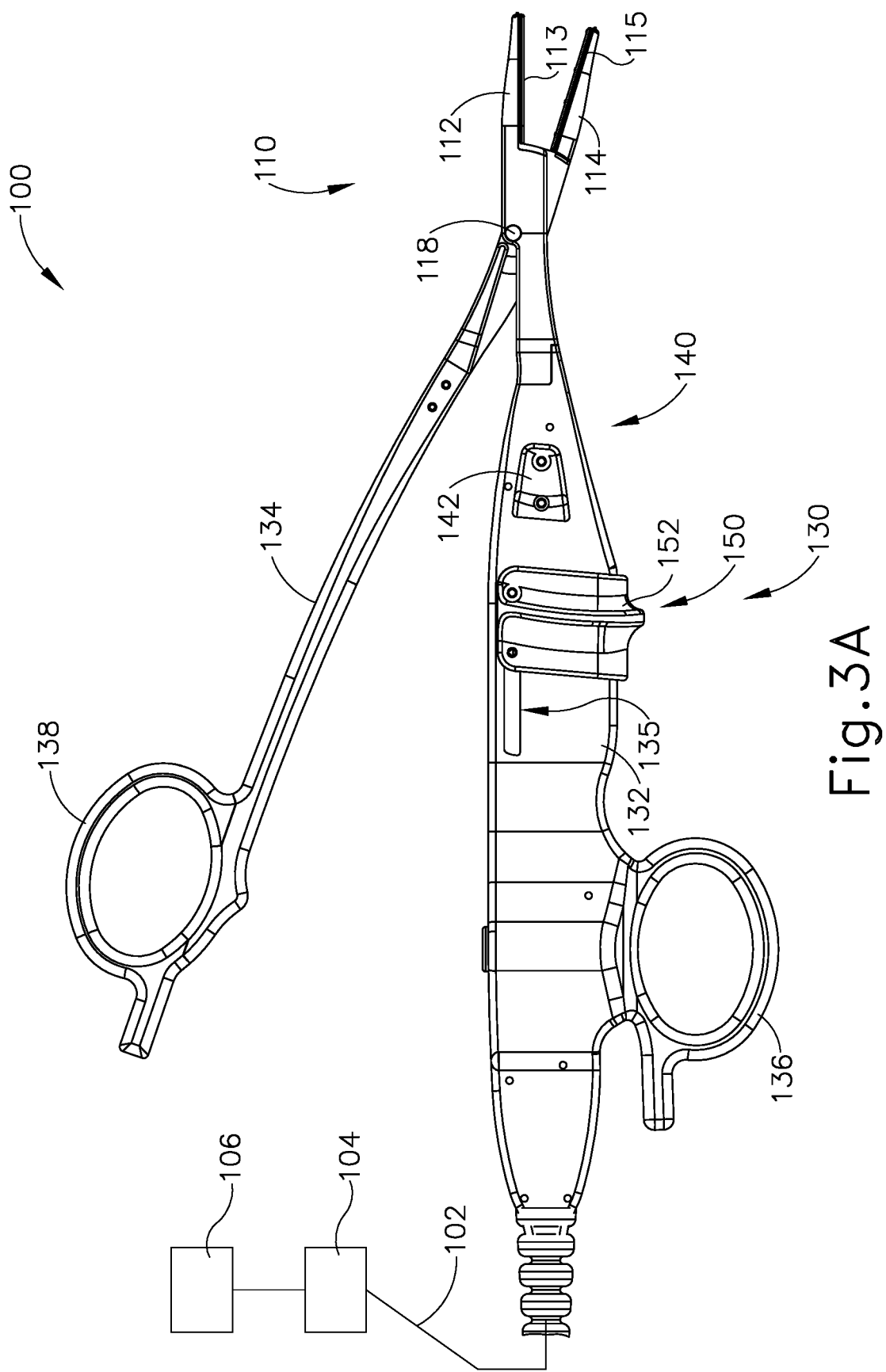
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.
Figure 3B:
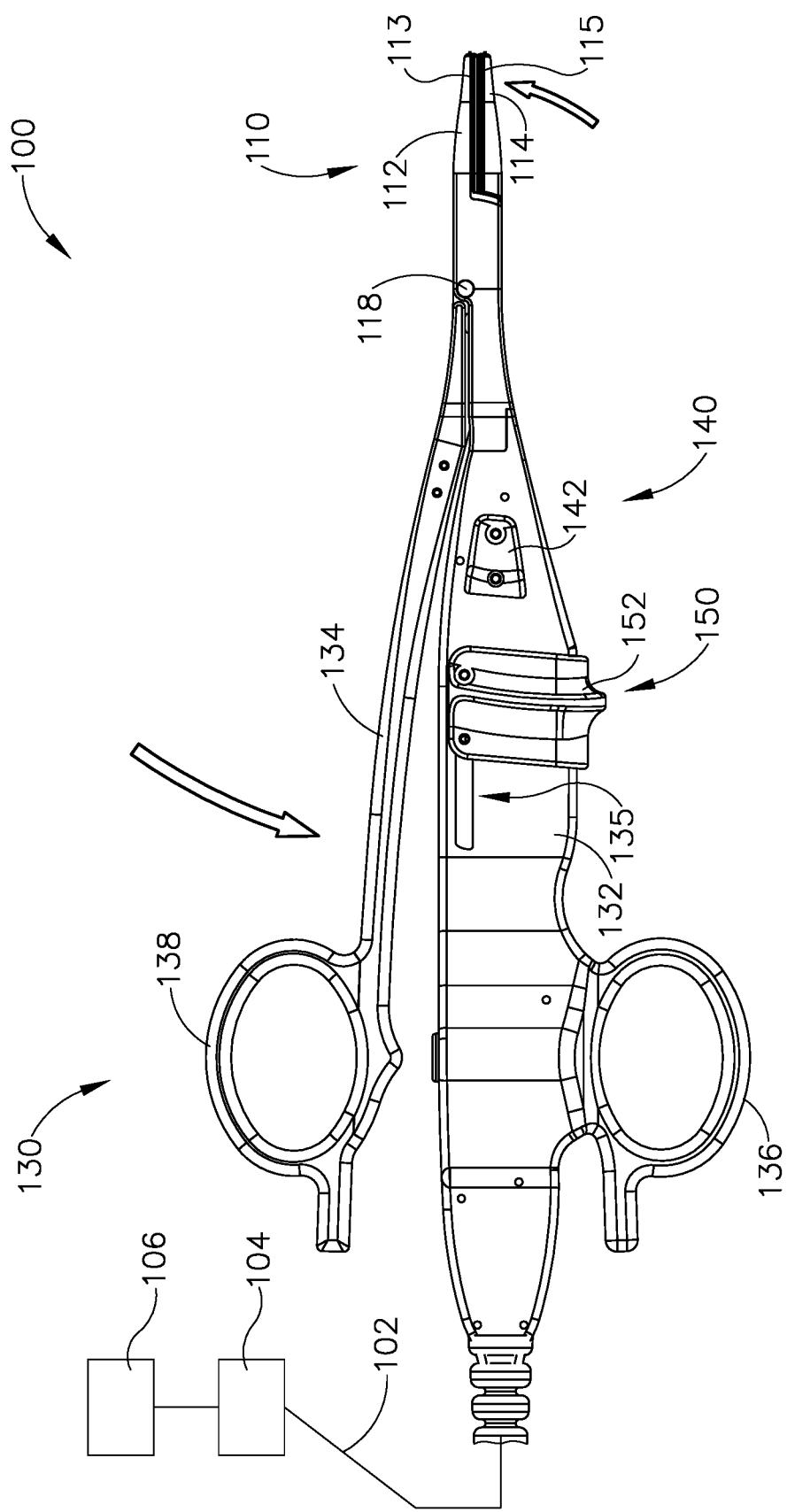
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3C:
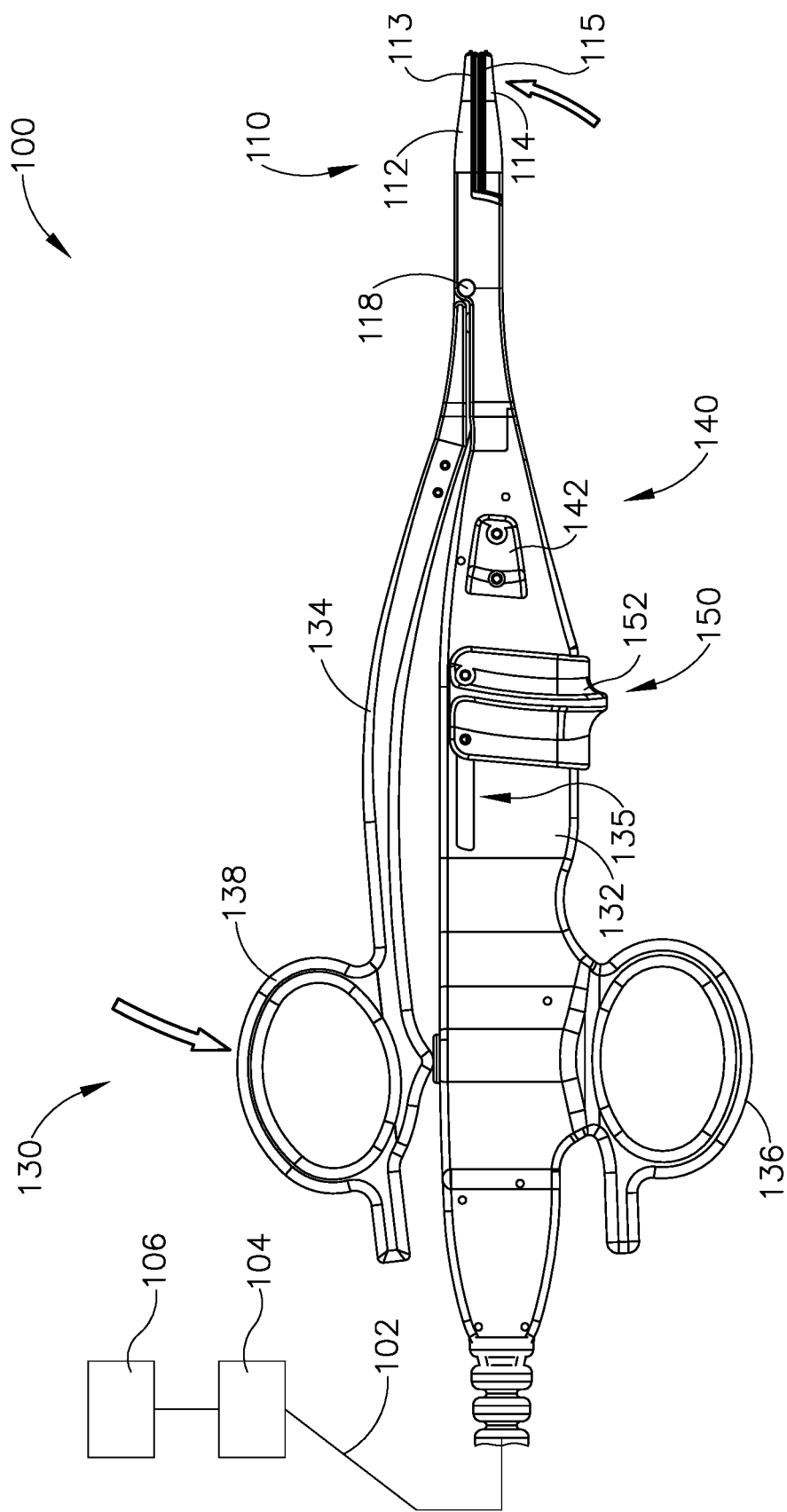
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
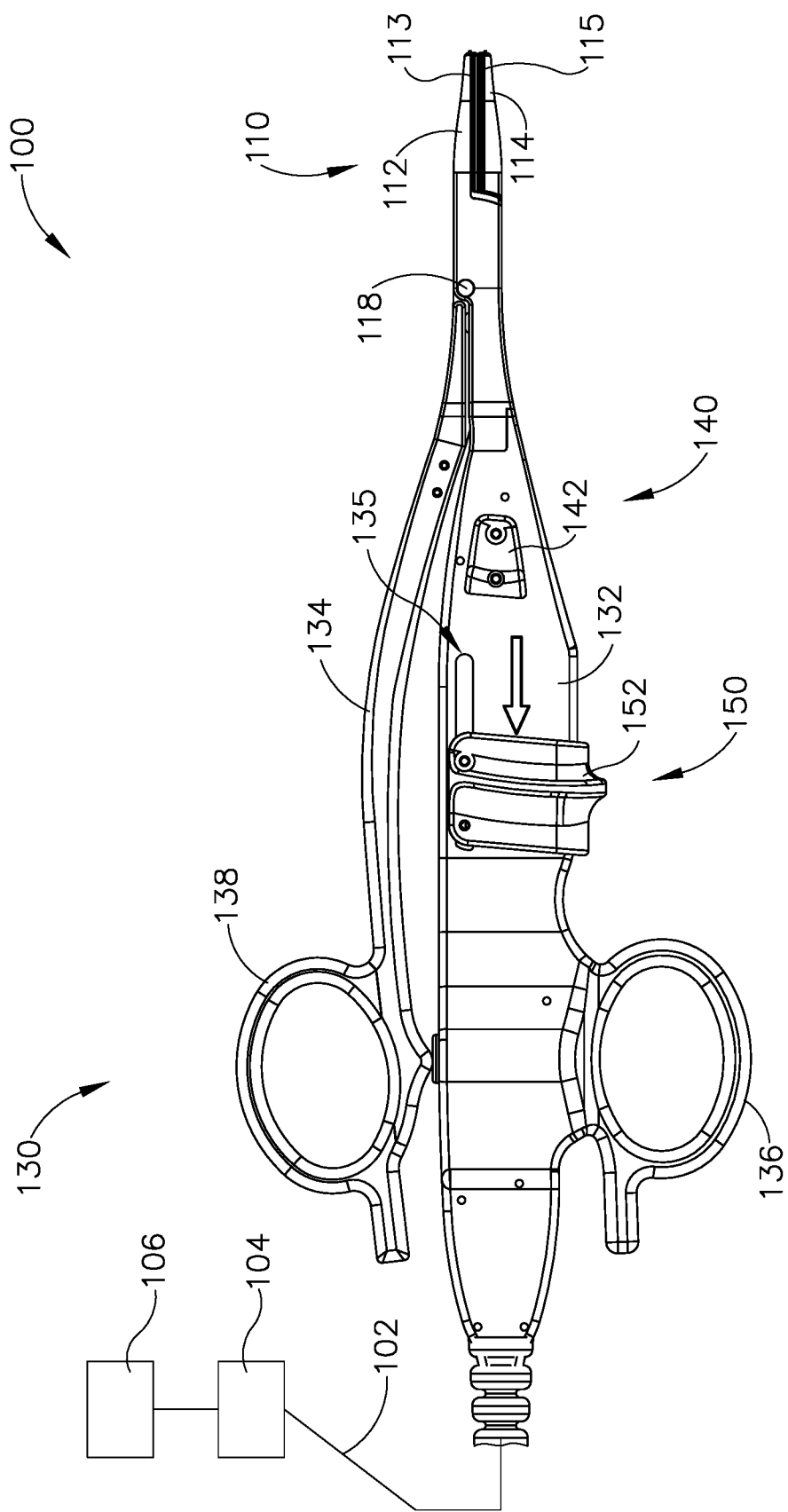
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captures between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Alternative Exemplary Electrosurgical Forceps

As mentioned above, it may be desirable to have a compact firing assembly with a trigger close to the center of the housing such that it is easy to actuate the firing assembly regardless of whether the instrument is flipped. Therefore, it may be desirable to have various firing assemblies that are configured to convert proximal translation of a sliding trigger into distal translation of a knife in order to sever tissue.

As also mentioned above, resilient arm (134) may flex toward housing (132) when jaws (112, 114) are in the closed position to provide greater closure forces between jaws (112, 114). The closure forces provided by flexing resilient arm (134) may help activated electrodes (113, 115) properly seal tissue grasped between jaws (112, 114). During exemplary use, if the operator fails to generate enough closure force while jaws (112, 114) are in the closed position, electrodes (113, 115) may fail to properly seal tissue grasped between jaws (112, 114). Therefore, it may be desirable to provide a lockout assembly that indicates when jaws (112, 114) provide a suitable closure force for sealing grasped tissue or prevents electrodes (113, 115) from activating unless jaws (112, 114) provide a suitable closure force for sealing grasped tissue.

In some instances, the operator may accidentally actuate knife trigger (152) proximally while jaws (112, 114) are open, inadvertently exposing distal cutting edge (122) of knife (120) within slot (116). Therefore, it may be desirable to provide a lockout mechanism that prevents actuation of knife until jaws (112, 114) are sufficiently closed. Alternatively, the operator may properly actuate knife (120) distally while jaws (112, 114) are suitably grasping tissue, and then prematurely open jaws (112, 114) such that distal cutting edge (122) is inadvertently exposed within slot (116). Inadvertent exposure of distal cutting edge (122) within slot (116) while jaws (112, 114) are open may cause accidental tissue damage. Therefore, it may be desirable to prevent exposure of distal cutting edge (122) after distally firing knife (120) through jaws (112, 114) by having an automatic knife return mechanism configured to automatically drive knife (120) to a pre-fired position after knife (120) reaches a predetermined distal position.

While various examples of firing assemblies, lockout assemblies, and knife return mechanisms are described below, it should be understood various combinations or modifications may be made to such firing assemblies, lockout assemblies, and knife return mechanism as would be apparent to one having ordinary skill in the art in view of the teachings herein.

Figure 5:
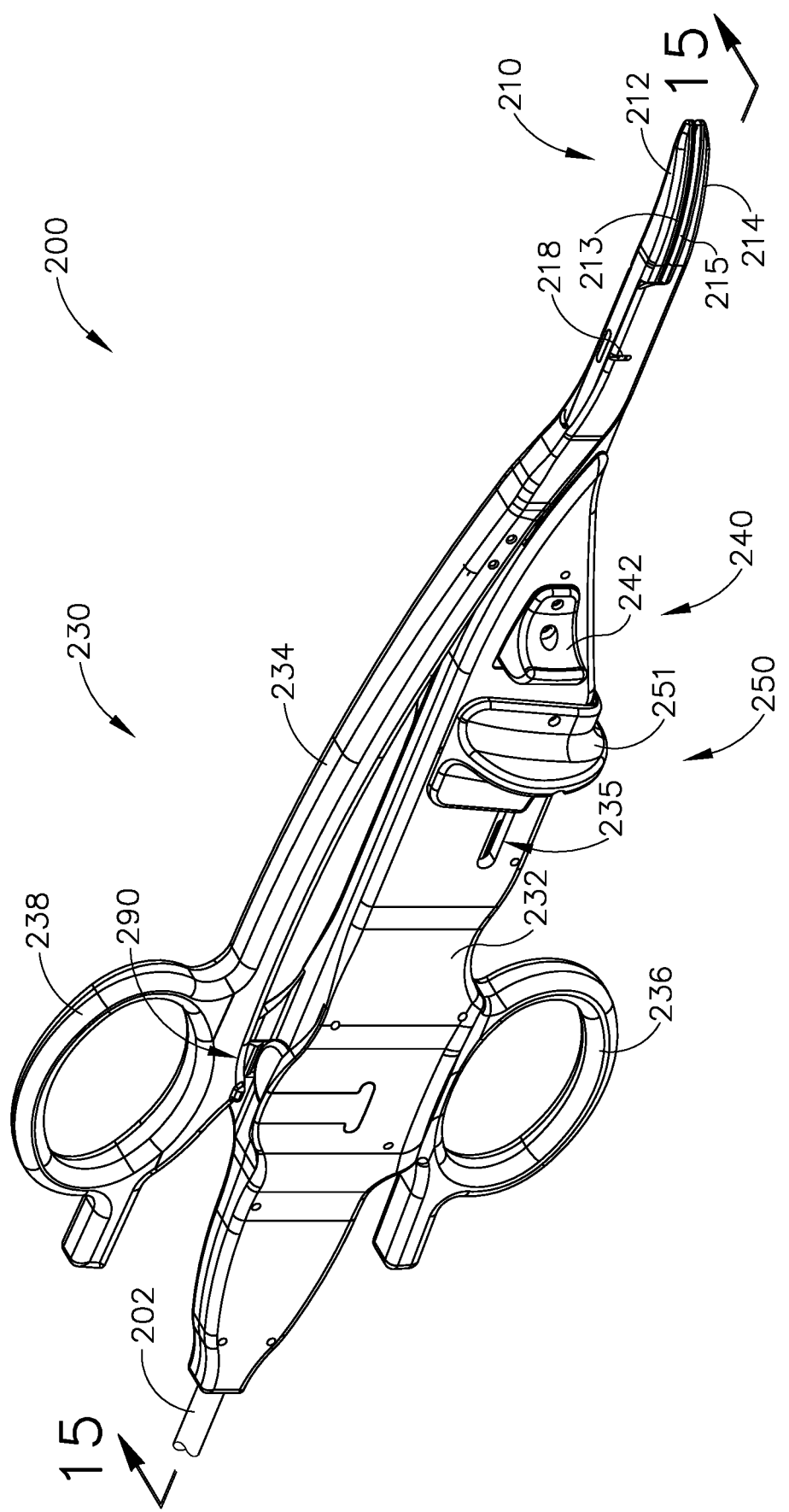
FIG. 5 depicts a perspective view of another exemplary electrosurgical forceps instrument, where an end effector is in a closed position, where a resilient arm is in a relaxed position.

A. Exemplary Instrument with Rack and Pinion Firing Assembly, Lockout Mechanism, and Knife Return Feature FIG. 5 shows an alternative exemplary electrosurgical forceps instrument (200) that may be used in replacement of instrument (100) described above. Therefore, as will be described in greater detail below, instrument (200) may be used to grasp, seal, and sever tissue.

Instrument (200) includes an end effector (210), a handle assembly (230), an electrode activation assembly (240), a firing assembly (250), and a lockout assembly (290). End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214).

Figure 6:
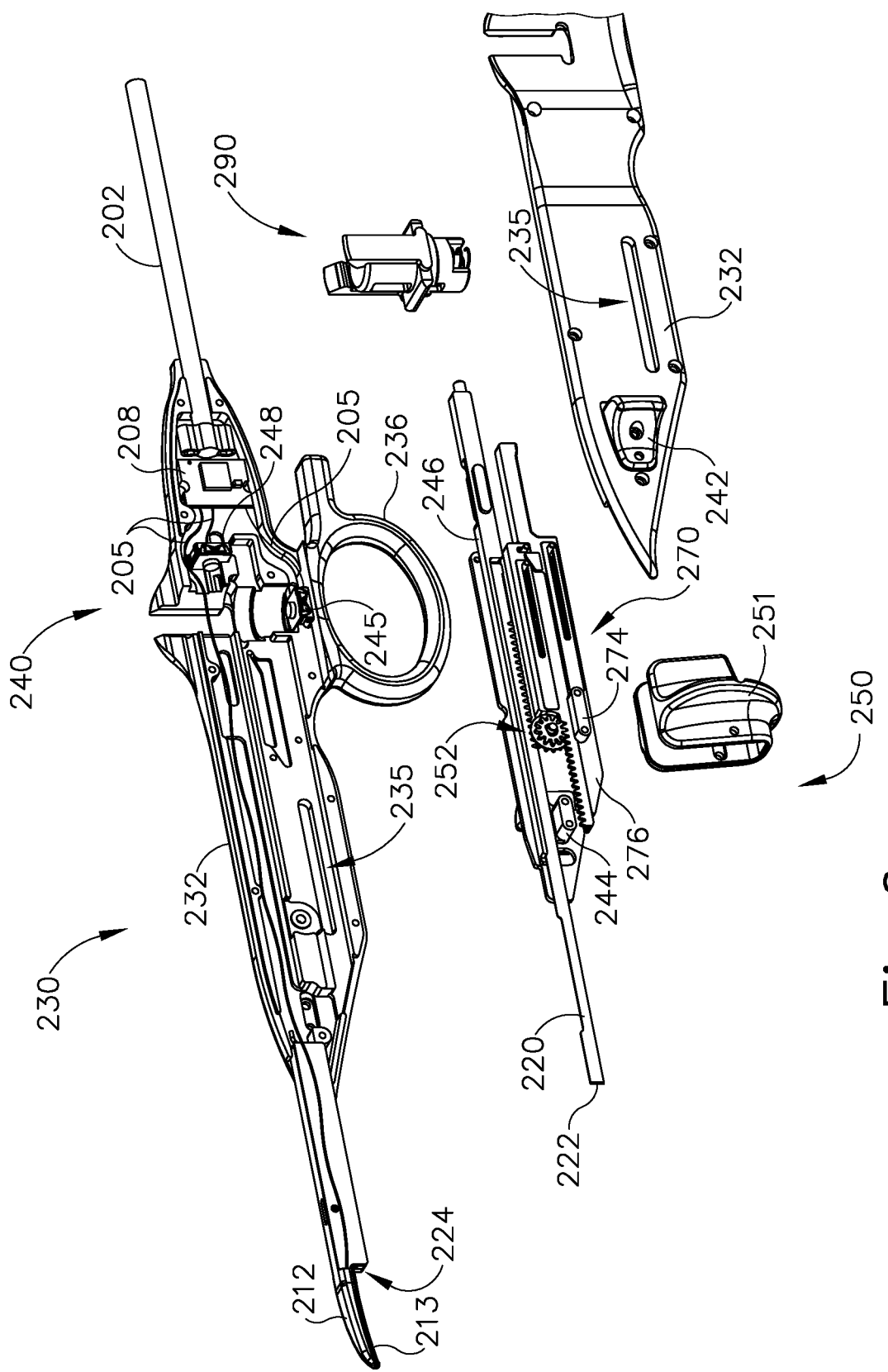
FIG. 6 depicts an exploded perspective view of a handle assembly of the electrosurgical forceps instrument of FIG. 5.
Figure 10:
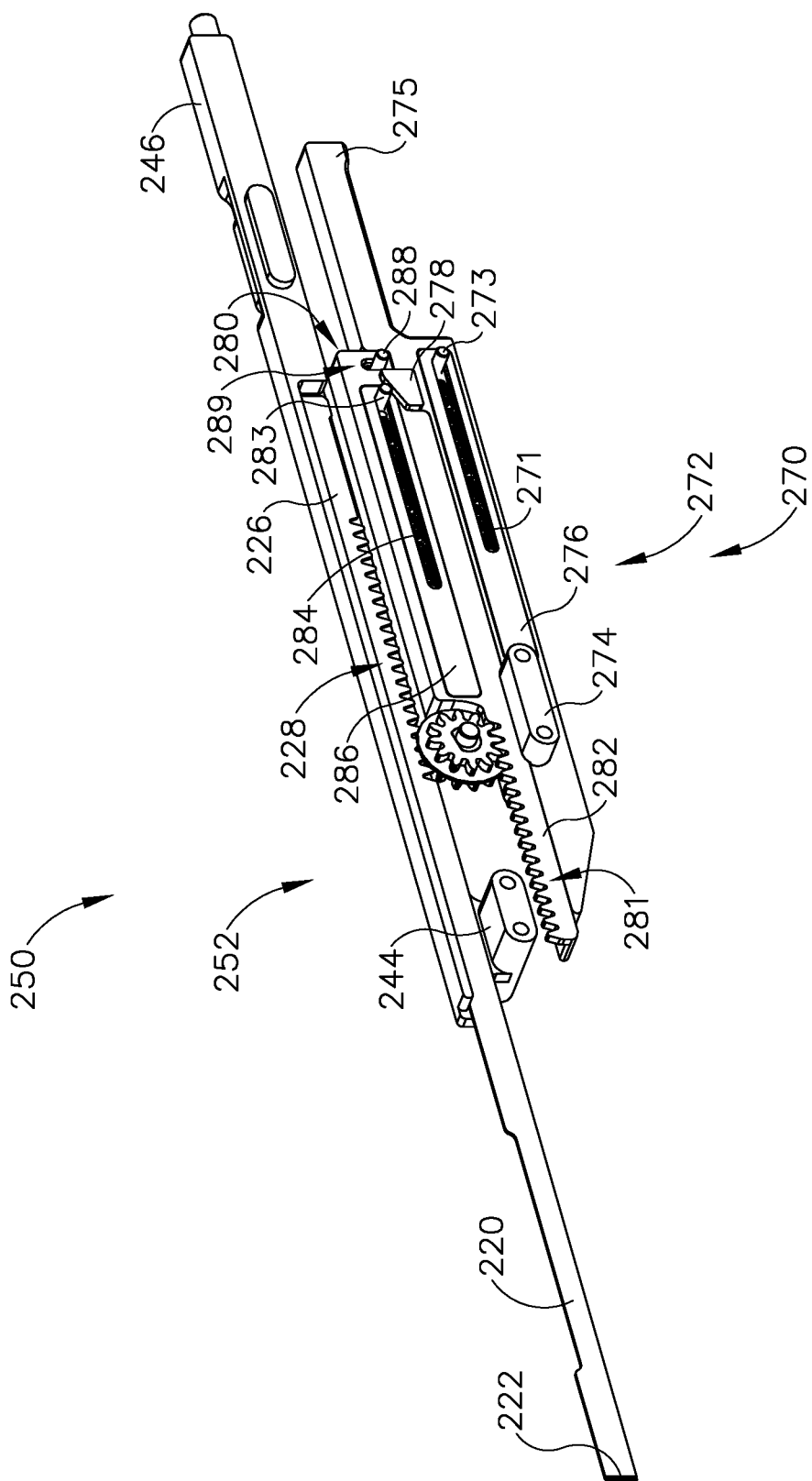
FIG. 10 depicts a perspective view of a firing assembly of the electrosurgical forceps instrument of FIG. 5.

First jaw (212) and second jaw (214) are pivotably coupled with each other via pivot pin (218). First jaw (212) and second jaw (214) may pivot between an open position (FIG. 14A) and a closed position (FIG. 14B) in order to grasp tissue. First and second electrodes (213, 215) are positioned on respective jaws (212, 214) such that electrodes (213, 215) face each other when jaws (212, 214) are pivoted into the closed position. Additionally, each electrode (213, 215) is U-shaped in the present example, with the bend of the U-shape located near the distal end of each respective jaw (212, 214), such that each electrode (213, 215) includes two longitudinally extending, laterally spaced-apart legs extending along the length of each respective jaw (212, 214). Laterally spaced-apart legs of each electrode (213, 215) and corresponding portions of jaws (212, 214) define an elongate slot (216). Elongate slot (216) is dimensioned to slidably receive knife (220) such that knife may translate from a proximal position to a distal position, similar to knife (120) described above. As best shown in FIGS. 6 and 10, knife (220) includes a distal cutting edge (222) configured to sever tissue captured between jaws (212, 214) in the closed position.

A cable (202) extends proximally from handle assembly (230). Similar to cable (102) of instrument (100), cable (202) is configured to couple with control unit (104), which is further coupled with a power source (106). Therefore, control unit (104) is operable to provide RF power to electrodes (213, 215) of jaws (212, 214), to thereby seal tissue suitably captured between jaws (212, 214).

Handle assembly (230) includes a housing (232) and a resilient arm (234). Housing (232) and resilient arm (234) are substantially similar to housing (122) and resilient arm (134) described above, with differences elaborated below. Housing (232) and resilient arm (234) are pivotably coupled with each other via pivot pin (218). Housing (232) extends distally into first jaw (212), while resilient arm (234) extends distally into second jaw (214). Housing defines a knife pathway (224) that slidably houses a portion of knife (220). Housing (232) includes a finger ring (236) while resilient arm (234) terminates proximally into a thumb ring (238). Therefore, the operator may grasp instrument (200) in a scissor grip fashion and pivot resilient arm (234) relative to housing (232) via rings (236, 238) in order to open and close jaws (212, 214).

Resilient arm (234) is sufficiently resilient such that arm (234) may flex from a relaxed position (FIG. 14B) to a flexed position (FIG. 14C) in response to pivoting arm (234) further toward housing (232) when jaws (212, 214) are already in the closed position. Resilient arm (234) is biased toward the relaxed position. Further pivoting of resilient arm (234) into the flexed position may result in greater closure forces between jaws (212, 214) as compared to pivoting jaws (212, 214) into the closed position while arm (234) is in the relaxed position. Resilient arm (234) may be suitably resilient such that when resilient arm (234) is pivoted into the flexed position, the closure force between jaws (212, 214) is sufficient such that electrodes (213, 215) may properly seal tissue grasped between jaws (212, 214). Additionally, the resilient nature of arm (234) may limit the amount of closure force between jaws (212, 214) such that jaws (212, 214) may not compress tissue too much, resulting in inadvertent tissue damage. When the operator no longer desires to compress tissue between jaws (212, 214) to properly seal or sever clamped tissue, the operator may reduce the amount of closure force applied to resilient arm (234) such that arm (234) returns to the relaxed position.

Housing (232) contains electrode activation assembly (240), firing assembly (250), and lockout assembly (290). Firing assembly (250) of the current example include a knife trigger (251) slidably coupled with housing (232) via slot (235). As will be described in greater detail below, electrode activation assembly (240) is configured to selectively activate electrodes (213, 215); firing assembly (250) is configured to actuate knife (220) between the proximal position and the distal position (Similar to knife (120) as shown in FIGS. 4A-4B) in response to proximal translation of knife trigger (251) within slot (235); and lockout assembly (290) is configured to prevent actuation of knife (220) until specific conditions are satisfied. In some examples, lockout assembly (290) may be configured to prevent activation of electrodes (213, 215) until specific conditions are satisfied, or indicate when jaws (212, 214) are sufficiently closed for suitably sealing tissue. As will also be described in greater detail below, a portion of firing assembly (250) and handle assembly (230) form an automatic knife return mechanism configured to automatically drive knife (220) to the proximal, pre-fired, position after knife (220) reaches a predetermined distal position.

Electrode activation assembly (240) includes an RF trigger (242) slidably supported on each lateral side of housing (232), a sliding body (246) slidably contained within housing (232), a coupling block (244) fixed relative to sliding body (246), an activation button (248), and a lockout button (245). Coupling block (244) is configured to couple with each RF trigger (242) when instrument (200) is assembled. A proximal end of sliding body (246) is directly adjacent to activation button (248) such that proximal translation of sliding body (246) triggers activation button (248). Therefore, the operator may press RF trigger (242) proximally in order to compress activation button (248). RF trigger (242), coupling block (244), and/or sliding body (246) may be biased toward a position such that activation button (248) is not activated.

Activation button (248) and lockout button (245) are each contained within housing (232). Lockout button (245) and activation button (248) are each in communication with a circuit board (208) via electrical coupling wires (205); while circuit board (208) is also in communication with at least one electrode (213, 215) via electrical coupling wires (205). In the present example, circuit board (208) is contained within housing (232). Circuit board (208) is in communication with cable (202) such that circuit board (208) and control unit (104) are in electrical communication with each other. Therefore, circuit board (208) is configured to transfer RF energy from control unit (104) to electrodes (213, 215). As will be described in greater detail below, lockout assembly (290) is configured to depress lockout button (245) when jaws (212, 214) are sufficiently closed to provide sufficient closure force to properly seal tissue captured between electrodes (213, 215) using RF energy.

In the present example, activation button (248) and lockout button (245) are configured to instruct circuit board (208) to transfer RF energy from control unit (104) to electrodes (213, 215) when buttons (245, 248) are depressed. If only one, or neither, button (245, 248) is depressed, circuit board (208) will not transfer RF energy to electrodes (213, 215), thereby leaving electrodes (213, 215) deactivated. Therefore, for example, if the operator pressed RF trigger (242) without having lockout button (245) depressed, electrodes (213, 215) will remain deactivated. Alternatively, lockout button (245) may act as a switch for activation button (248) such that activation of lockout button (245) completes a circuit between at least one electrode (213, 215) and activation button (248).

In another example, lockout button (245) may only generate a signal to circuit board (208), which may then send the signal to control unit (104), that jaws (212, 214) are sufficiently closed to provide sufficient closure force to properly seal tissue captured between electrodes (213, 215) using RF energy. Control unit (104) may then signal to the operator (e.g., visually, audibly, and/or tactilely) that jaws (212, 214) are sufficiently closed. In such examples, activation button (248) may independently instruct circuit board (208) to transfer RF energy from control unit (104) to electrodes (213, 215) when activation button (248) is depressed.

In another example, depression of either activation button (248) or lockout button (245) may be configured to activate electrodes (213, 215), but activation of buttons (245, 248) may send a different signal to control unit (104), such that control unit produces a different signal (e.g., visually, audibly, and/or tactilely) indicating to a user which button (245, 248) has been depressed.

In yet another example, activation button (248) may be omitted entirely such that pressing lockout button (245) leads to activation of electrodes (213, 215).

While in the current example, circuit board (208) acts as an intermediary between control unit (104), electrodes (213, 215), and buttons (245, 248), this is merely optional, as buttons (245, 248) and electrodes (213, 215) may be in communication with cable (202) and control unit (104) without the use of circuit board (208).

As mentioned above, lockout assembly (290) is configured to either indicate when jaws (212, 214) are sufficiently closed or prevent activation of electrodes (213, 215) until jaws (212, 214) are sufficiently closed; while lockout assembly (290) is also configured to prevent actuation of knife (220) until specific conditions are satisfied. As best seen in FIGS. 7-8, lockout assembly (290) includes a translating body (292) defining through holes (295), and a bias spring (298). Translating body (292) includes a button (294) extending downwardly from the rest of body (292), and a lockout ledge (296). Translating body (292) is slidably disposed within housing (232). Translating body (292) is configured to actuate between a locked position (as shown in FIGS. 9 and 15A) to an unlocked position (as shown in FIGS. 15B-15C); while bias spring (298) abuts against an interior portion of housing (132) and translating body (292) to bias translating body (292) toward the locked position.

Figure 9:
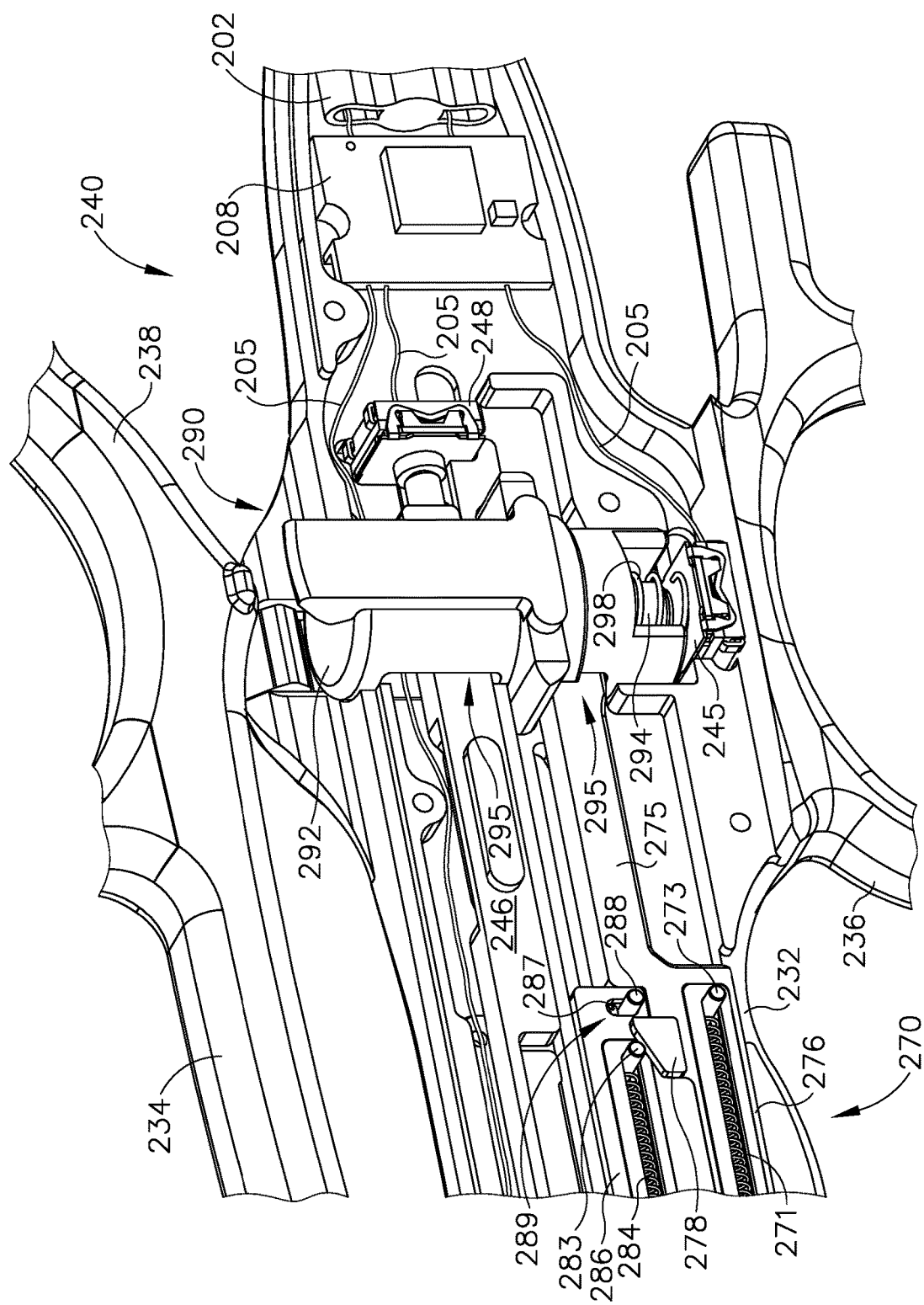
FIG. 9 depicts a perspective view of a portion of the forceps instrument of FIG. 5, with a portion of the handle assembly of FIG. 6 omitted for clarity, where the lockout assembly of FIG. 7 is in a locked configuration, where the resilient arm is in the relaxed position.
Figure 15A:
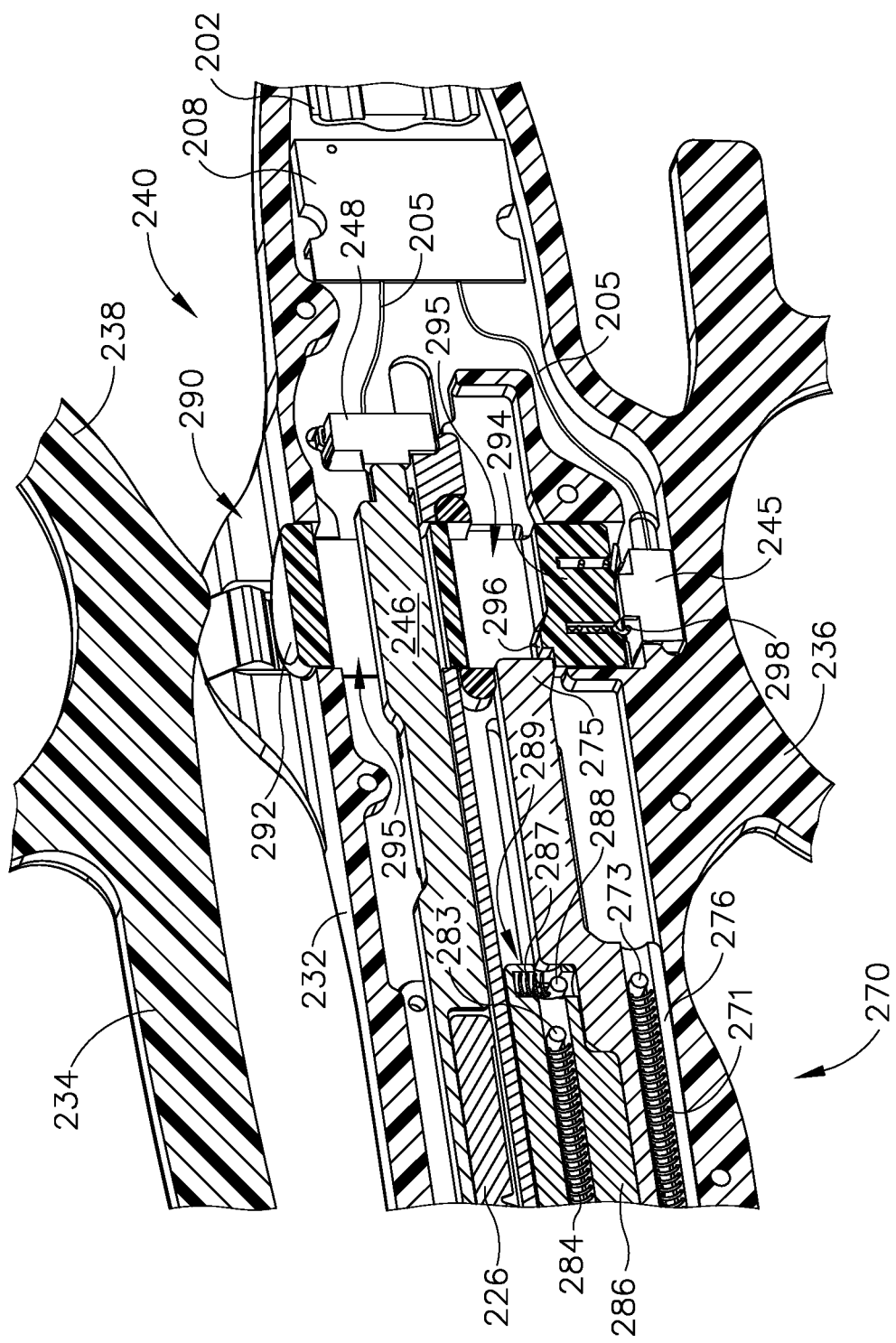
FIG. 15A depicts a cross-sectional view of a portion of the instrument of FIG. 5, taken along line 15-15 of FIG. 5, where the resilient arm is in a relaxed position, where the lockout assembly of FIG. 7 is in a locked position, and where the firing assembly of FIG. 10 is in a pre-fired position.
Figure 15B:
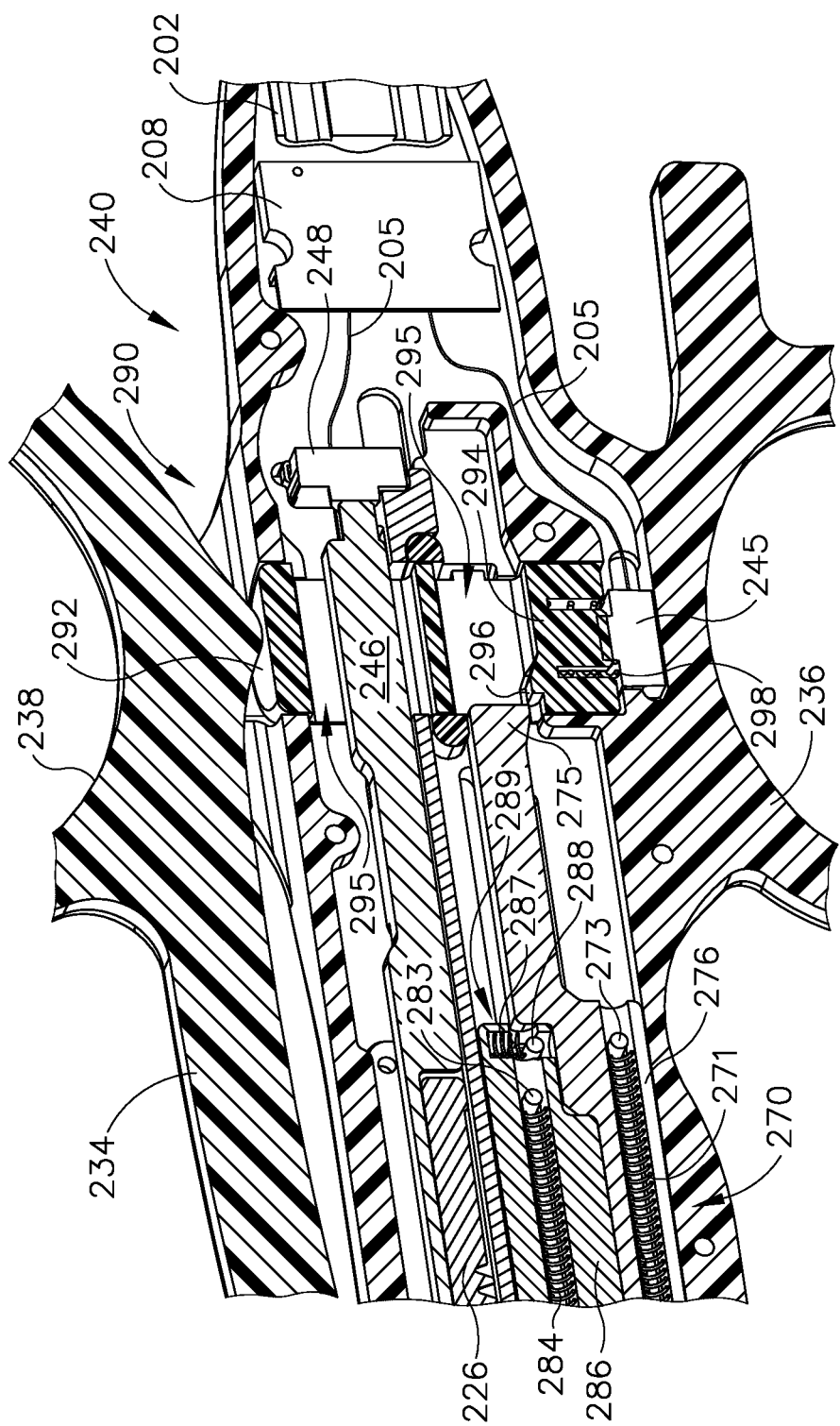
FIG. 15B depicts a cross-sectional view of a portion of the instrument of FIG. 5, taken along line 15-15 of FIG. 5, where the resilient arm is in a flexed position, where the lockout assembly of FIG. 7 is in an unlocked position, and where the firing assembly of FIG. 10 is in the pre-fired position.
Figure 15C:
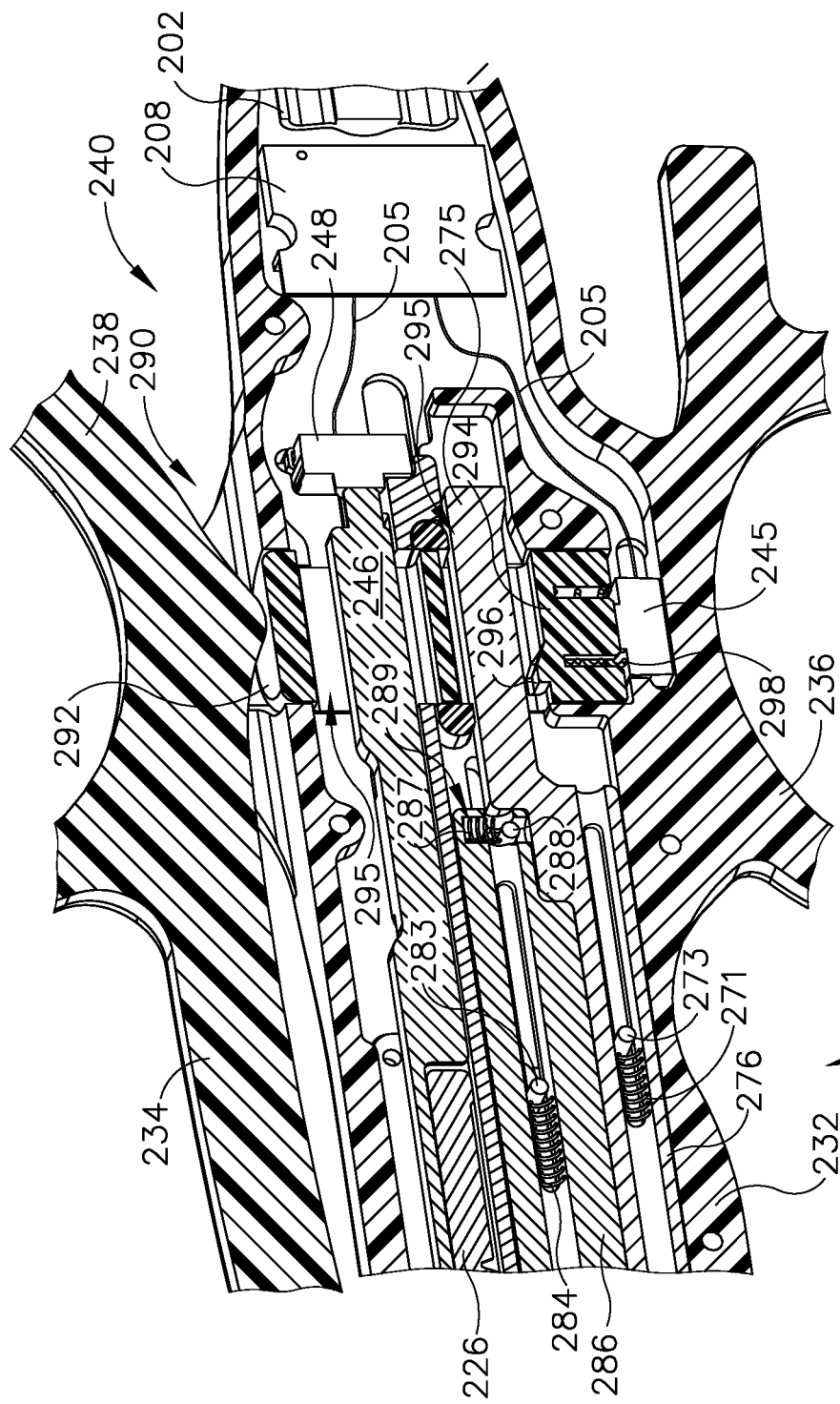
FIG. 15C depicts a cross-sectional view of a portion of the instrument of FIG. 5, taken along line 15-15 of FIG. 5, where the resilient arm is in the flexed position, where the lockout assembly of FIG. 7 is in the unlocked position, and where the firing assembly of FIG. 10 is in a fired position.

As best seen in FIGS. 9 and 15A, a portion of translating body (292) extends away from housing (232) toward thumb ring (238) while in the locked position. Thumb ring (238) of resilient arm (234) is dimensioned to abut against the portion of translating body (292) extending away from housing (232) when resilient arm (234) is in the flexed position, thereby driving lockout assembly (290) into the unlocked position. Thumb ring (238) does not abut against the portion of translating body (292) extending away from housing (232) when resilient arm (234) is in the relaxed position, such that spring (298) biases translating body (292) into the locked position.

As described above, the closure forces provided by jaws (212, 214) when resilient arm (234) is in the flexed position are suitable for electrodes (213, 215) to seal tissue via RF energy. Therefore, lockout assembly (290) is configured to move into the unlocked position when jaws (212, 214) provide a suitable closure force for electrodes (213, 215) to seal tissue via RF energy. Additionally, lockout assembly (290) is configured to move into the locked position when jaws (212, 214) do not provide a suitable closure force for electrodes (213, 215) to seal tissue via RF energy.

While in the unlocked position, button (294) depresses lockout button (245) of electrode activation assembly (240), thereby rendering lockout button (245) activated. Therefore, in the present example, if the operator presses RF trigger (242) while lockout assembly (290) is in the unlocked position, circuit board (208) would activate electrodes (213, 215) due to both buttons (248, 245) being depressed. In other words, the operator is permitted to activate RF energy to electrodes (213, 215) when the closure forces provided by jaws (212, 214) are suitably conducive for sealing tissue via RF energy. In another example, lockout button (245) generates a signal send to control unit (104). An in yet another example, depressing lockout button (245) instructs circuit board (208) to activate electrode (213, 215).

Also, while in the unlocked position, lockout ledge (296) is spaced away from a proximal surface (275) of firing assembly (250) such that firing assembly (250) may actuate knife (220) in accordance with the description herein. Therefore, when lockout assembly (290) is in the unlocked position, the operator may both activate electrodes (213, 215) with RF energy, and actuate knife (220) distally to sever tissue grasped between jaws (212, 214). Lockout assembly (290) may indicate to the operator when lockout assembly (290) is in the unlocked configuration. For example, depressing button (245) may activate a suitable indicator as would be apparent to one having ordinary skill in the art in view of the teachings herein. For example, an LED may turn on, an instrument may emit noise, or a tactile response may be felt.

While in the locked position, button (294) is spaced away from lockout button (245) of electrode activation assembly (240), thereby rendering lockout button (245) un-activated. Therefore, in some versions where both lockout button (245) and activation button (238) must be depressed to activate electrodes (213, 215), if the operator presses RF trigger (242) while lockout assembly (290) is in the locked position, either accidentally or in an attempt to provide RF energy to electrodes (213, 215), circuit board (208) would not activate electrodes (213, 215) due to both buttons (248, 245) not being depressed. In other words, the operator is prevented from activating RF energy to electrodes (213, 215) when the closure forces provided by jaws (212, 214) are not suitably conducive for sealing tissue via RF energy.

Also, while in the locked position, lockout ledge (296) is directly adjacent to a proximal surface (275) of firing assembly (250), thereby preventing proximal translation of proximal surface (275) while body (292) is in the locked position. As will be described in greater detail below, proximal translation of proximal surface (275) drives distal translation of knife (220) in order to sever tissue. Since lockout ledge (296) prevents proximal translation of proximal surface (275) while lockout assembly (290) is in the locked position, lockout ledge (296) also prevents distal translation of knife (220) while lockout assembly (290) is in the locked position. In other words, when lockout assembly (290) is in the locked position, the operator may be prevented from activating electrodes (213, 215) with RF energy, as well as prevented from distally actuating knife (220) to sever tissue.

Through holes (295) are dimensioned to allow suitable portions of electrode activation assembly (240) and firing assembly (250) to actuate within through holes (295). In the current example, one through hole (295) allows sliding body (246) of electrode activation assembly (240) to actuate within through hole (295) to access activation button (248); while another through hole (295) is dimensioned to allow a portion of firing assembly (250) to actuate within through hole (250) while translating body (292) is in the unlocked position. In the current example, lockout ledge (296) is housed within a portion of body (292) defining through hole (295), however this is merely optional.

FIGS. 15A-15C show an exemplary use of lockout assembly (290). FIG. 15A shows resilient arm (234) pivoted toward housing (232) such that jaws (212, 214) are in the closed position while resilient arm (234) is in a relaxed position. Therefore, jaws (212, 214) may not provide a sufficient closing force suitable for electrodes (213, 215) to seal tissue grasped by jaws (212, 214). Additionally, thumb ring (238) does not abut against translating body (292) such that spring (298) biases translating body (292) to the locked position. As mentioned above, since translating body (292) is in the locked position, the operator may not distally actuate knife (220) or provide RF energy to electrodes (213, 215) in accordance with the description herein.

Next, as seen in FIG. 15B, the operator may pivot resilient arm further toward housing (232) such that resilient arm bends to the flexed position. Additionally, thumb ring (238) abuts against translating body (292), overcoming the biasing force provided by spring (298), such that translating body (292) is in the unlocked position. At this point, the closure forces provided by jaws (212, 214) are sufficiently suitably for electrodes (213, 215) to seal tissue grasped by jaws (212, 214). At this point, lockout button (245) is depressed such that lockout button (245) is activated in accordance with the teachings herein. Additionally, as seen in FIG. 15C, while translating body (292) is in the unlocked position, and operator may actuate trigger (251) of firing assembly (250) such that knife (220) translates distally through elongate slot (216) to sever tissue grasped by jaws (212, 214) in accordance with the teachings herein. Because lockout ledge (296) no longer interferes with proximal translation of proximal surface (275), firing assembly (250) may actuate knife (220) distally. It should be understood that when the operator no longer presses resilient arm (234) toward housing (232) with enough force to keep arm (234) in the flexed position, the resilient nature of arm (234) will return arm (234) to the relaxed position, allowing spring (298) to bias translating body (292) back into the locked position.

As mentioned above, firing assembly (250) is configured to convert proximal translation of trigger (251) into distal translation of knife (220). As also mentioned above, a portion of firing assembly (250) and handle assembly (230) form an automatic knife return mechanism configured to automatically drive knife (220) to a pre-fired position after knife (220) reaches a predetermined distal position. Firing assembly (250) includes an input drive assembly (270), a rotary drive assembly (252), and an output drive assembly, such as a proximal rack (226) unitarily coupled with knife (220). As will be described in greater detail below, trigger (251) is configured to actuate input drive assembly (270) proximally such that rotary driver assembly (252) actuates proximal rack (226) and knife (220) distally. It should be understood that sliding body (246) of electrode activation assembly (240) may slide independently relative to firing assembly (250). Therefore, the operator may activate electrodes (213, 215) independently of firing assembly (250) and knife (220), in accordance with the description herein.

Input drive assembly (270) includes a first sliding member (272) and a second sliding member (280). Both sliding members (272, 280) are slidably contained within housing (232). As will be described in greater detail below, first sliding member (272) is configured to proximally drive second sliding member (280), while second sliding member (280) is configured to actuate rotary drive assembly (252).

Figure 11:
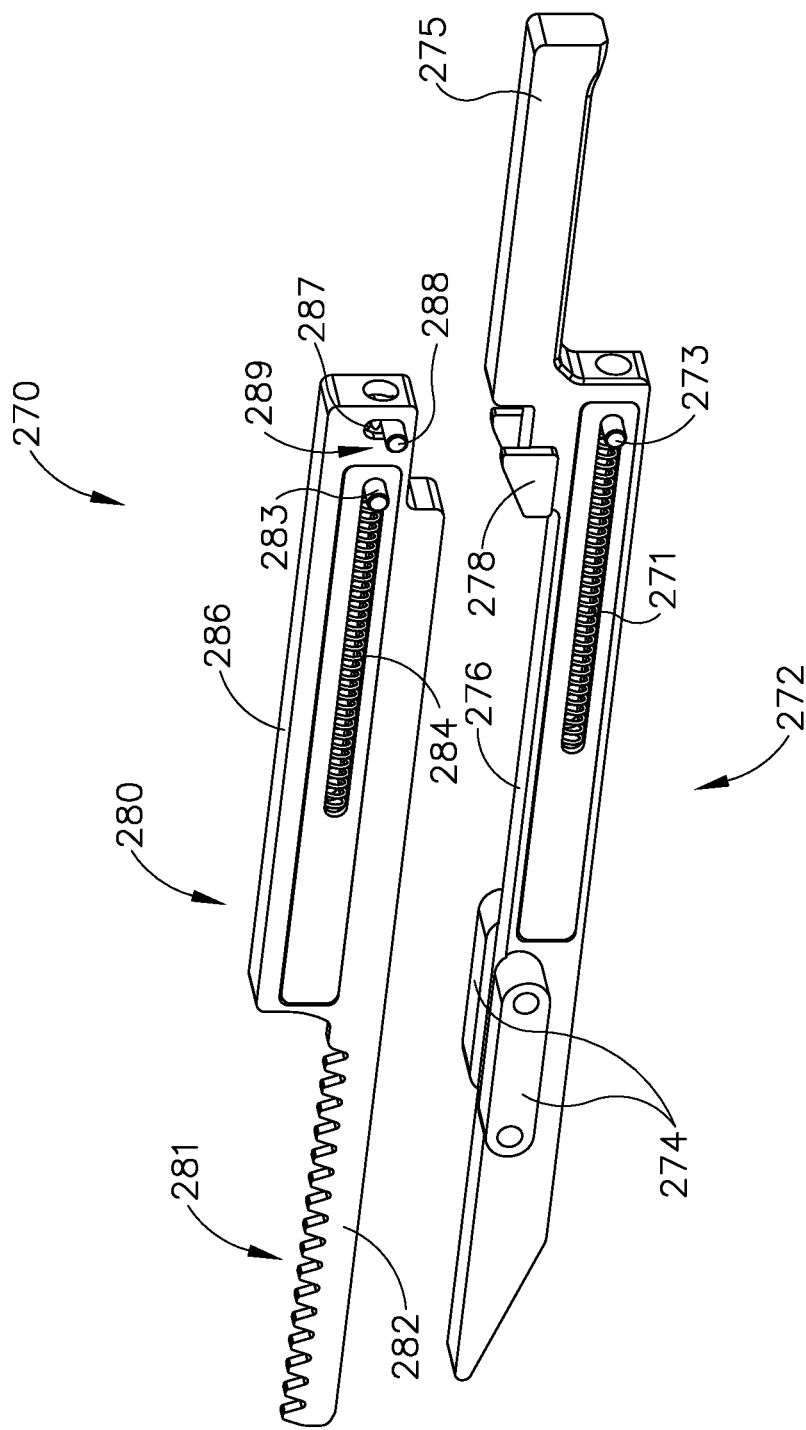
FIG. 11 depicts an exploded view of an input drive assembly of the firing assembly of FIG. 10.

As best seen in FIG. 11, first sliding member (272) includes a coupling block (274), a sliding body (276), a pair of laterally spaced projections (278), proximal surface (275), a grounding pin (273), and a biasing member (271) disposed within the confines of sliding body (276) and against grounding pin (273). Proximal surface (275) is configured to engage lockout assembly (290) is accordance with the teachings herein. Coupling block (274) is fixed relative to sliding body (276). Coupling block (274) is configured to couple with trigger (251) when instrument (200) is assembled such that actuation of trigger (251) relative to housing (232) drives actuation of coupling block (274) and sliding body (276) relative to housing (232). As will be described in greater detail below, projections (278) are dimensioned to drive portions of second sliding member (280) proximally in response to proximal translation of first sliding member (272). Grounding pin (273) is fixed to housing (232) when instrument (200) is assembled such that as sliding body (276) translates, grounding pin (273) remains spatially fixed relative to housing (232). Biasing member (271) abuts against grounding pin (273) and sliding body (276) in order to bias sliding body (276) to a distal, pre-fired position. Therefore, if the operator actuates trigger (251) proximally, biasing member (271) compresses such that when the operator releases trigger (251), biasing member (271) actuates trigger (251) to the distal, pre-fired, position. In the current example, biasing member (271) includes a spring, but any other suitably biasing member (271) may be used as would be apparent to one having ordinary skill in the art in view of the teachings herein.

Second sliding member (280) includes a distal rack (282), a sliding body (286), a grounding pin (283), a biasing member (284) disposed within the confines of sliding body (286), a transverse driving pin (288), and a second biasing member (287). Distal rack (282) includes a plurality of teeth (281). As will be described in greater detail below, teeth (281) are configured to mesh with portions of rotary drive assembly (252) such that translation of rack (282) rotates rotary drive assembly (252).

Grounding pin (283) is fixed to housing (232) when instrument (200) is assembled such that as sliding body (286) translates, grounding pin (283) remains spatially fixed relative to housing (232). Biasing member (284) abuts against grounding pin (283) and sliding body (286) in order to bias sliding body (286) to a distal, pre-fired position.

Sliding body (286) defines a slot (289) that slidably houses transverse driving pin (288). Second biasing member (287) biases transverse driving pin (288) to a downward position within slot (289). Transverse driving pin (288) may actuate within slot (289) to overcome the biasing force of second biasing member (287). Transverse driving pin (288) is dimensioned to abut against projections (278) of first sliding member (272) when in the downward position. Therefore, if the operator actuates trigger (251) proximally, first sliding member (272) may proximally drive second sliding member (280) via projection (278) and transverse driving pin (288). Additionally, as best shown in FIGS. 16A-16F, transverse driving pin (288) is housed within a slotted pathway (231) defined by the interior of housing (232). Therefore, as projections (278) drive transverse driving pin (288), a portion of pin (288) is within slotted pathway (231). As will be described in greater detail below, once first and second sliding members (272, 280) proximally translate a predetermined distance, transverse driving pin (288) may actuate within slot (289), due to contact with a cam surface (233) of slotted pathway (231), such that transverse driving pin (288) no longer engages projections (278). Therefore, with projections (278) no longer engaging driving pin (288), first biasing member (284) may distally drive sliding body (286) and rack (282) back to the distal, pre-fired position, which in turn may rotate rotary drive assembly (252).

As best shown in FIGS. 12-13, rotary drive assembly (252) includes an input pinion (254), an output pinion (256), a spacer (258), and a rotary pin (260). Input pinion (254) has a first diameter and includes a first plurality of teeth (255). Output pinion (256) has a second diameter and includes a second plurality of teeth (257). The second diameter of output pinion (256) is larger than the first diameter of input pinion (254). Spacer (258) is positioned between input pinion (254) and output pinion (256). Additionally, input pinion (254), output pinion (256), and spacer (258) each define a locking through hole (264).

Rotary pin (260) is rotatably coupled with housing (232) such that rotary pin (262) may rotate about its own axis relative to housing (232) but is otherwise fixed relative to housing (232). Rotary pin (260) includes an angular locking body (262) having a flat surface. Angular locking body (262) is dimensioned with fit through locking through holes (264) of pinions (254, 256) and spacer (258) such that pinions (254, 256) and spacer (258) unitarily rotate with rotary pin (260) relative to hosing (232). In other words, if input pinion (254) rotates 90 degrees about rotary pin (260) in a first angular direction, output pinion (256) also rotates 90 degrees about rotary pin (260) in the first angular direction.

First plurality of teeth (255) of input pinion (254) are configured to mesh with teeth (281) of distal rack (282) such that translation of distal tack (282) causes rotation of input pinion (254). Second plurality of teeth (257) of output pinion (256) are configured to mesh with teeth (228) of proximal rack (226) such that rotation of output pinion (256) drives translation of proximal rack (226) and knife (220). As can be seen in FIG. 10 and FIGS. 16A-16F, teeth (255) of input pinion (254) engage teeth (281) of distal rack (282) at one point, while teeth (257) of output pinion (256) engage teeth (228) of proximal tack (226) at a second point, spaced on the opposite side of rotary drive assembly (252). Therefore, proximal movement of input drive assembly (270) and distal rack (282) may cause rotation of rotary drive assembly (252) in a first angular direction via meshing of teeth (255, 281). Rotation of rotary drive assembly (252) in the first angular direction may cause distal movement of knife (220) and proximal rack (226) via meshing of teeth (257, 228). Alternatively, distal movement of input drive assembly (270) and distal rack (282) may cause rotation of rotary drive assembly (252) in a second angular direction via meshing of teeth (255, 281). Rotation of rotary drive assembly (252) in the second angular direction may cause proximal movement of knife (220) and proximal rack (226) via meshing of teeth (257, 228).

Because the diameter of output pinion (256) is greater than the diameter of input pinion (254), and because both pinion (254, 256) are configured to unitarily rotate together, knife (220) and proximal rack (226) may travel a greater distance than the displacement of distal rack (282) and input drive assembly (270). This may be advantageous as it may reduce the length the operator has to actuate trigger (251) in order to fire knife (220) distally.

Figure 14A:
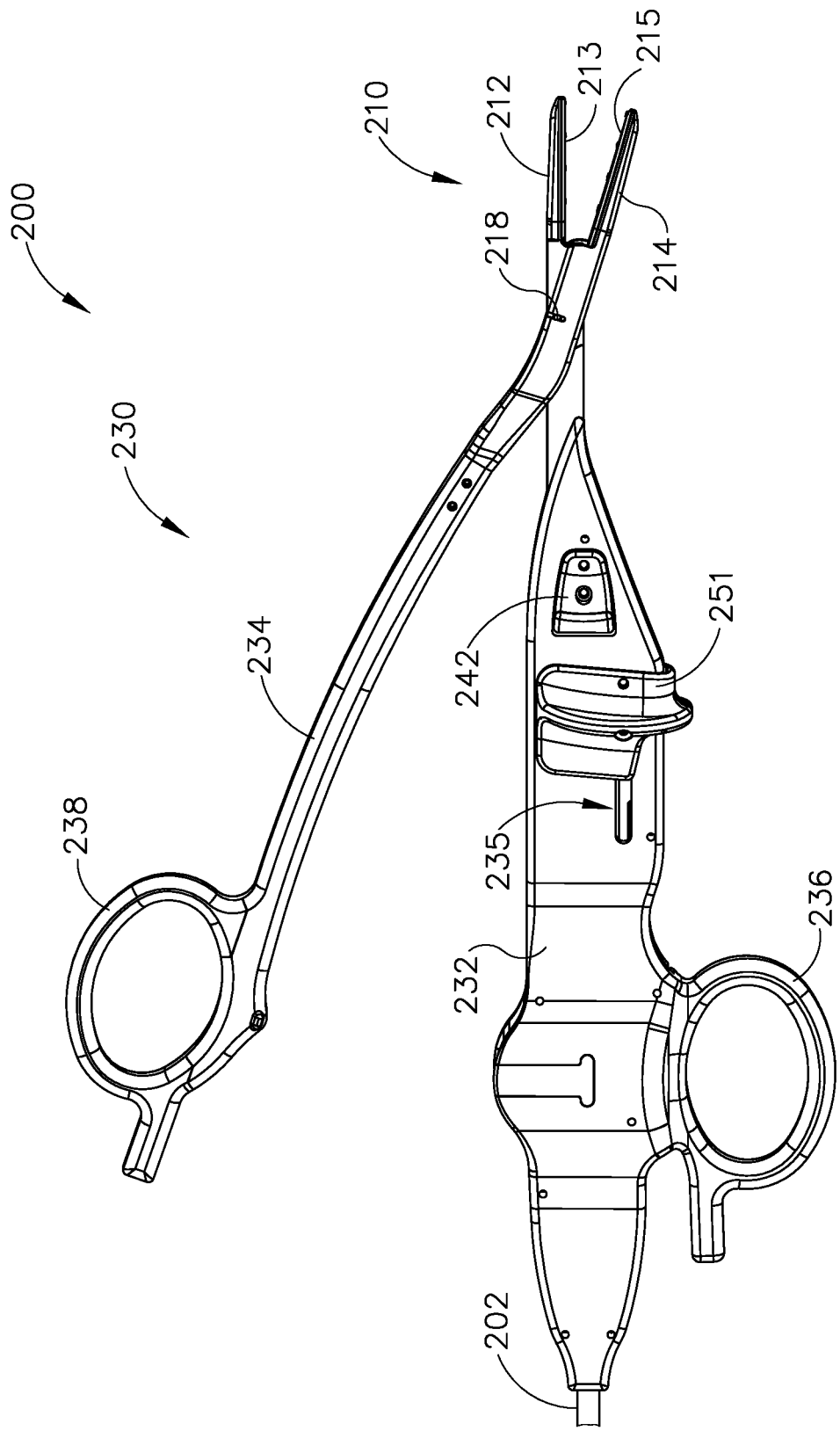
FIG. 14A depicts a side elevational view of the electrosurgical forceps instrument of FIG. 5, where the end effector is in the opened position, where the resilient arm is in the relaxed position, and where a translating knife of the end effector is in a proximal position.

FIGS. 14A-14D and FIGS. 16A-16F show an exemplary use of firing assembly (250) to actuate knife (220) through jaws (212, 214) to sever tissue. First, as shown in FIG. 14A, jaws (212, 214) of end effector (210) in the opened position. Therefore, resilient arm (234) is pivoted away from housing (232). It should be understood that lockout assembly (290) is in the locked configuration in accordance with the description herein when resilient arm (234) is in the position shown in FIG. 14A.

Figure 14B:
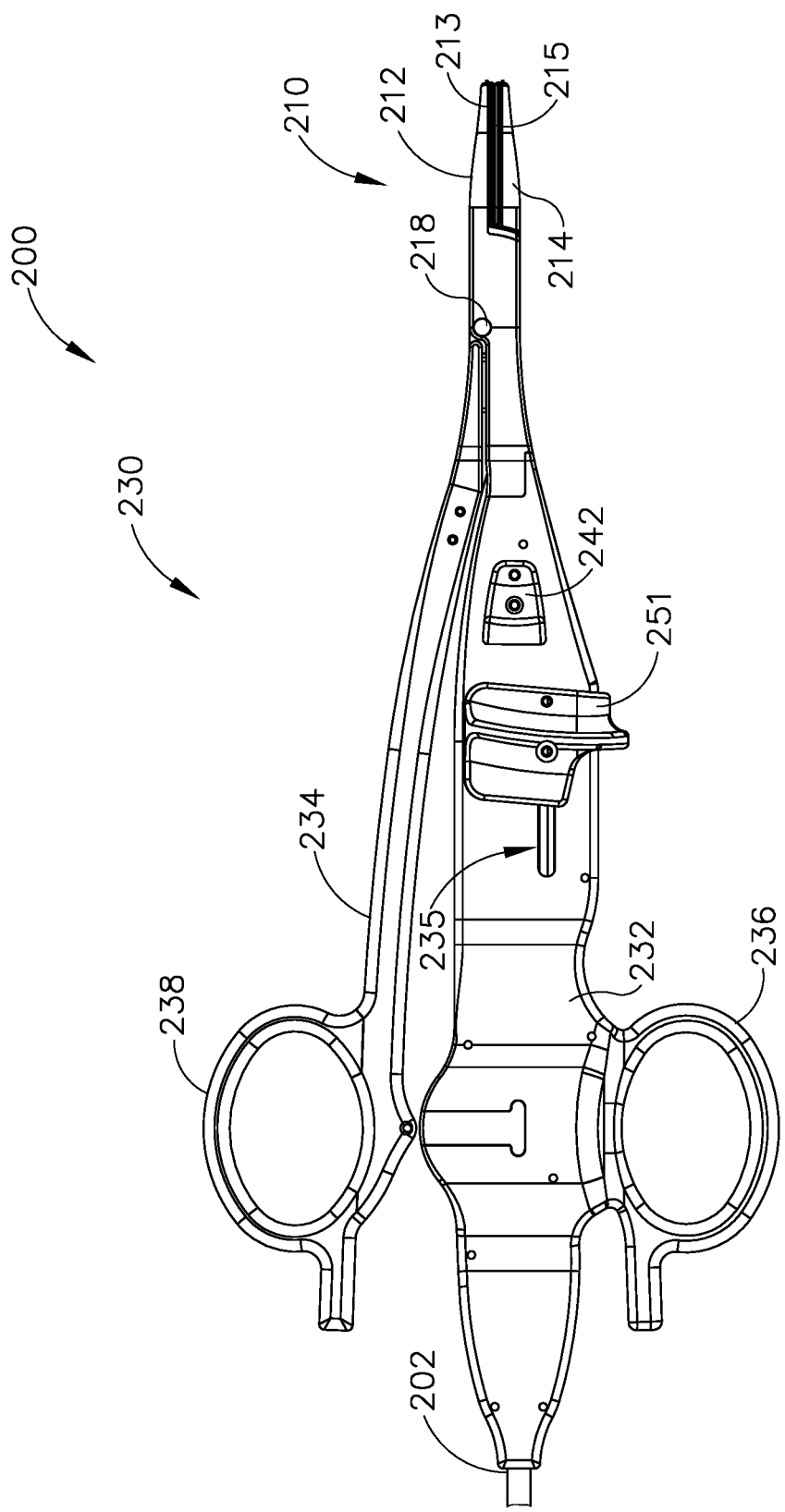
FIG. 14B depicts a side elevational view of the electrosurgical forceps instrument of FIG. 5, where the end effector is in the closed position, where the resilient arm is in the relaxed position, and where the translating knife of the end effector is in the proximal position.

Next, as shown in FIG. 14B, when the operator desires to initially grasp and manipulate tissue, the operator may pivot resilient arm (234) toward housing (232) such that jaws (122, 214) are pivoted toward the closed position while resilient arm (134) remains in the relaxed position. With jaws (212, 214) pivoted toward the closed position, the operator may manipulate tissue grasped by jaws (212, 214). It should be understood that the closure forces imparted on tissue by jaws (212, 214) at this point may not be sufficient enough to suitably seal tissue via RF energy provided by electrodes (213, 215). Additionally, lockout assembly (290) is in the locked configuration in accordance with the description herein.

Figure 14C:
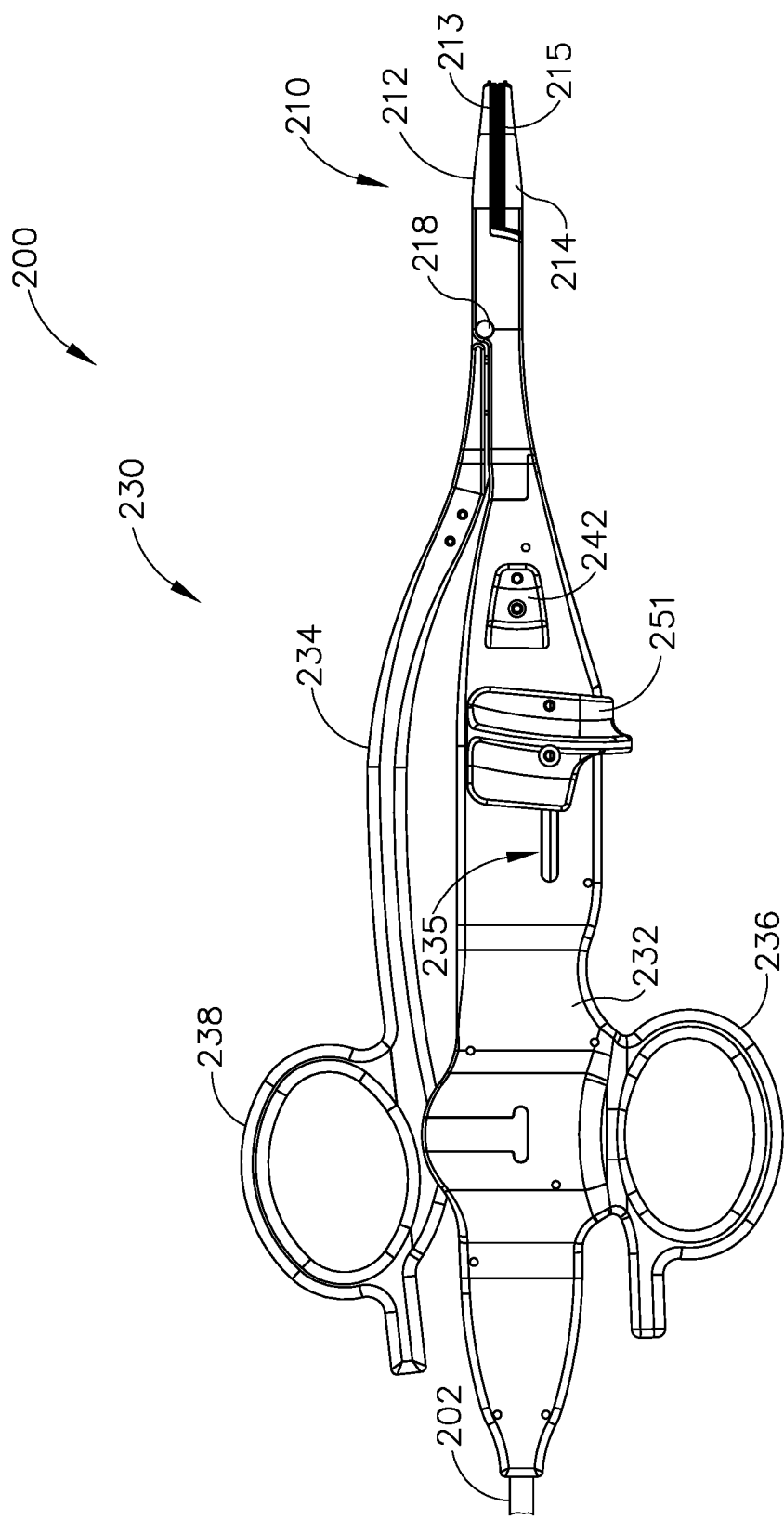
FIG. 14C depicts a side elevational view of the electrosurgical forceps instrument of FIG. 5, where the end effector is in the closed position, where the resilient arm is in a flexed position, and where the translating knife of the end effector is in the proximal position.
Figure 14D:
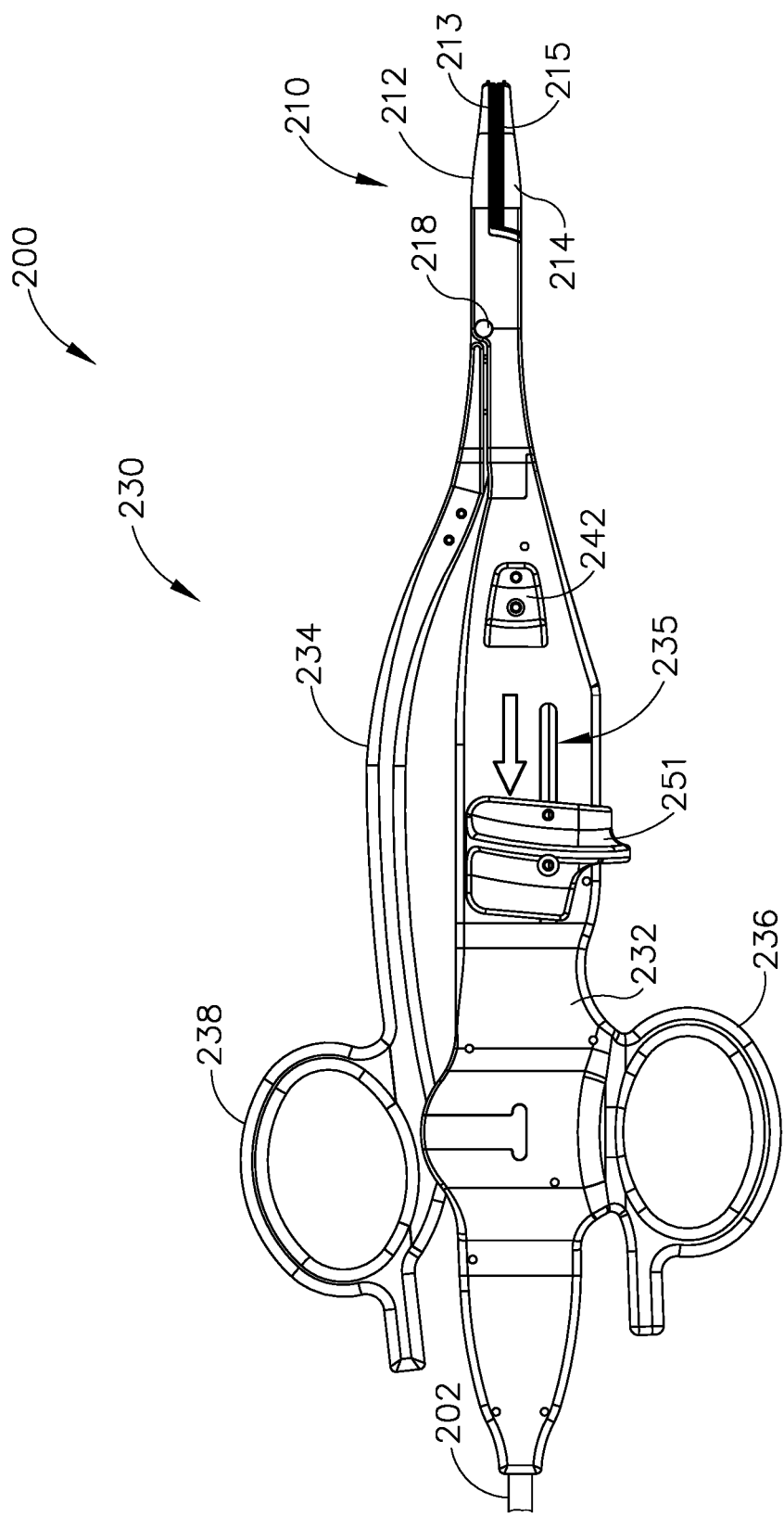
FIG. 14D depicts a side elevational view of the electrosurgical forceps instrument of FIG. 5, where the end effector is in the closed position, where the resilient arm is in the flexed position, and where the translating knife of the end effector is in a distal position.

Next, as shown in FIG. 14C, if the operator desires to apply RF energy to grasped tissue or sever grasped tissue, the operator may further pivot resilient arm (234) toward housing (232) such that resilient arm bends to the flexed position. As this point, the closure forces imparted on tissue by jaws (212, 214) is sufficient for proper sealing. Therefore, lockout assembly (290) is moved into the unlocked configuration in accordance with the description herein. With lockout assembly (290) in the unlocked configuration, the operator may activate electrodes (213, 215) or actuate knife (220) distally through jaws (212, 214).

Figure 16A:
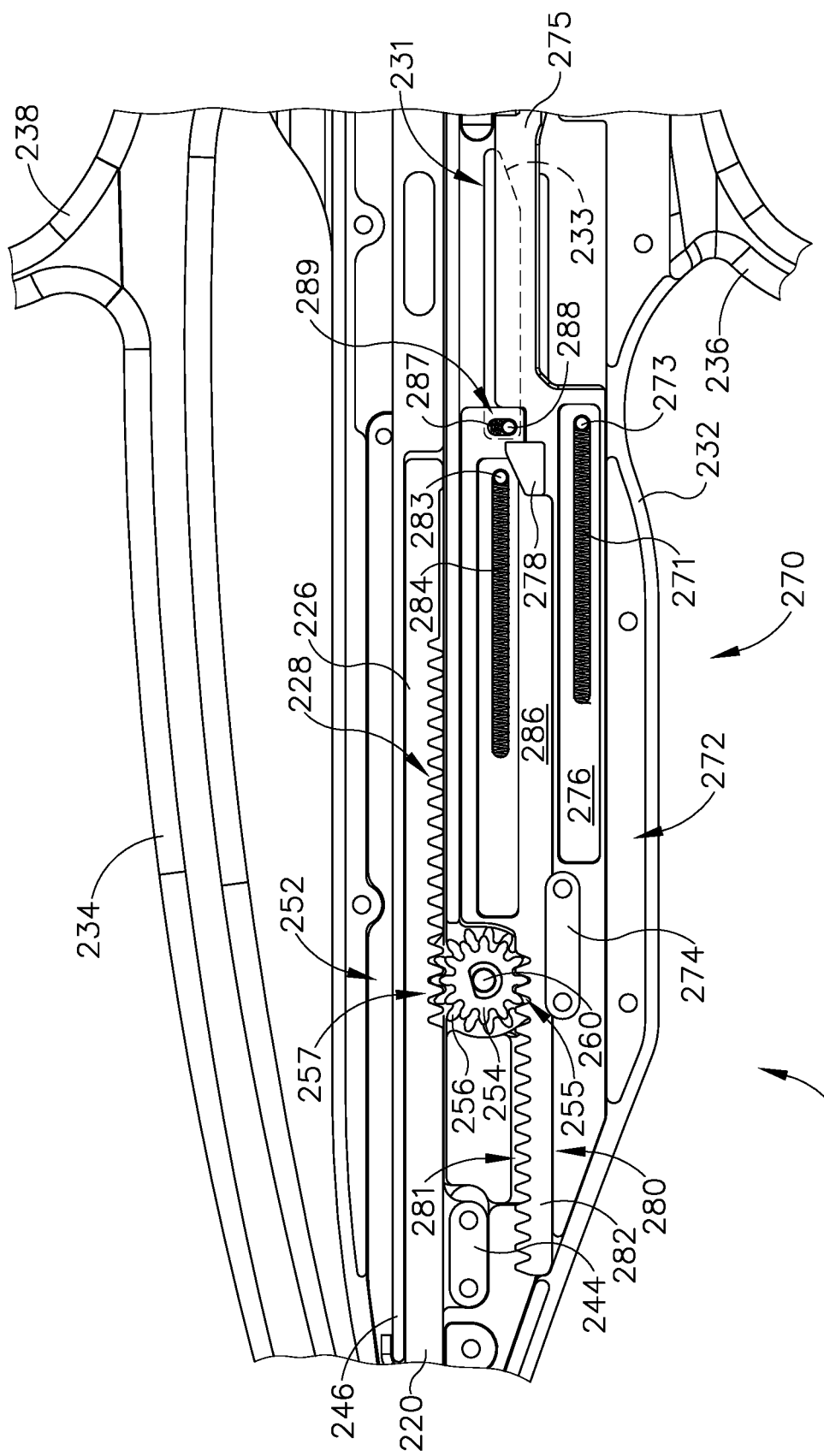
FIG. 16A depicts a side elevational view of a portion of the instrument of FIG. 5, with a portion of the handle assembly of FIG. 6 omitted for clarity, where firing assembly is in a first pre-fired position.
Figure 16B:
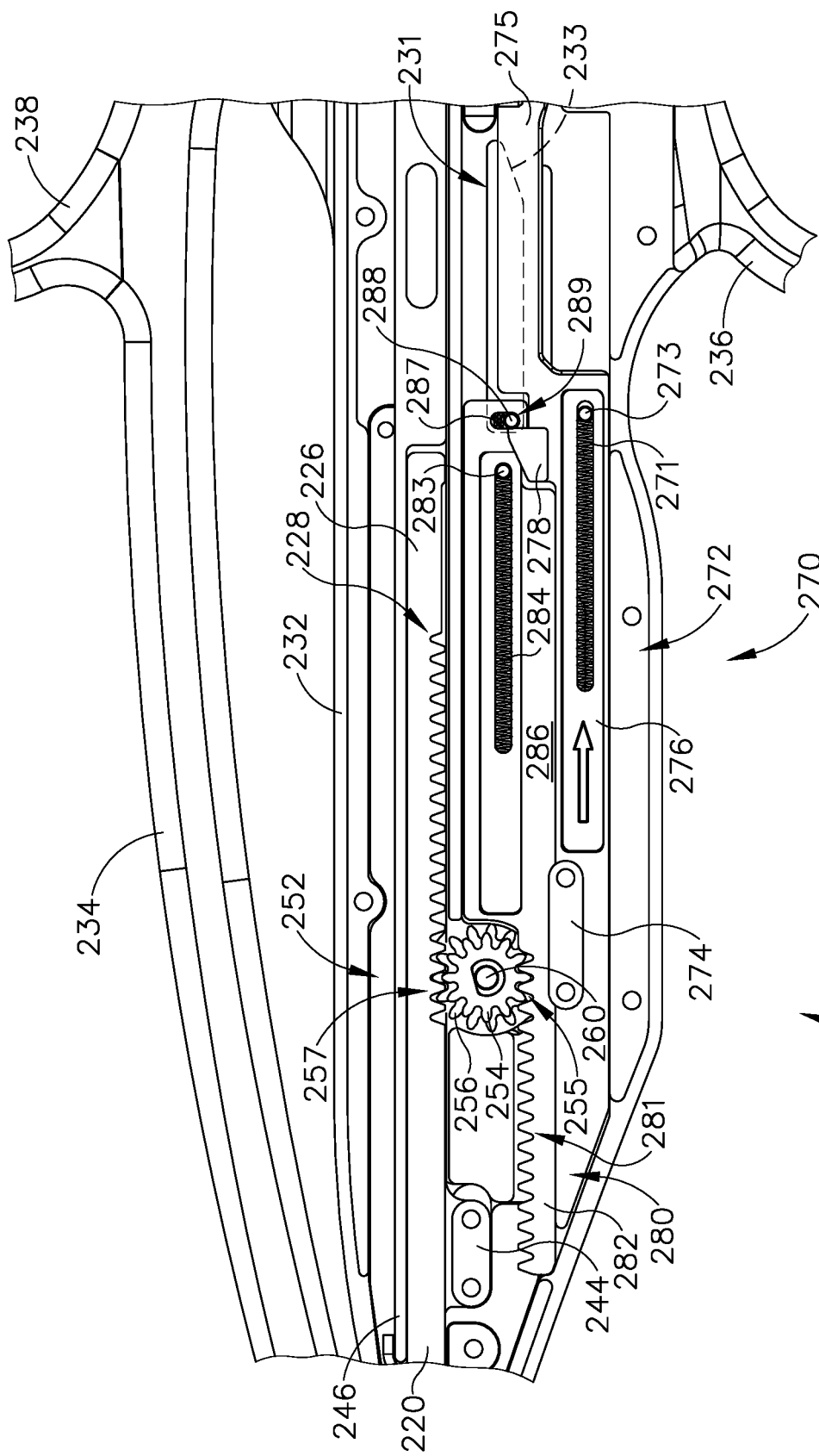
FIG. 16B depicts a side elevation view of a portion of the instrument of FIG. 5, with a portion of the handle assembly of FIG. 6 omitted for clarity, where the firing assembly is in a second pre-fired position.

FIGS. 16A-16F show an exemplary actuation of firing assembly (250) in order to actuate knife (222) from a proximal, pre-fired position, through jaws (212, 214) to a distal position, and back to the proximal, pre-fired position. FIG. 16A shows firing assembly (250) in the pre-fired position. Therefore, knife (220) is in a pre-fired position similar to that shown of knife (120) in FIG. 4A. When the operator desires to fire knife (220) distally within jaws (212, 214), the operator may pull trigger (251) proximally. As shown in FIG. 16B, while pulling trigger (251) proximally, first sliding member (272) may actuate proximally independently of second sliding member (280) until projections (278) make contact with transverse driving pin (288).

Next, as shown between FIGS. 14C-14D and FIGS. 16B-16C, the operator may further pull trigger (251) proximally such that first sliding member (272) and second sliding member (280) move proximally together due to projection (278) making contact with transverse driving pin (288). Therefore, distal rack (282) rotates input pinion (254) and the rest of rotary drive assembly (252) in the first angular direction due to meshing of teeth (281, 255). Because input pinion (254) and output pinion (256) unitarily rotate, output pinion (256) also rotates in the first angular direction, which in turn drives knife (220) and proximal rack (226) distally due to meshing of teeth (257, 228). As mentioned above, knife (220) may translate a further displacement distally than distal rack (282) translates proximally due the output pinion (256) having a larger diameter than input pinion (254). At the moment shown in FIG. 16C, knife (220) may have actuated substantially through jaws (212, 214), severing tissue captured between jaws (212, 214), similar to the position shown of knife (120) in FIG. 4B.

Figure 16C:
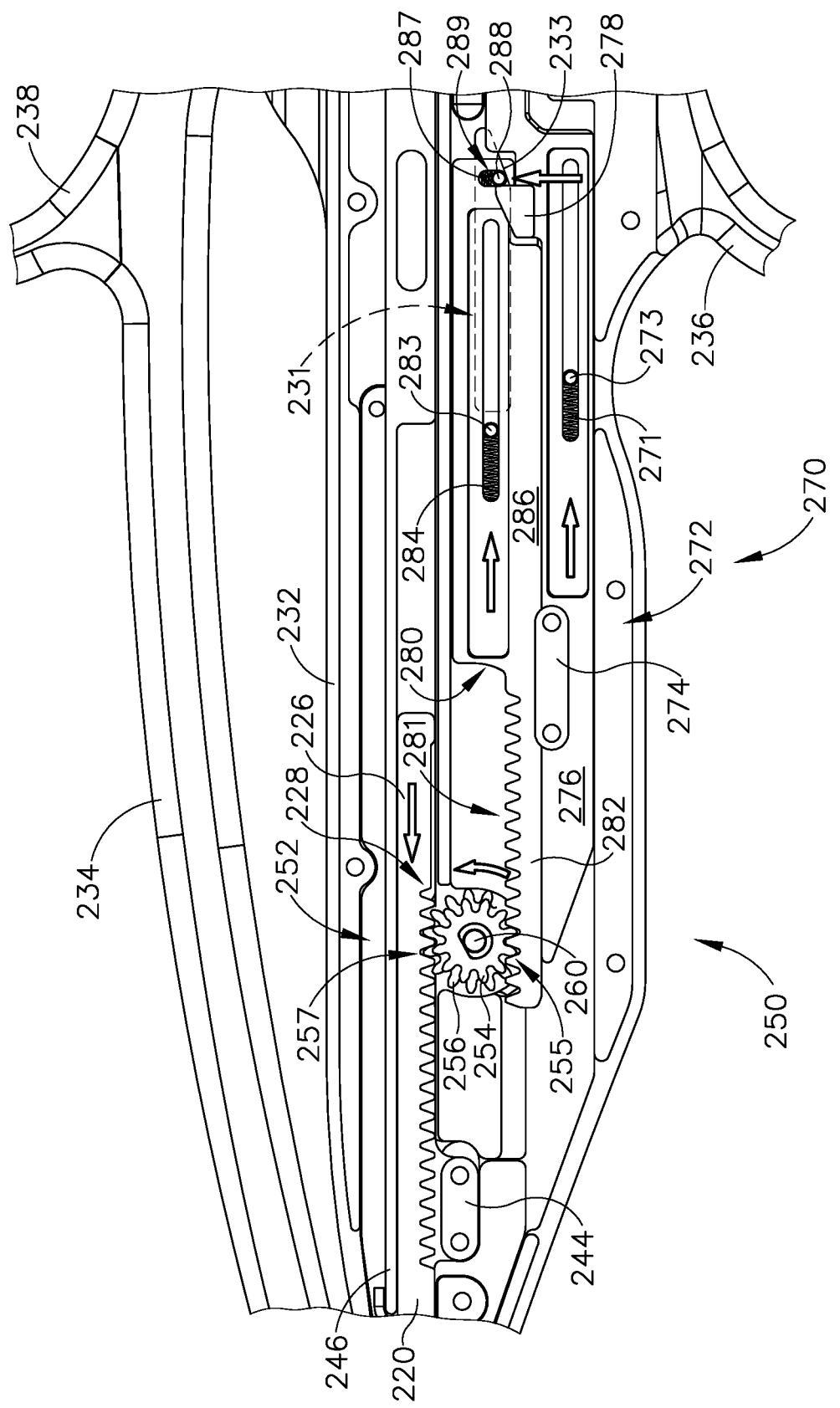
FIG. 16C depicts a side elevation view of a portion of the instrument of FIG. 5, with a portion of the handle assembly of FIG. 6 omitted for clarity, where the firing assembly is in a first fired position.
Figure 16D:
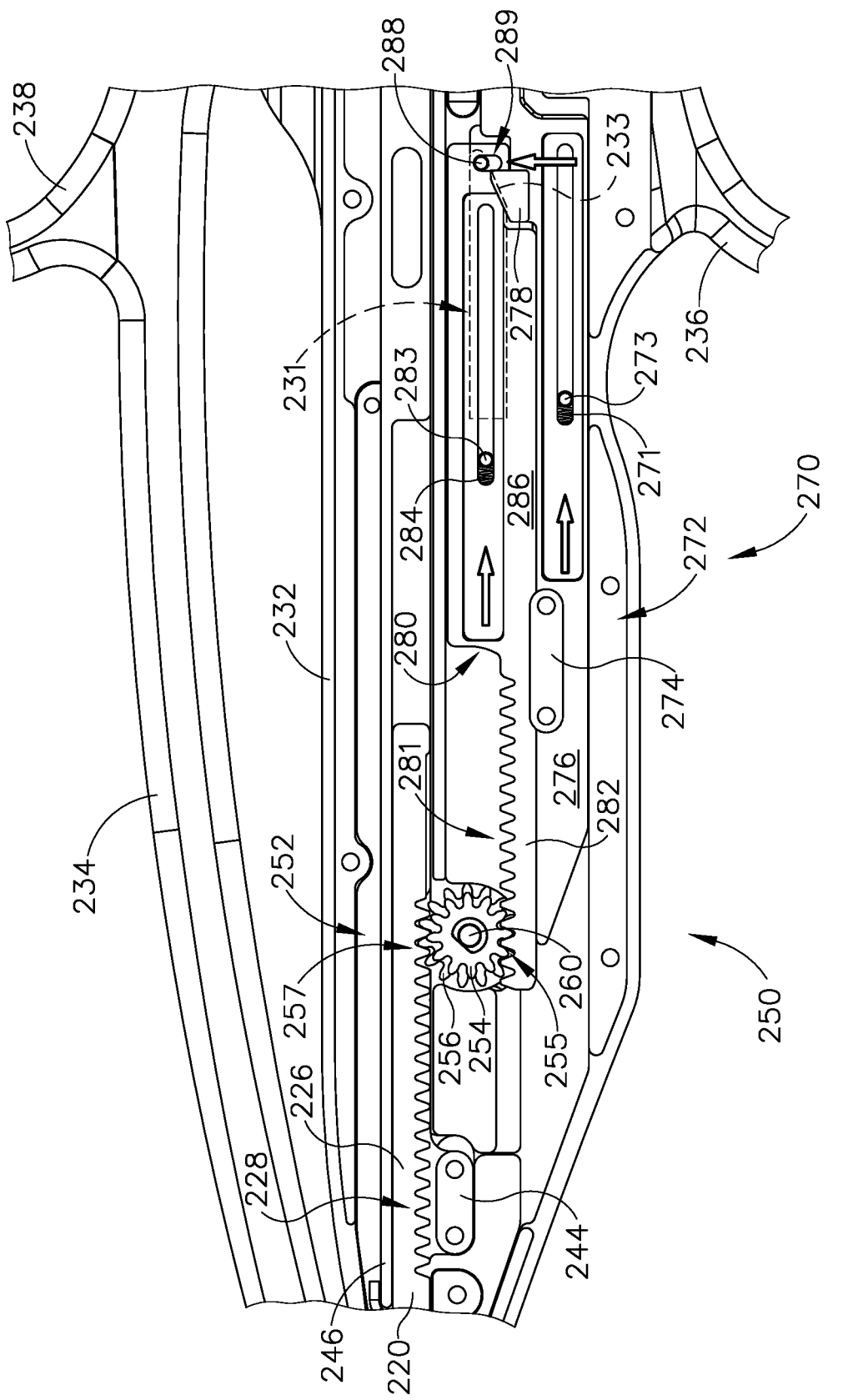
FIG. 16D depicts a side elevation view of a portion of the instrument of FIG. 5, with a portion of the handle assembly of FIG. 6 omitted for clarity, where the firing assembly is in a second fired position.

Because grounding pins (273, 283) are fixed relative to housing (232), movement of sliding bodies (276, 286) compresses biasing members (271, 284) between grounding pins (273, 283) and the interior of sliding bodies (276, 286), respectively. As mentioned above, transverse driving pin (288) is partially housed within slotted pathway (231) defined within housing (232). FIG. 16C shows transverse driving pin (288) at a position just distal to cam surface (233) of slotted pathway (231). If the operator pulls trigger (251) further in the proximal direction, as shown in FIG. 16D, transverse driving pin (288) will come into contact with cam surface (233) of slotted pathway (231). Cam surface (233) will push transverse driving pin (288) upwards within slot (289) overcoming the biasing force of second biasing member (287).

Figure 16E:
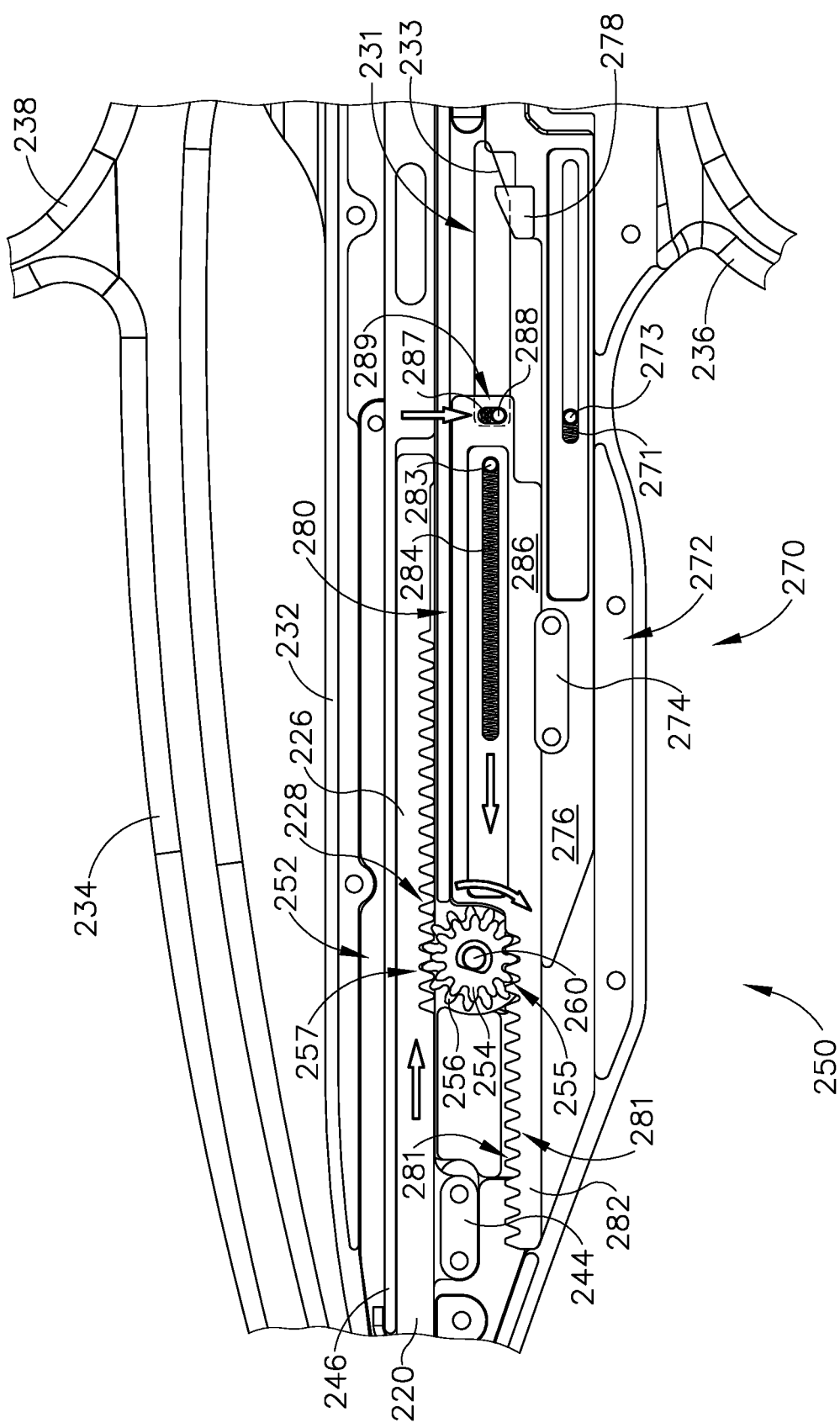
FIG. 16E depicts a side elevation view of a portion of the instrument of FIG. 5, with a portion of the handle assembly of FIG. 6 omitted for clarity, where the firing assembly is in a pre-returned, post-fired position.

As also shown in FIG. 16D, cam surface (233) may push transverse driving pin (288) upwards until pin (288) is no longer engaged with projections (278). With pin (288) no longer engaged with projections (278), first biasing member (284) may push against grounding pin (283), therefore actuating second sliding member (280) in the distal direction, as shown in FIG. 16E. Distal actuation of second sliding member (280) causes rack (282) to rotate input pinion (254) in the second angular direction, which in turn rotates output pinion (256) in the second angular direction, which causes proximal translation of knife (220) and rack (228). In particular, knife (220) may travel all the way back to the pre-fired position. Once actuated proximally past cam surface (233), biasing member (287) may bias transverse pin (288) back within slot (289). Projections (278) may also interact with transverse driving pin (288) and second biasing member (287) such that projections (278) may push pin (288) upward out of engagement with projections (278) when knife (220) experiences an excess load, such as when knife (220) encounters an undesirable object. For example, if knife (230) encounters an object difficult to cut, projections (278) may overcome the biasing force of second biasing member (287) such that transverse driving pin (288) actuates upward within slot (289). In other words, if knife (220) encounters an object too difficult to cut, contact between projections (278) and transverse driving pin (288) may generate a force that actuates pin (288) within slot (289) such that pin (288) and projection (278) are no longer in engagement, instead of proximally driving second sliding member (280). Therefore, second sliding member (280) decouples with first sliding member (272) prior to knife (220) reaching the fired position, and knife (220) automatically travels back to the pre-fired position due to first biasing member (284) driving sliding body (286) distally. This may help prevent knife (220) from being damaged.

It should be understood that second sliding member (280) returns to the pre-fired position even though first sliding member (272) is still in the fired position. Therefore, once the operator pulls trigger (251) far enough proximally to complete the distal actuation of knife (220), second sliding member (280) may disengage with first sliding member (272) and automatically return knife (220) to the pre-fired position, regardless if the operator holds trigger (251) in the proximal position. In other words, cam surface (233) of slotted pathway (231), transverse pin (288), and biasing members (184, 187) may act as an automatic knife return mechanism to return knife (220) to the pre-fired poison automatically after reaching a predetermined distal location.

Figure 16F:
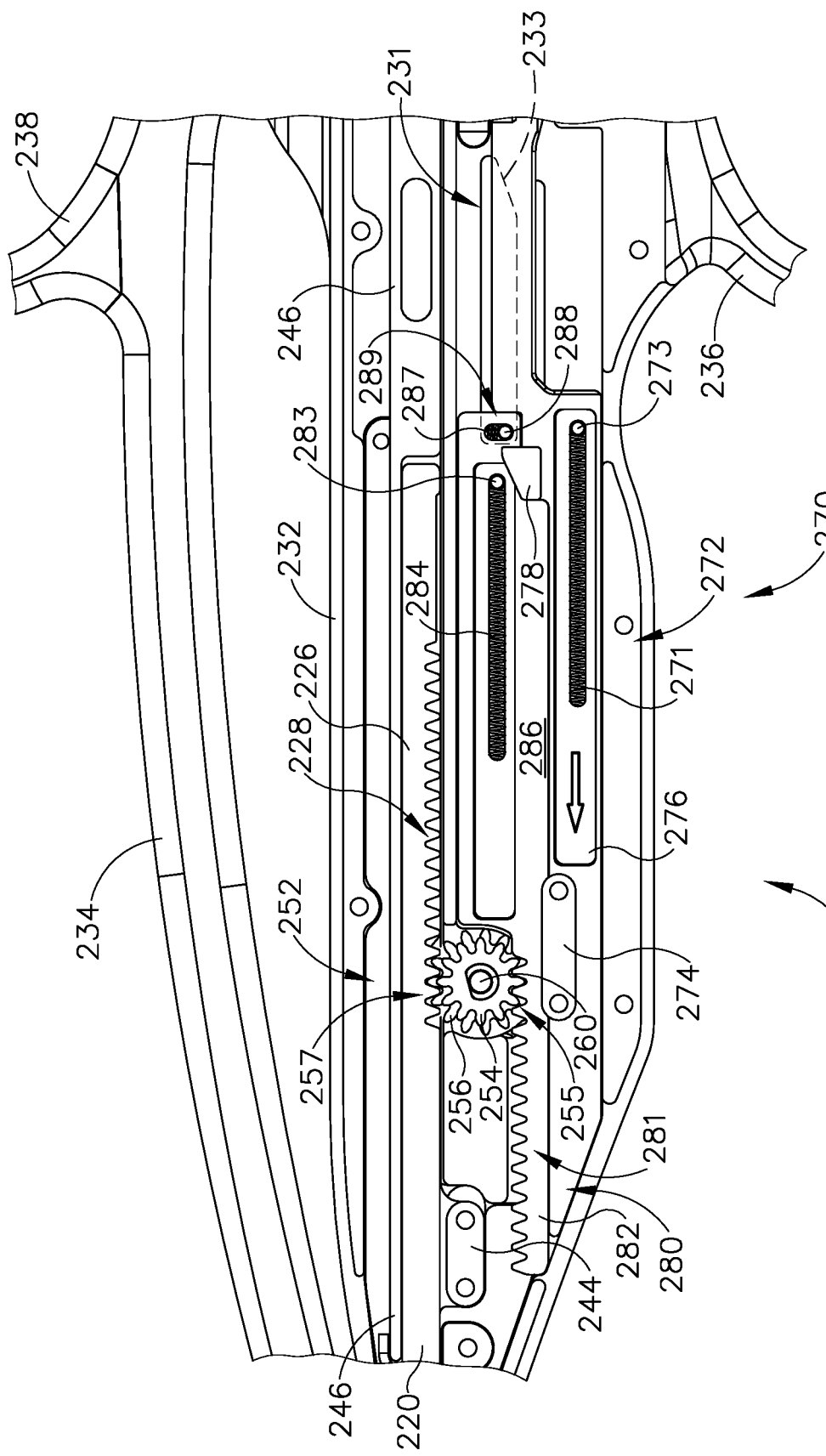
FIG. 16F depicts a side elevational view of a portion of the instrument of FIG. 5, with a portion of the handle assembly of FIG. 6 omitted for clarity, where the firing assembly is fully returned to the first pre-fired position.
Figure 17:
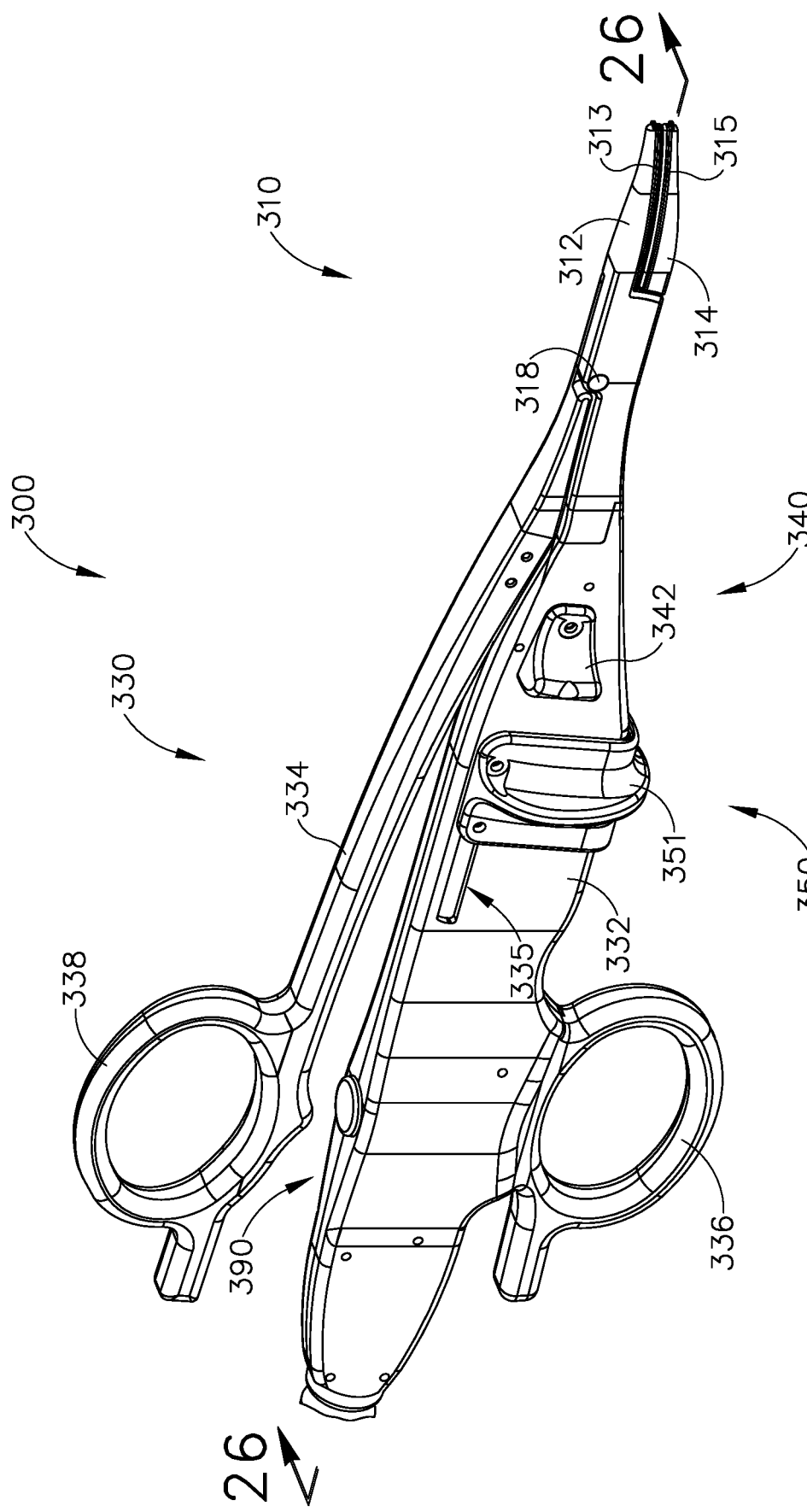
FIG. 17 depicts a perspective view of another exemplary electrosurgical forceps instrument, where an end effector is in a closed position, where a resilient arm is in a relaxed position.
Figure 18:
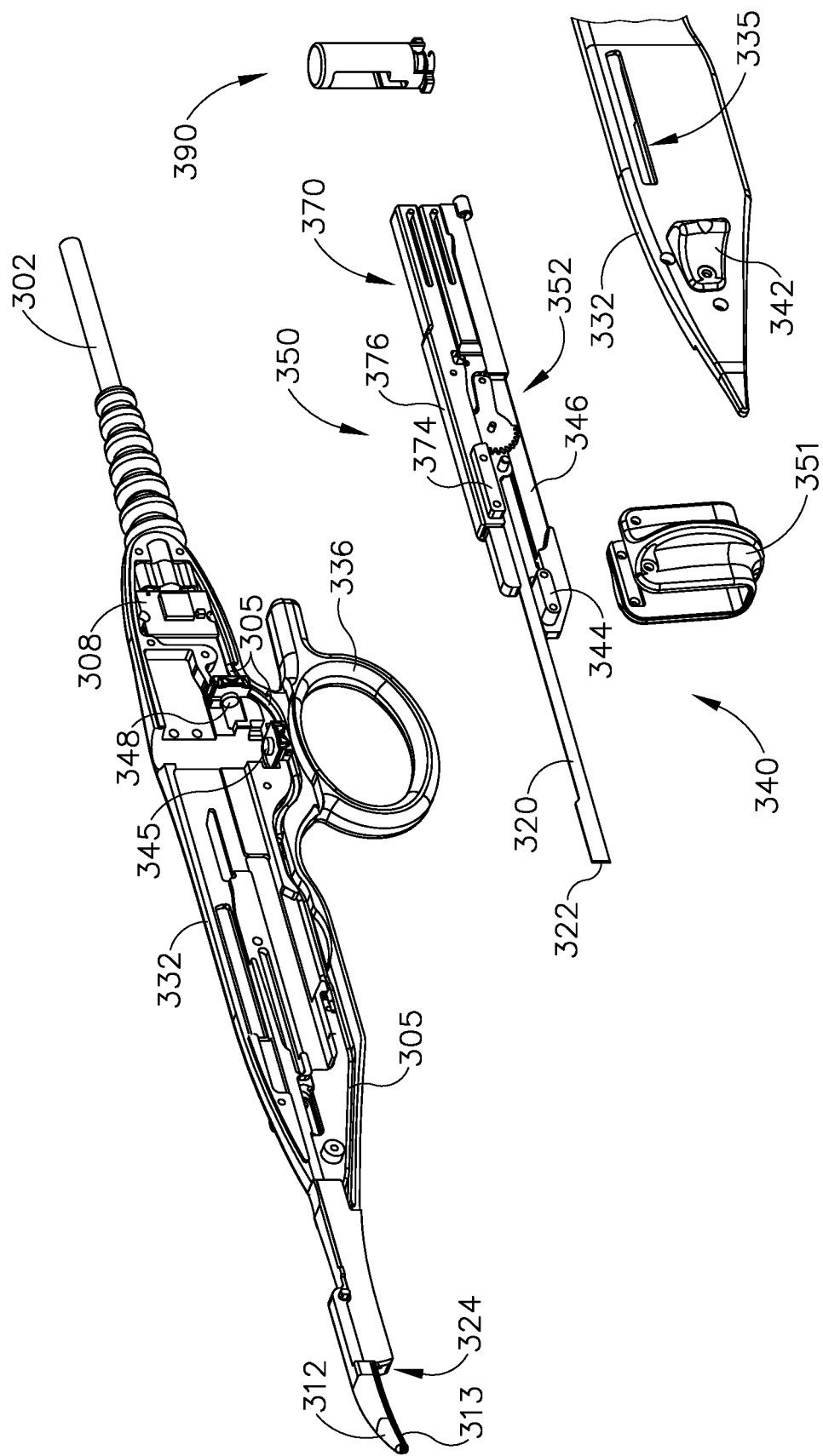
FIG. 18 depicts an exploded perspective view of a handle assembly of the electrosurgical forceps instrument of FIG. 17.

As shown between FIGS. 16E-16F, the operator may release trigger (251) such that biasing member (271) pushes first sliding member (272) back to the position shown in FIG. 16A. The operator may then re-fire knife (220) in accordance with the description herein.

B. Exemplary Instrument with Rotating Arm and Link Firing Assembly, Lockout Mechanism, and Knife Return Feature FIG. 6 shows an alternative exemplary electrosurgical forceps instrument (300) that may be used in replacement of instrument (100) described above. Therefore, as will be described in greater detail below, instrument (300) may be used to grasp, seal, and sever tissue.

Instrument (300) includes an end effector (310), a handle assembly (330), an electrode activation assembly (340), a firing assembly (350), and a lockout assembly (390). End effector (310) is substantially similar to end effector (110) described above, with differences elaborated below. End effector (310) includes a first jaw (312) having a first electrode (313), a second jaw (314) having a second electrode (315), and a knife (320) configured to translate through the first jaw (312) and the second jaw (314).

First jaw (312) and second jaw (314) are pivotably coupled with each other via pivot pin (318). Similar to jaws (112, 114) described above, first jaw (312) and second jaw (314) may pivot between an open position and a closed position in order to grasp tissue. First and second electrodes (313, 315) are positioned on respective jaws (312, 314) such that electrodes (313, 315) face each other when jaws (312, 314) are pivoted into the closed position. Additionally, each electrode (313, 315) is U-shaped in the present example, with the bend of the U-shape located near the distal end of each respective jaw (312, 314), such that each electrode (313, 315) includes two longitudinally extending, laterally spaced-apart legs extending along the length of each respective jaw (312, 314). Laterally spaced-apart legs of each electrode (313, 315) and corresponding portions of jaws (312, 314) define an elongate slot (316). Elongate slot (316) is dimensioned to slidably receive knife (320) such that knife may translate from a proximal position to a distal position, similar to knife (120) described above. As best shown in FIGS. 18 and 22-24, knife (320) includes a distal cutting edge (322) configured to sever tissue captured between jaws (312, 314) in the closed position.

A cable (302) extends proximally from handle assembly (330). Similar to cable (102) of instrument (100), cable (302) is configured to couple with control unit (104), which is further coupled with a power source (106). Therefore, control unit (104) is operable to provide RF power to electrodes (313, 315) of jaws (312, 314), to thereby seal tissue suitably captured between jaws (312, 314).

Handle assembly (330) includes a housing (332) and a resilient arm (334). Housing (332) and resilient arm (334) are substantially similar to housing (122) and resilient arm (134) described above, with differences elaborated below. Housing (332) and resilient arm (334) are pivotably coupled with each other via pivot pin (318). Housing (332) extends distally into first jaw (312), while resilient arm (334) extends distally into second jaw (314). Housing (332) defines a knife pathway (324) that slidably houses a portion of knife (320). Housing (332) includes a finger ring (336) while resilient arm (334) terminates proximally into a thumb ring (338). Therefore, the operator may grasp instrument (300) in a scissor grip fashion and pivot resilient arm (334) relative to housing (332) via rings (336, 338) in order to open and close jaws (312, 314).

Similar to resilient arms (134, 234) described above, resilient arm (334) is sufficiently resilient such that arm (334) may flex from a relaxed position to a flexed position in response to pivoting arm (334) further toward housing (332) when jaws (312, 314) are already in the closed position. Resilient arm (334) is biased toward the relaxed position. Further pivoting of resilient arm (334) into the flexed position may result in greater closure forces between jaws (312, 314) as compared to pivoting jaws (312, 314) into the closed position while arm (334) is in the relaxed position. Resilient arm (334) may be suitably resilient such that when resilient arm (334) is pivoted into the flexed position, the closure force between jaws (312, 314) is sufficient such that electrodes (313, 315) may properly seal tissue grasped between jaws (312, 314). Additionally, the resilient nature of arm may limit the amount of closure force between jaws (312, 314) such that jaws (312, 314) may not compress tissue too much, resulting in inadvertent tissue damage. When the operator no longer desires to compress tissue between jaws (312, 314) to properly seal or sever clamped tissue, the operator may reduce the amount of closure force applied to resilient arm (334) such that arm (334) returns to the relaxed state.

Housing (332) contains electrode activation assembly (340), firing assembly (350), and lockout assembly (390). Firing assembly (350) of the current example include a knife trigger (351) slidably coupled with housing (332) via a slot (335). As will be described in greater detail below, electrode activation assembly (340) is configured to selectively activate electrodes (313, 315); firing assembly (350) is configured to actuate knife (320) between the proximal position and the distal position (Similar to knife (120) as shown in FIGS. 4A-4B) in response to proximal translation of knife trigger (351) within slot (335); and lockout assembly (390) is configured to prevent actuation of knife (320) until specific conditions are satisfied. In some examples, lockout assembly (390) may be configured to prevent activation of electrodes (313, 315) until specific conditions are satisfied, or indicate when jaws (212, 214) are sufficiently closed for suitably sealing tissue. As will also be described in greater detail below, a portion of firing assembly (350) and handle assembly (330) form an automatic knife return mechanism configured to automatically drive knife (320) to the proximal, pre-fired, position after knife (320) reaches a predetermined distal position.

Electrode activation assembly (340) includes an RF trigger (342) slidably supported on each lateral side of housing (332), a sliding body (346) slidably contained within housing (332), a coupling block (344) fixed relative to sliding body (346), an activation button (348), and a lockout button (345). Coupling block (344) is configured to couple with each RF trigger (342) when instrument (300) is assembled. A proximal end of sliding body (346) is directly adjacent to activation button (348) such that proximal translation of sliding body (346) triggers activation button (348). Therefore, the operator may press RF trigger (342) proximally in order to compress activation button (348). RF trigger (342), coupling block (344), and/or sliding body (346) may be biased toward a position such that activation button (348) is not activated.

Activation button (348) and lockout button (345) are each contained within housing (332). Lockout button (345) and activation button (348) are each in communication with a circuit board (308) via electrical coupling wires (305); while circuit board (308) is also in communication with at least one electrode (313, 315) via electrical coupling wires (305). In the present example, circuit board (308) is contained within housing (332). Circuit board (308) is in communication with cable (302) such that circuit board (308) and control unit (104) are in electrical communication with each other. Therefore, circuit board (308) is configured to transfer RF energy from control unit (104) to electrodes (313, 315). As will be described in greater detail below, lockout assembly (390) is configured to depress lockout button (245) when jaws (312, 314) are sufficiently closed to provide sufficient closure force to properly seal tissue captured between electrodes (313, 315) using RF energy.

In the present example, activation button (348) and lockout button (345) are configured to instruct circuit board (308) to transfer RF energy from control unit (104) to electrodes (313, 315) when buttons (345, 348) are depressed. If only one, or neither, button (345, 348) is depressed, circuit board (208) will not transfer RF energy to electrodes (313, 315), thereby leaving electrodes (313, 315) deactivated. Therefore, for example, if the operator pressed RF trigger (342) without having lockout button (345) depressed, electrodes (313, 315) will remain deactivated. Alternatively, lockout button (345) may act as a switch for activation button (348) such that activation of lockout button (345) completes a circuit between at least one electrode (313, 315) and activation button (348).

In another example, lockout button (345) may only generate a signal to circuit board (308), which may then send the signal to control unit (104), that jaws (312, 314) are sufficiently closed to provide sufficient closure force to properly seal tissue captured between electrodes (313, 315) using RF energy. Control unit (104) may then signal to the operator (e.g., visually, audibly, and/or tactilely) that jaws (312, 314) are sufficiently closed. In such examples, activation button (348) may independently instruct circuit board (308) to transfer RF energy from control unit (104) to electrodes (313, 315) when activation button (348) is depressed.

In another example, depression of either activation button (348) or lockout button (345) may activate electrodes (313, 315), but activation of buttons (345, 348) may send a different signal to control unit (104), such that control unit produces a different signal (e.g., visually, audibly, and/or tactilely) indicating to a user which button (345, 348) has been depressed.

In yet another example, activation button (348) may be omitted entirely such that pressing lockout button (345) leads to activation of electrodes (313, 315).

While in the current example, circuit board (308) acts as an intermediary between control unit (104), electrodes (313, 315), and buttons (345, 348), this is merely optional, as buttons (345, 348) and electrodes (313, 315) may be in communication with cable (302) and control unit (104) without the use of circuit board (308).

Figure 20:
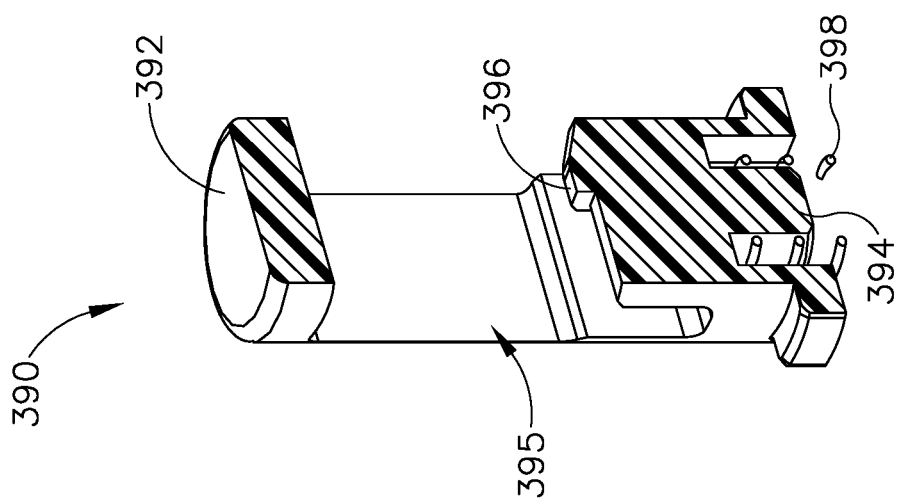
FIG. 20 depicts a cross-sectional view of the lockout assembly of FIG. 19, taken along line 20-20 of FIG. 19.
Figure 19:
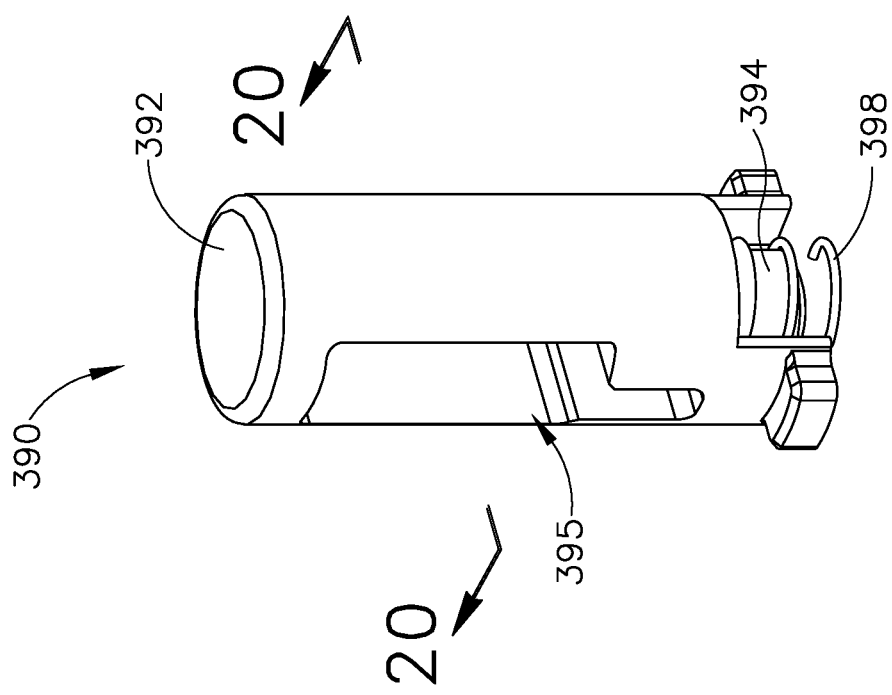
FIG. 19 depicts a perspective view of a lockout assembly of the electrosurgical forceps instrument of FIG. 17.

As mentioned above, lockout assembly (390) is configured to either indicate when jaws (312, 314) are sufficiently closed or to prevent activation of electrodes (313, 315) until jaws (312, 314) are sufficiently closed; while lockout assembly (390) is also configured to prevent actuation of knife (320) until specific conditions are satisfied. As best seen in FIGS. 19-20, lockout assembly (390) includes a translating body (392) defining a through holes (395), and a bias spring (398). Translating body (392) includes a button (394) extending downwardly from the rest of body (392), and a lockout ledge (396). Translating body (392) is slidably disposed within housing (332). Translating body (392) is configured to actuate between a locked position (as shown in FIGS. 21 and 26A) to an unlocked position (as shown in FIGS. 26B-26C); while bias spring (398) abuts against an interior portion of housing (332) and translating body (392) to bias translating body (392) toward the locked position.

Figure 26A:
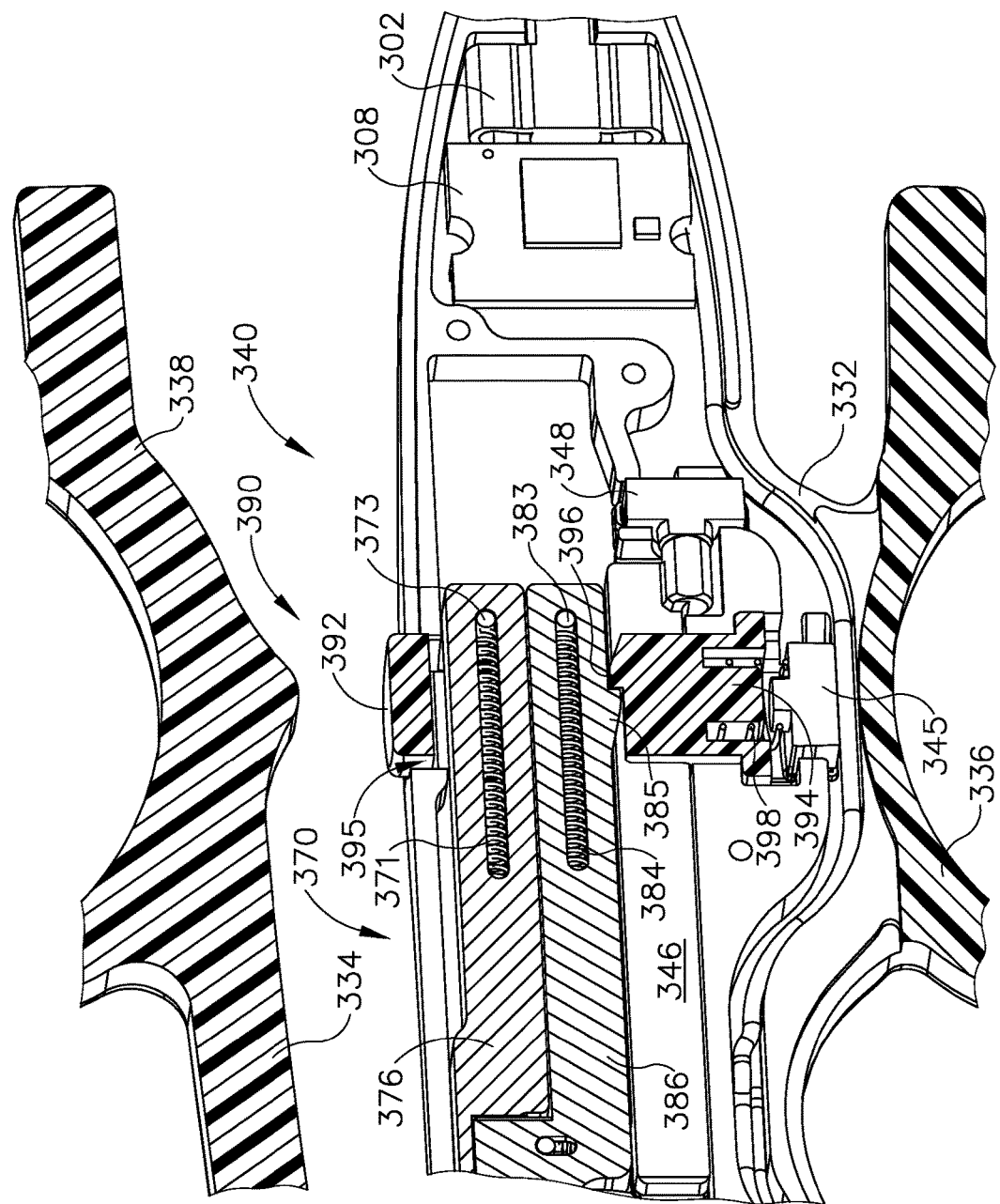
FIG. 26A depicts a cross-sectional view of a portion of the instrument of FIG. 17, taken along line 26-26 of FIG. 17, where the resilient arm is in a relaxed position, where the lockout assembly of FIG. 19 is in a locked position, and where the firing assembly of FIG. 22 is in a pre-fired position.
Figure 26B:
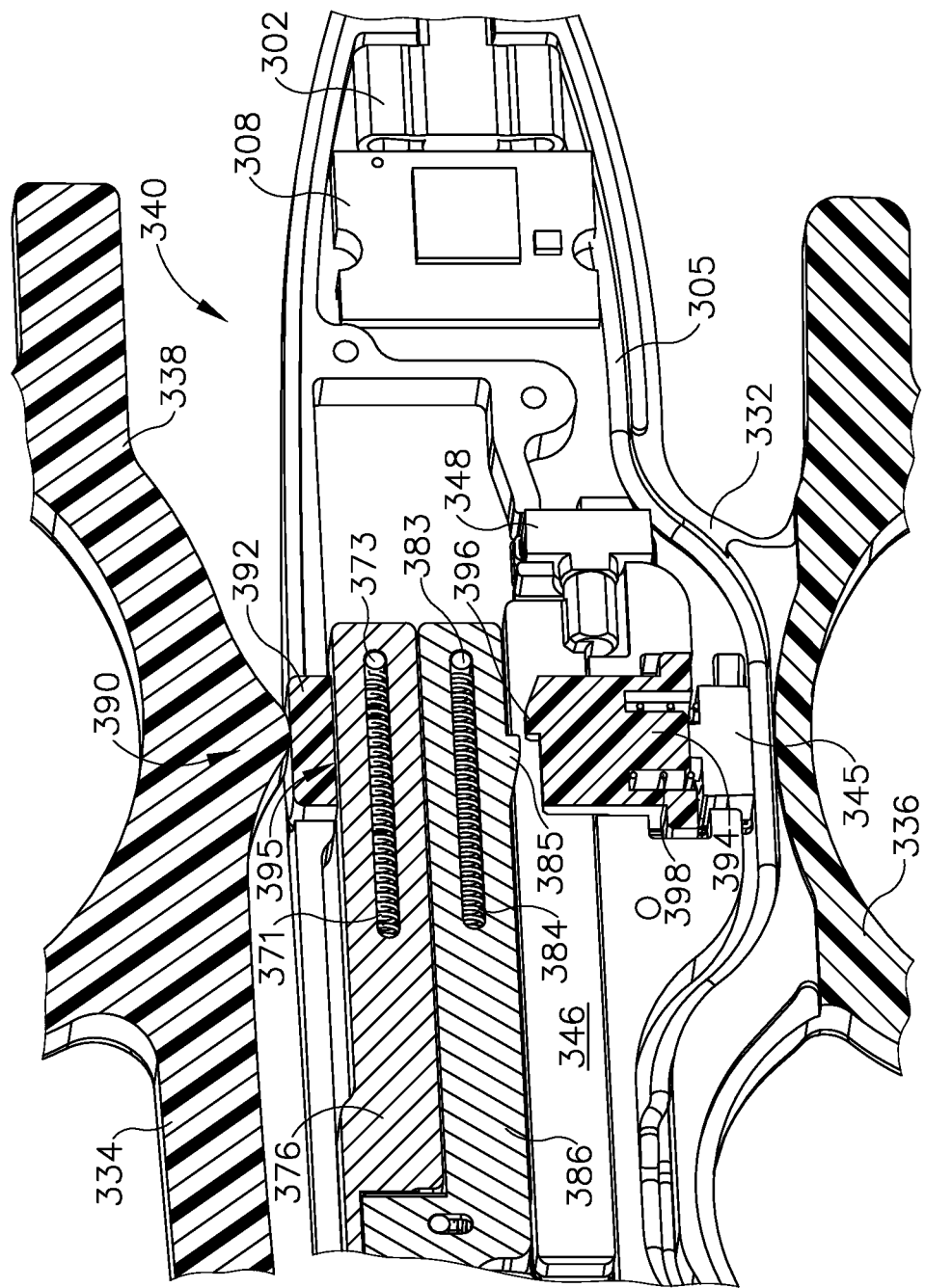
FIG. 26B depicts a cross-sectional view of a portion of the instrument of FIG. 17, taken along line 26-26 of FIG. 17, where the resilient arm is in a flexed position, where the lockout assembly of FIG. 19 is in an unlocked position, and where the firing assembly of FIG. 22 is in the pre-fired position.
Figure 26C:
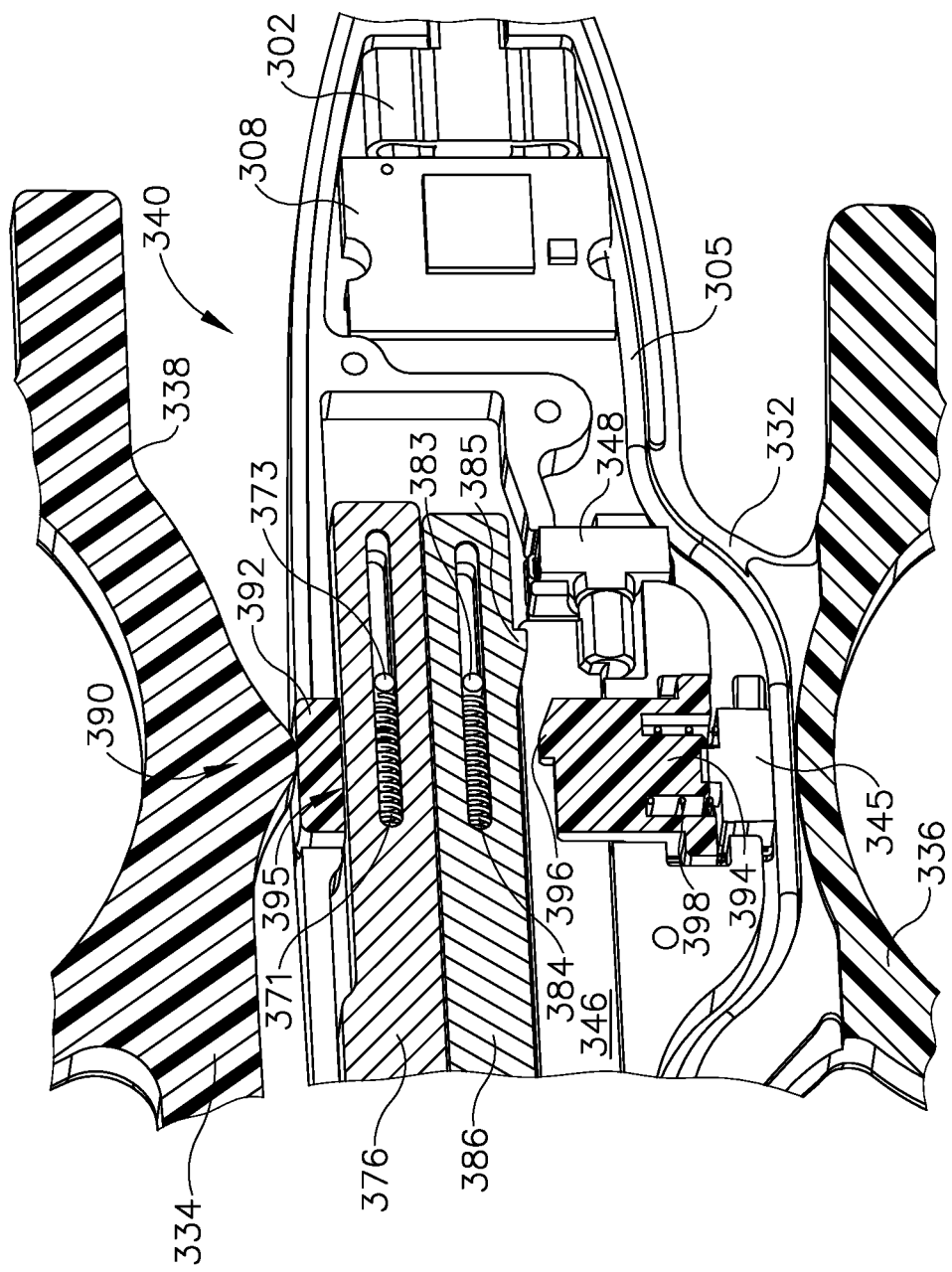
FIG. 26C depicts a cross-sectional view of a portion of the instrument of FIG. 17, taken along line 26-26 of FIG. 17, where the resilient arm is in the flexed position, where the lockout assembly of FIG. 19 is in the unlocked position, and where the firing assembly of FIG. 22 is in a fired position.

As best seen in FIGS. 21 and 26A, a portion of translating body (392) extends away from housing (332) toward thumb ring (338) while in the locked position. Thumb ring (338) of resilient arm (334) is dimensioned to abut against the portion of translating body (392) extending away from housing (332) when resilient arm (334) is in the flexed position, thereby driving lockout assembly (390) into the unlocked position. Thumb ring (338) does not abut against the portion of translating body (392) extending away from housing (332) when resilient arm (334) is in the relaxed position, such that spring (398) biases translating body (392) into the locked position.

As described above, the closure forces provided by jaws (312, 314) when resilient arm (334) is in the flexed position are suitable for electrodes (313, 315) to seal tissue via RF energy. Therefore, lockout assembly (390) is configured to move into the unlocked position when jaws (312, 314) provide a suitable closure force for electrodes (313, 315) to seal tissue via RF energy. Additionally, lockout assembly (390) is configured to move into the locked position when jaws (312, 314) do not provide a suitable closure force for electrodes (313, 315) to seal tissue via RF energy.

While in the unlocked position, button (394) depresses lockout button (345) of electrode activation assembly (340), thereby rendering lockout button (345) activated. Therefore, in the present example, if the operator presses RF trigger (342) while lockout assembly (390) is in the unlocked position, circuit board (308) would activate electrodes (313, 315) dues to both buttons (348, 345) being depressed. In other words, the operator is permitted to activate RF energy to electrodes (313, 315) when the closure forces provided by jaws (312, 314) are suitably conducive for sealing tissue via RF energy. In another example, lockout button (345) generates a signal send to control unit (104). An in yet another example, depressing lockout button (345) instructs circuit board (308) to activate electrode (313, 315).

Also, while in the unlocked position, lockout ledge (396) is spaced away from a proximal surface (385) of firing assembly (350) such that firing assembly (350) may actuate knife (320) in accordance with the description herein. Therefore, when lockout assembly (390) is in the unlocked position, the operator may both activate electrodes (313, 315) with RF energy, and actuate knife (320) distally to sever tissue grasped between jaws (312, 314). Lockout assembly (390) may indicate to the operator when lockout assembly (390) is in the unlocked configuration. For example, depressing button (345) may activate a suitable indicator as would be apparent to one having ordinary skill in the art in view of the teachings herein. For example, an LED may turn on, a instrument may emit noise, or a tactile response may be felt.

While in the locked position, button (394) is spaced away from lockout button (345) of electrode activation assembly (340), thereby rendering lockout button (345) un-activated. Therefore, in some versions where both lockout button (345) and activation button (338) must be depressed to activate electrodes (313, 315), if the operator presses RF trigger (342) while lockout assembly (390) is in the locked position, either accidentally or in an attempt to provide RF energy to electrodes (313, 315), circuit board (308) would not activate electrodes (313, 315) due to both buttons (348, 345) not being depressed. In other words, the operator is prevented from activating RF energy to electrodes (313, 315) when the closure forces provided by jaws (312, 314) are not suitably conducive for sealing tissue via RF energy.

Also, while in the locked position, lockout ledge (396) is directly adjacent to a proximal surface (385) of firing assembly (350), thereby preventing proximal translation of proximal surface (385) while body (292) is in the locked position. As will be described in greater detail below, proximal translation of proximal surface (385) drives distal translation of knife (320) in order to sever tissue. Since lockout ledge (396) prevents proximal translation of proximal surface (385) while lockout assembly (390) is in the locked position, lockout ledge (396) also prevents distal translation of knife (320) while lockout assembly (390) is in the locked position. In other words, when lockout assembly (390) is in the locked position, the operator may be prevented from activating electrodes (313, 315) with RF energy, as well as prevented from distally actuating knife (320) to sever tissue.

Through hole (395) is dimensioned to allow suitable portions of electrode activation assembly (340) and firing assembly (350) to actuate within through hole (395). In the current example, through hole (395) allows sliding body (346) of electrode activation assembly (340) to actuate within through hole (395) to access activation button (348). Additionally, through hole (395) is dimensioned to allow a portion of firing assembly (350) to actuate within through hole (350) while translating body (392) is in the unlocked position. In the current example, lockout ledge (396) is housed within a portion of body (392) defining through hole (395), however this is merely optional.

FIGS. 26A-26C show an exemplary use of lockout assembly (390). FIG. 26A shows resilient arm (334) pivoted toward housing (332) such that jaws (312, 314) are in the closed position while resilient arm (334) is in a relaxed position. Therefore, jaws (312, 314) may not provide a sufficient closing force suitable for electrodes (313, 315) to seal tissue grasped by jaws (312, 314). Additionally, thumb ring (338) does not abut against translating body (392) such that spring (398) biases translating body (392) to the locked position. As mentioned above, since translating body (392) is in the locked position, the operator may not distally actuate knife (320) or provide RF energy to electrodes (313, 315) in accordance with the description herein.

Next, as seen in FIG. 26B, the operator may pivot resilient arm further toward housing (332) such that resilient arm bends to the flexed position. Additionally, thumb ring (338) abuts against translating body (392), overcoming the biasing force provided by spring (398), such that translating body (392) is in the unlocked position. At this point, the closure forces provided by jaws (312, 314) are sufficiently suitably for electrodes (313, 315) to seal tissue grasped by jaws (312, 314). At this point, lockout button (345) is depressed such that lockout button (345) is activated in accordance with the teachings herein. Additionally, as seen in FIG. 26C, while translating body (392) is in the unlocked position, and operator may actuate trigger (351) of firing assembly (350) such that knife (320) translates distally through elongate slot (316) to sever tissue grasped by jaws (312, 314) in accordance with the teachings herein. Because lockout ledge (396) no longer interferes with proximal translation of proximal surface (385), firing assembly (350) may actuate knife (320) distally. It should be understood that when the operator no longer presses resilient arm (334) toward housing (332) with enough force to keep arm (334) in the flexed position, the resilient nature of arm (334) will return arm (334) to the relaxed position, allowing spring (398) to bias translating body (392) back into the locked position.

As mentioned above, firing assembly (350) is configured to convert proximal translation of trigger (351) into distal translation of knife (320). As also mentioned above, a portion of firing assembly (350) and handle assembly (330) form an automatic knife return mechanism configured to automatically drive knife (320) to a pre-fired position after knife (320) reaches a predetermined distal position. Firing assembly (350) includes an input drive assembly (370), a rotary drive assembly (352), and an output drive assembly, such as a proximal body (326) unitarily coupled with knife (320) and a transverse pin (328) extending laterally from proximal body (326).

As will be described in greater detail below, trigger (351) is configured to actuate input drive assembly (370) proximally such that rotary driver assembly (352) actuates proximal body (326) and knife (220) distally. It should be understood that sliding body (346) of electrode activation assembly (340) may slide independently relative to firing assembly (350). Therefore, the operator may activate electrodes (313, 315) independently of firing assembly (350) and knife (320), in accordance with the description herein.

Input drive assembly (370) includes a first sliding member (372) and a second sliding member (380). Both sliding members (372, 380) are slidably contained within housing (332). As will be described in greater detail below, first sliding member (372) is configured to proximally drive second sliding member (380), while second sliding member (380) is configured to actuate rotary drive assembly (352).

Figure 22:
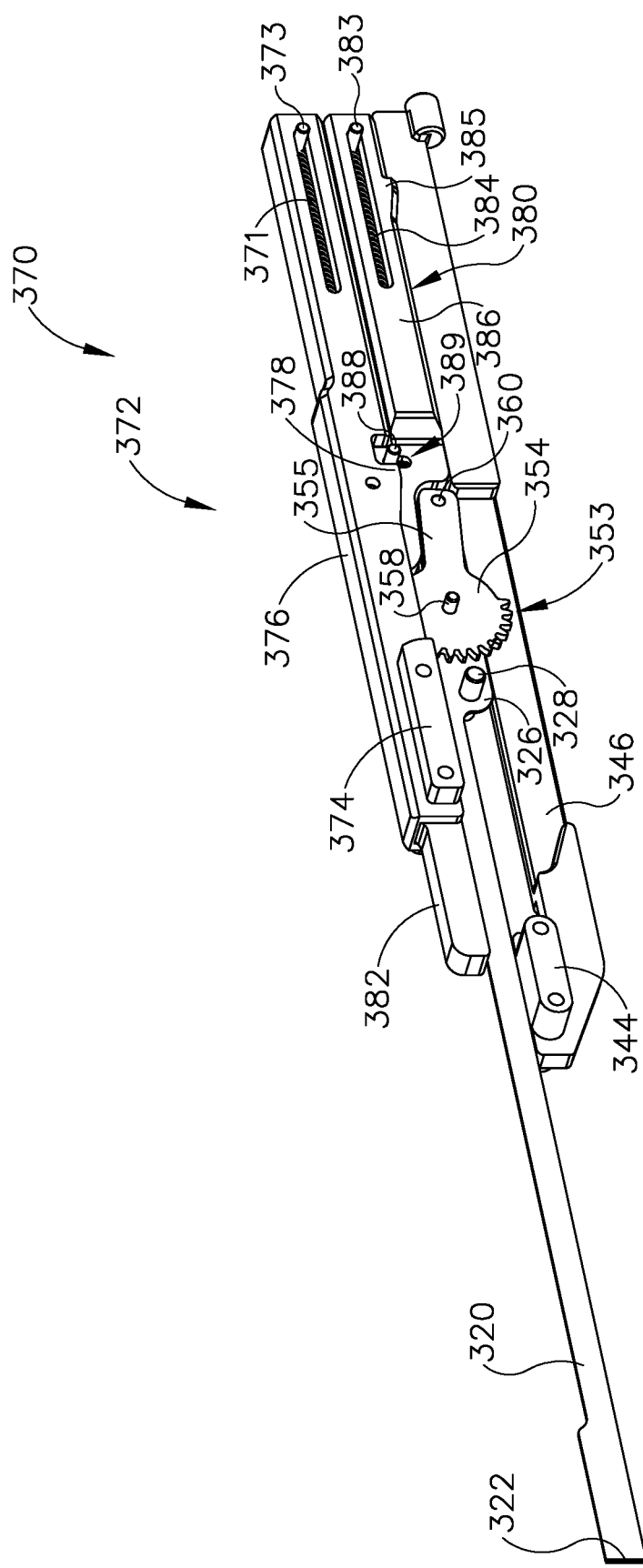
FIG. 22 depicts a perspective view of a firing assembly of the electrosurgical forceps instrument of FIG. 17.
Figure 23:
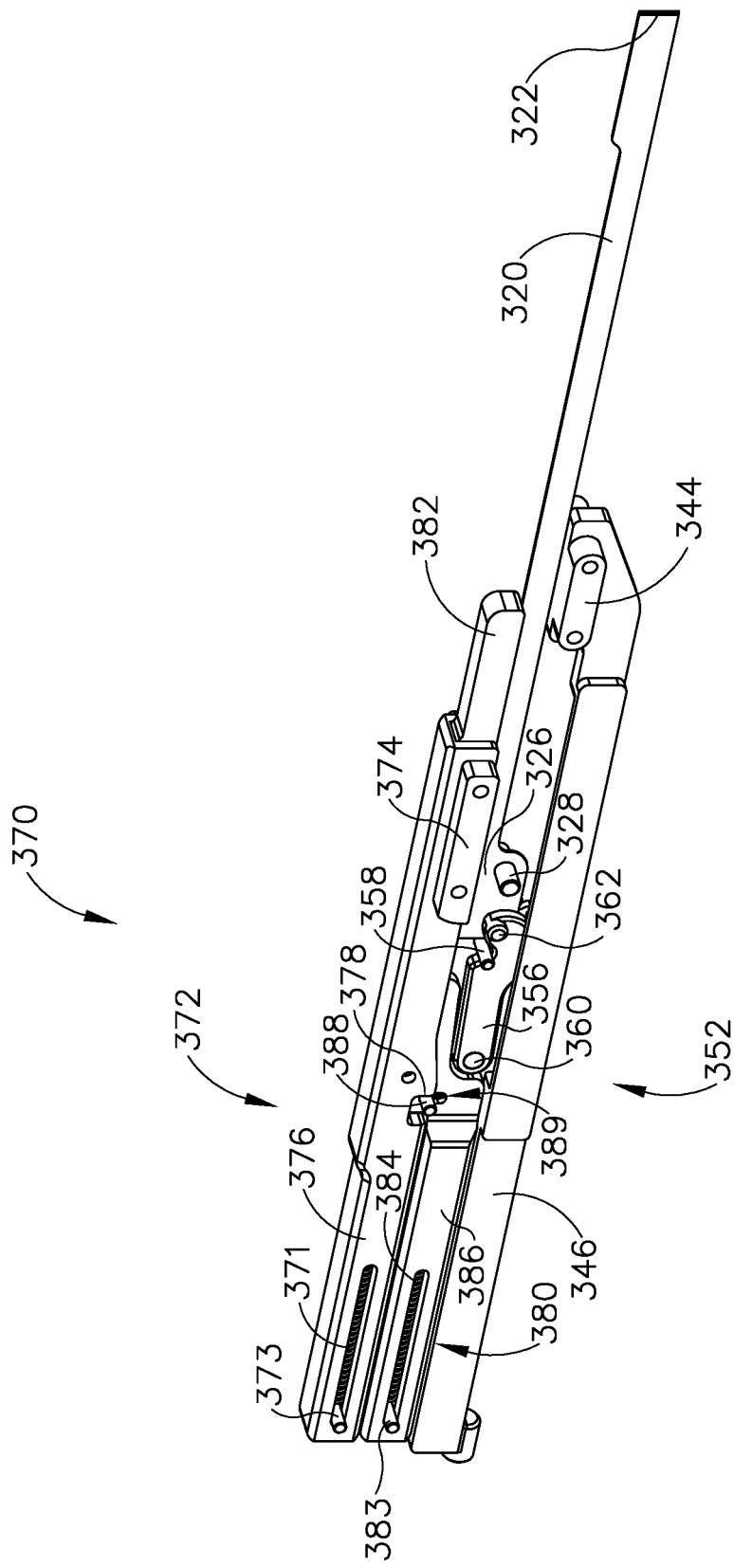
FIG. 23 depicts another perspective view of the firing assembly of FIG. 22.
Figure 24:
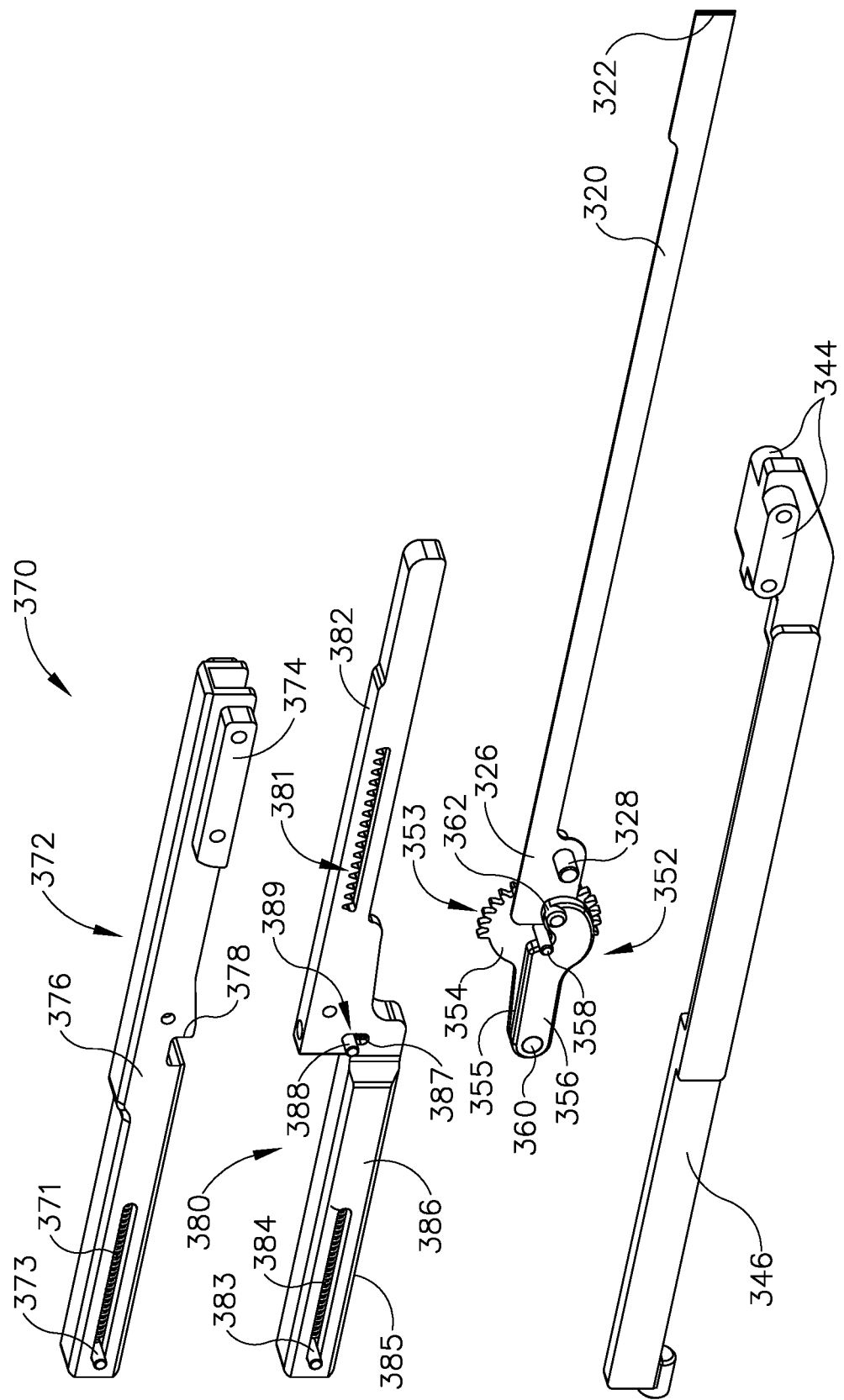
FIG. 24 depicts an exploded perspective view of the firing assembly of FIG. 22.

As best seen in FIGS. 22-24, first sliding member (372) includes a coupling block (374), a sliding body (376), a pair of laterally spaced projections (378), a grounding pin (373), and a biasing member (371) disposed within the confines of sliding body (376) and against grounding pin (373). Coupling block (374) is fixed relative to sliding body (376). Coupling block (374) is configured to couple with trigger (351) when instrument (300) is assembled such that actuation of trigger (351) relative to housing (332) drives actuation of coupling block (374) and sliding body (376) relative to housing (332). As will be described in greater detail below, projections (378) are dimensioned to drive portions of second sliding member (380) proximally in response to proximal translation of first sliding member (372).

Grounding pin (373) is fixed to housing (332) when instrument (300) is assembled such that as sliding body (376) translates, grounding pin (373) remains spatially fixed relative to housing (332). Biasing member (371) abuts against grounding pin (373) and sliding body (376) in order to bias sliding body (376) to a distal, pre-fired position. Therefore, if the operator actuates trigger (351) proximally, biasing member (371) compresses such that when the operator releases trigger (351), biasing member (371) actuates trigger (351) to the distal, pre-fired, position. In the current example, biasing member (371) includes a spring, but any other suitably biasing member (371) may be used as would be apparent to one having ordinary skill in the art in view of the teachings herein.

Second sliding member (380) includes a distal rack (382), a sliding body (386), a proximal surface (385), a grounding pin (383), a biasing member (384) disposed within the confines of sliding body (386), a transverse driving pin (388), and a second biasing member (387). Proximal surface (385) is configured to engage lockout assembly (390) is accordance with the teachings above. Distal rack (382) includes plurality of teeth (381). As will be described in greater detail below, teeth (381) are configured to mesh with portions of rotary drive assembly (352) such that translation of rack (382) rotates rotary drive assembly (352).

Grounding pin (383) is fixed to housing (332) when instrument (300) is assembled such that as sliding body (386) translates, grounding pin (383) remains spatially fixed relative to housing (332). Biasing member (384) abuts against grounding pin (383) and sliding body (386) in order to bias sliding body (386) to a distal, pre-fired position.

Sliding body (386) defines a slot (389) that slidably houses transverse driving pin (388). Second biasing member (387) biases transverse driving pin (388) to an upward position within slot (389). Transverse driving pin (388) may actuate within slot (389) to overcome the biasing force of second biasing member (387). Transverse driving pin (388) is dimensioned to abut against projections (378) of first sliding member (372) when in the upward position. Therefore, if the operator actuates trigger (351) proximally, first sliding member (372) may proximally drive second sliding member (380) via projection (378) and transverse driving pin (388). Additionally, as best shown in FIGS. 16A-16F, transverse driving pin (388) is housed within a slotted pathway (331) defined by the interior of housing (332). Therefore, as projections (378) drive transverse driving pin (388), a portion of pin (388) is within slotted pathway (331). As will be described in greater detail below, once first and second sliding members (372, 380) proximally translate a predetermined distance, transverse driving pin (388) may actuate within slot (389), due to contact with a cam surface (333) of slotted pathway (331), such that transverse driving pin (388) no longer engages projections (378). Therefore, with projections (378) no longer engaging driving pin (388), first biasing member (384) may distally drive sliding body (386) and rack (382) back to the distal, pre-fired position, which in turn may rotate rotary drive assembly (352).

Figure 25:
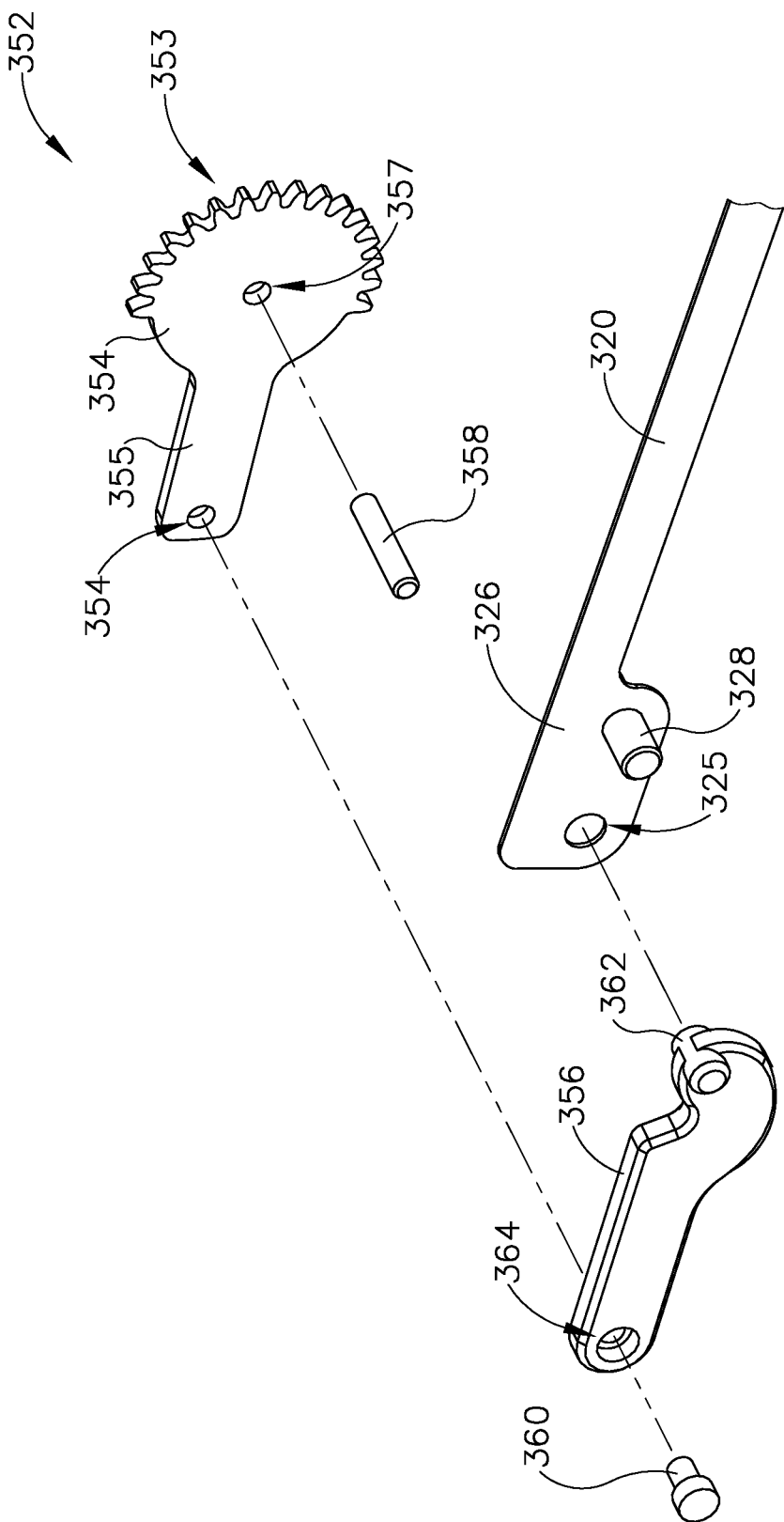
FIG. 25 depicts an exploded perspective view of a rotary drive assembly of the firing assembly of FIG. 22.

As best seen in FIG. 25, rotary drive assembly (352) includes a rotary gear (354), and a link (356). Rotary gear (354) includes a plurality of teeth (353), and an arm (355). A central portion of rotary gear (354) defines a through hole (357) while a terminating portion of arm (355) also defines a through hole (359). Rotary gear (354) is rotatably coupled with housing (332) via pin (358) and through hole (359). Therefore, rotary gear (354) may rotate about pin (358) but is otherwise fixed relative to housing (332). As will be described in greater detail below, rotary gear (354) is configured to rotate in response to translation of distal rack (382) via meshing of teeth (353, 381).

Link (356) defines a though hole (364) near one end of link (356). Additionally, link includes a lateral projection (362) near the opposite end of link (356) defining through hole (364). Link (356) is pivotably coupled to both arm (355) of rotary gear (354) and proximal body (326) of knife (320). Link (356) is pivotably coupled to arm (355) via through holes (364, 259) and a rotary pin (360). Link is pivotably coupled with proximal body (326) of knife (320) via lateral projection (362) and a pin hole (325) defined by proximal body (326).

As mentioned above, proximal body (326) of knife (320) includes a transverse pin (328). As best seen in FIGS. 27A-27G, transverse pin (328) is slidably constrained within a second slotted pathway (337) of housing (332). Therefore, proximal body (326) must translate along the path defined by second slotted pathway (337). Since lateral projection (362) of link (356) is pivotably coupled with proximal body (326) of knife (320), lateral projection (362) is also constrained to translate along the path defined by second slotted pathway (337). As will be described in greater detail below, because link (356) is rotatably coupled to arm (355) and proximal body (326) at separate ends of link (354), and because lateral projection (362) is constrained to translate along the path defined by second slotted pathway (337), rotation of rotary gear (354) is configured to actuate proximal body (326) and knife (320) along the path defined by second slotted pathway (337). Additionally, the use of link (356) and arm (355) to longitudinally drive body (326) of knife (320) may cause a knife (320) to travel a greater distance distally than the distance traveled by rack (382) proximally. This may help reduce the size of handle assembly (330).

Figure 27A:
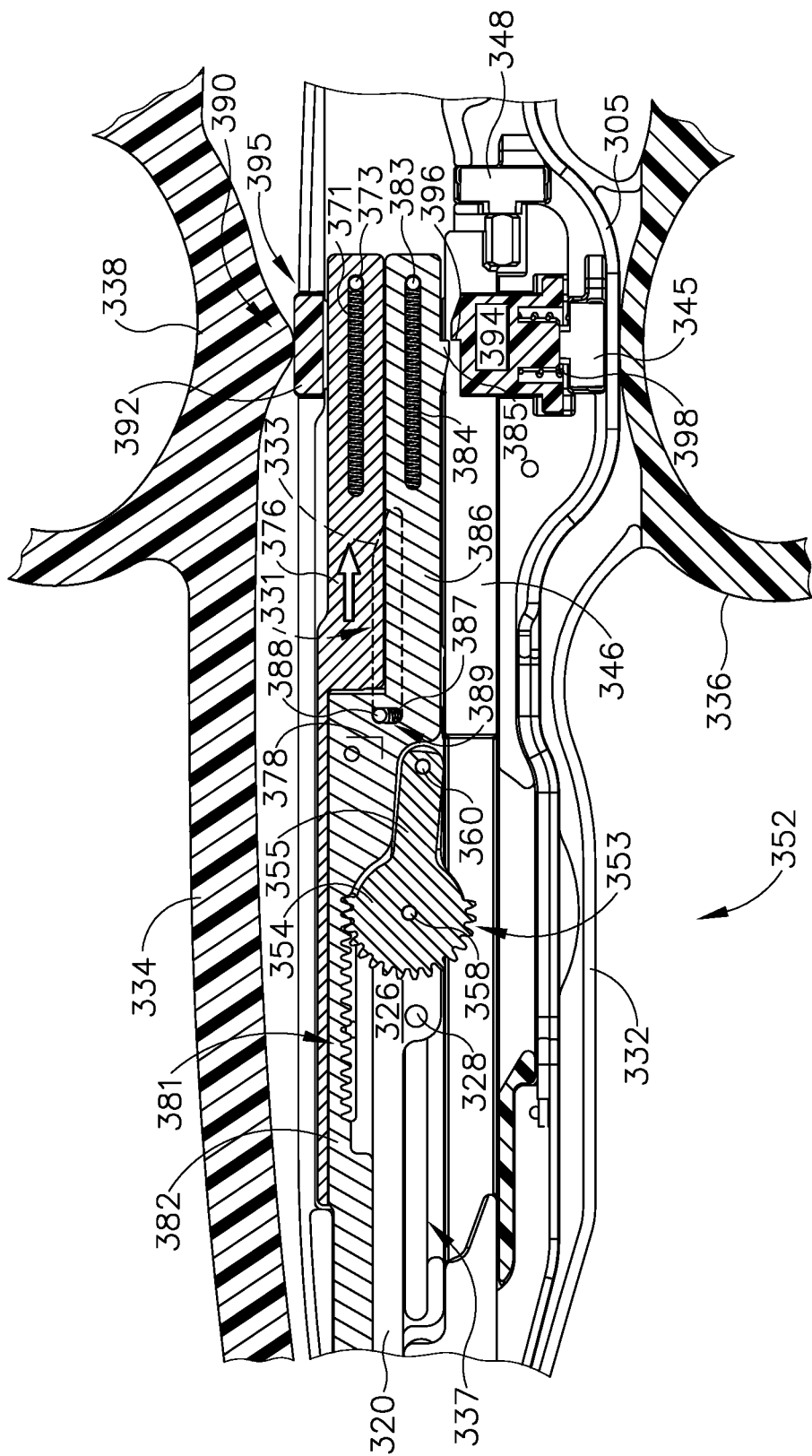
FIG. 27A depicts a side elevational view of a portion of the instrument of FIG. 17, with a portion of the handle assembly of FIG. 18 omitted for clarity, where firing assembly is in a first pre-fired position.

FIGS. 27A-27G show an exemplary use of firing assembly (350) to actuate knife (320) through jaws (312, 314) to sever tissue. FIG. 27A shows firing assembly (350) in the pre-fired position whiles jaws (312, 314) are in the closed position and resilient arm is in the flexed position. Therefore, lockout assembly (390) is in the unlocked position, and knife (320) is in a pre-fired position similar to that shown of knife (120) in FIG. 4A. When the operator desires to fire knife (320) distally within jaws (312, 314), the operator may pull trigger (351) proximally. As shown between FIGS. 27A-27B, while pulling trigger (351) proximally, first sliding member (372) may actuate proximally independently of second sliding member (380) until projections (378) make contact with transverse driving pin (388).

Figure 27B:
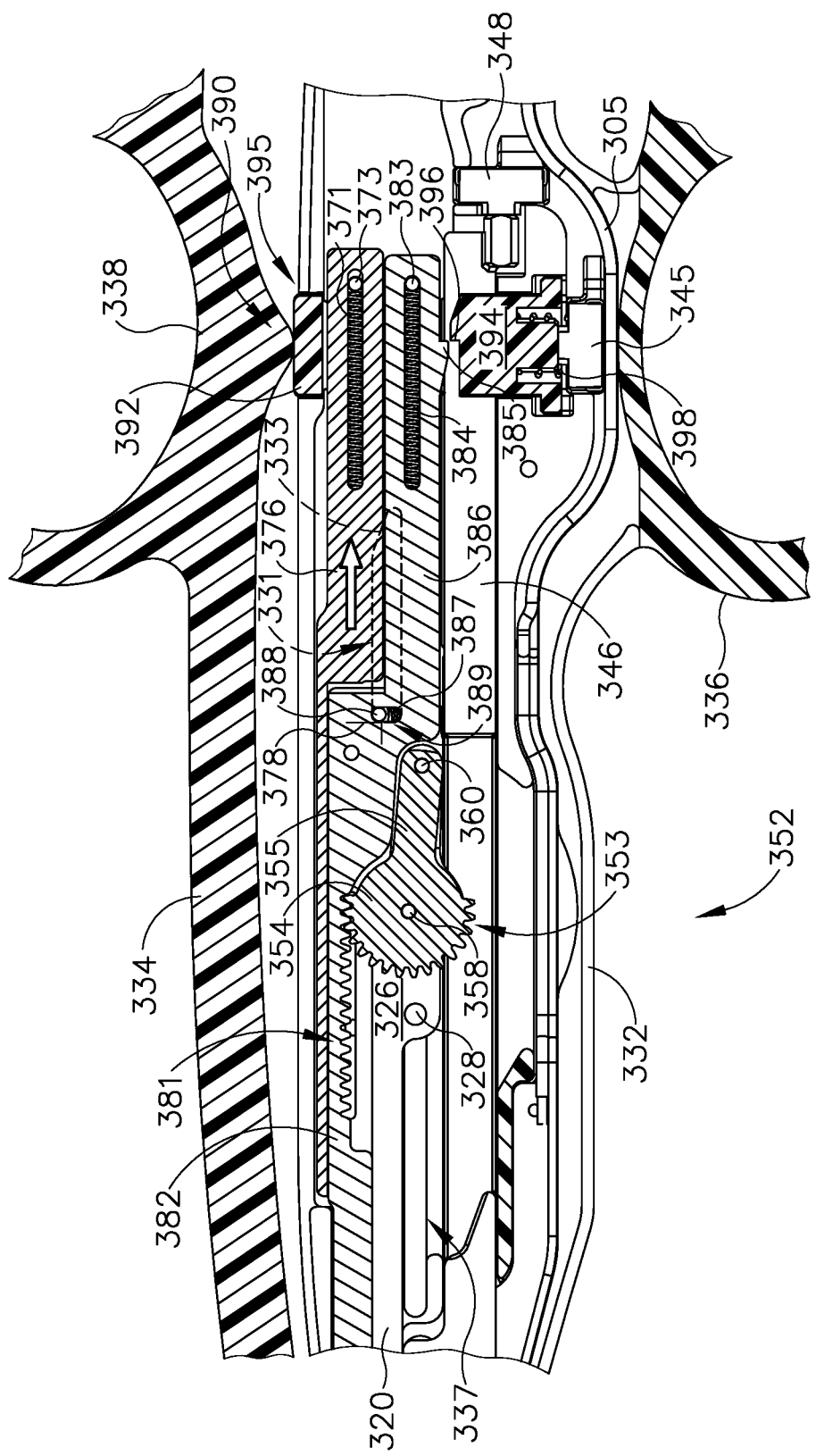
FIG. 27B depicts a side elevation view of a portion of the instrument of FIG. 17, with a portion of the handle assembly of FIG. 18 omitted for clarity, where the firing assembly is in a second pre-fired position.
Figure 27C:
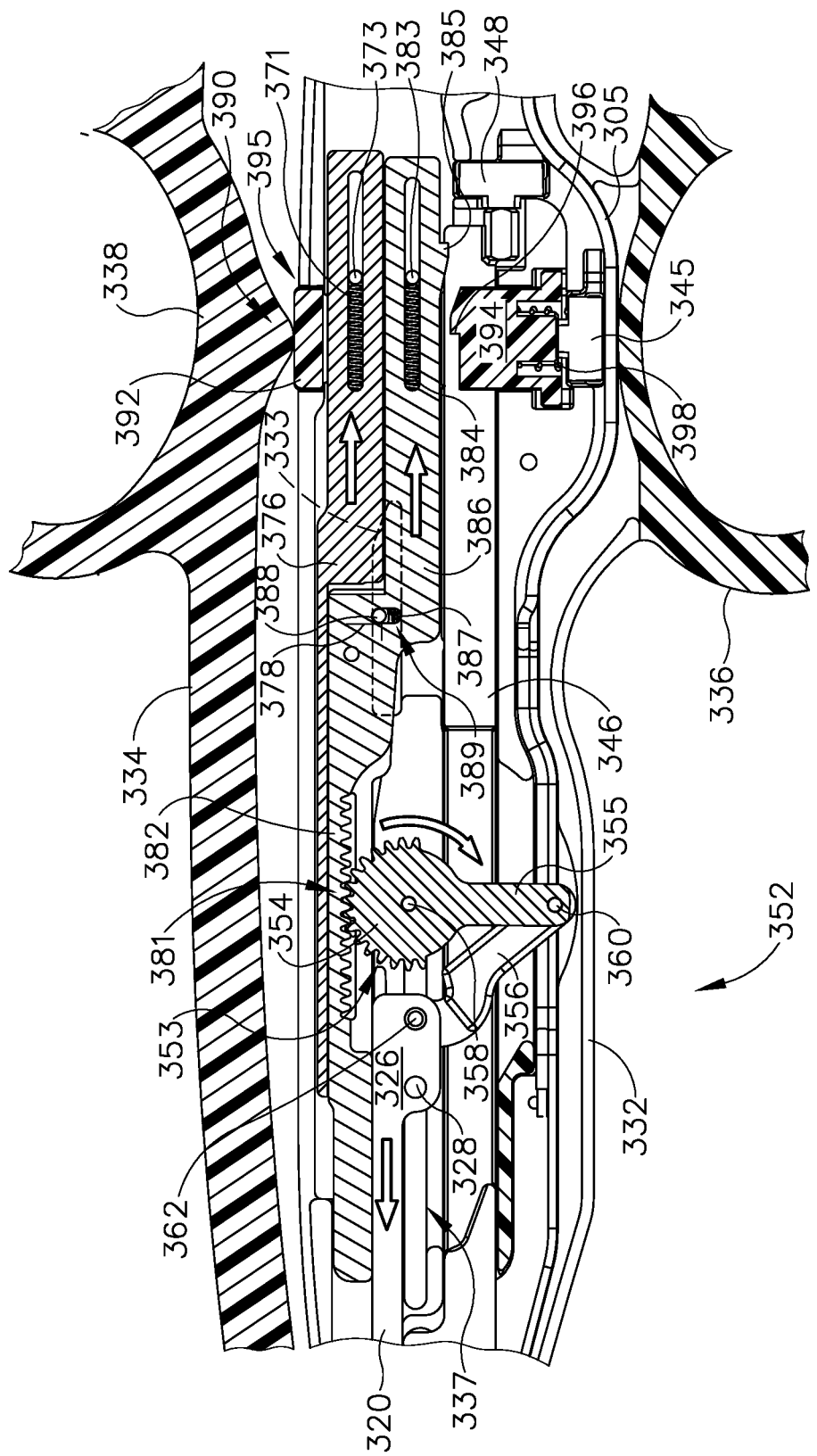
FIG. 27C depicts a side elevation view of a portion of the instrument of FIG. 17, with a portion of the handle assembly of FIG. 18 omitted for clarity, where the firing assembly is in a first fired position.
Figure 27D:
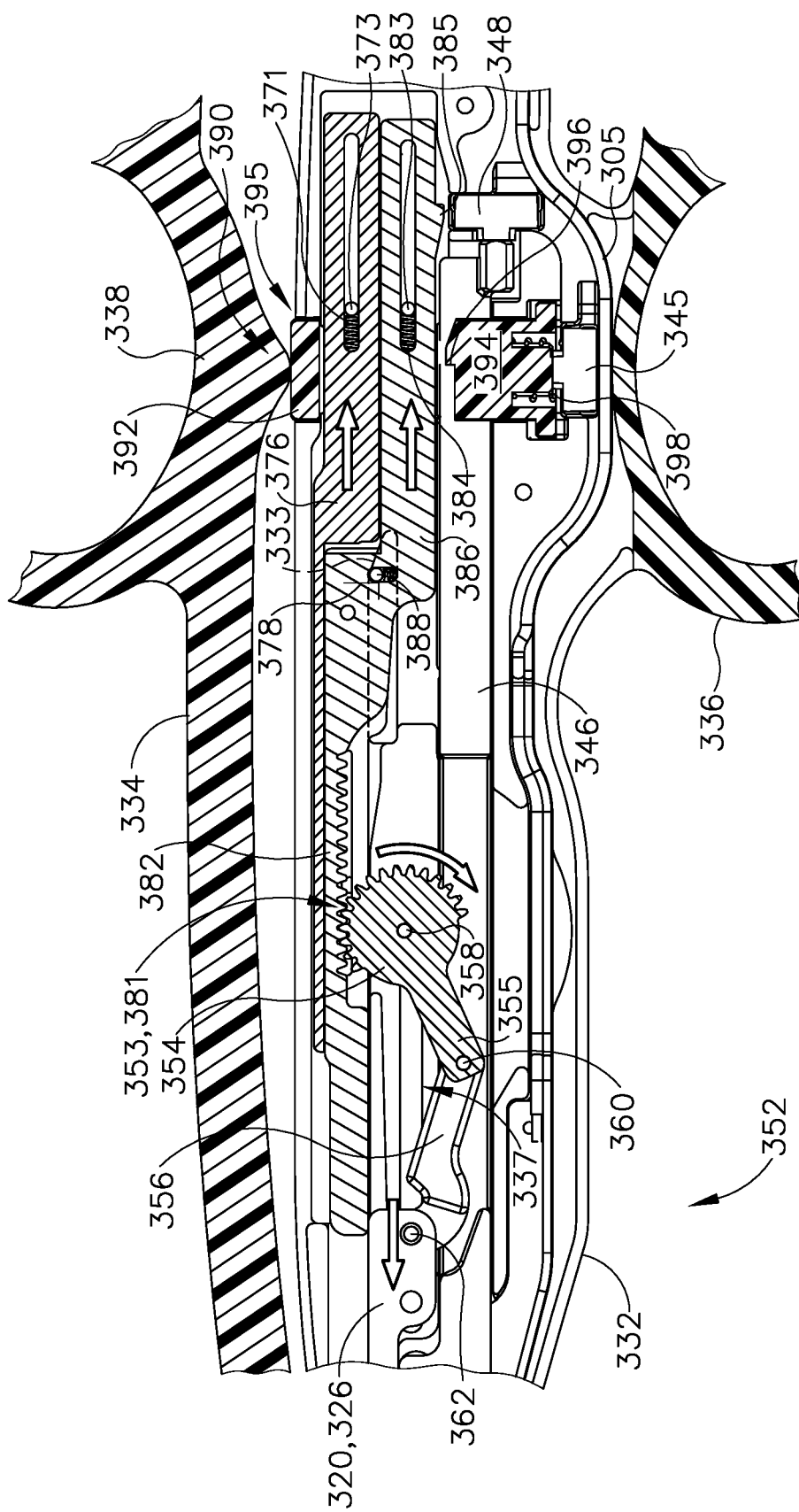
FIG. 27D depicts a side elevation view of a portion of the instrument of FIG. 17, with a portion of the handle assembly of FIG. 18 omitted for clarity, where the firing assembly is in a second fired position.

Next, as shown between FIGS. 27B-27D, the operator may further pull trigger (351) proximally such that first sliding member (372) and second sliding member (380) move proximally together due to projection (378) making contact with transverse driving pin (388). Proximal movement of second sliding member (380) causes rack (382) of second sliding member (380) to rotate rotary gear (354) about pin (358) in a first angular direction, which in turn causes link (356) to rotate about lateral projection (362) in a second, opposite, angular direction. Additionally, because lateral projection (362) is pivotably coupled to proximal body (326), and because proximal body (326) is constrained within second slotted pathway (237), rotation of link (356) about lateral projection (362) in the second angular direction also distally drives proximal body (326) of knife (320). At the moment shown in FIG. 27D, knife (320) may have actuated substantially through jaws (312, 314), severing tissue captured between jaws (312, 314), similar to the position shown of knife (120) in FIG. 4B.

Figure 27E:
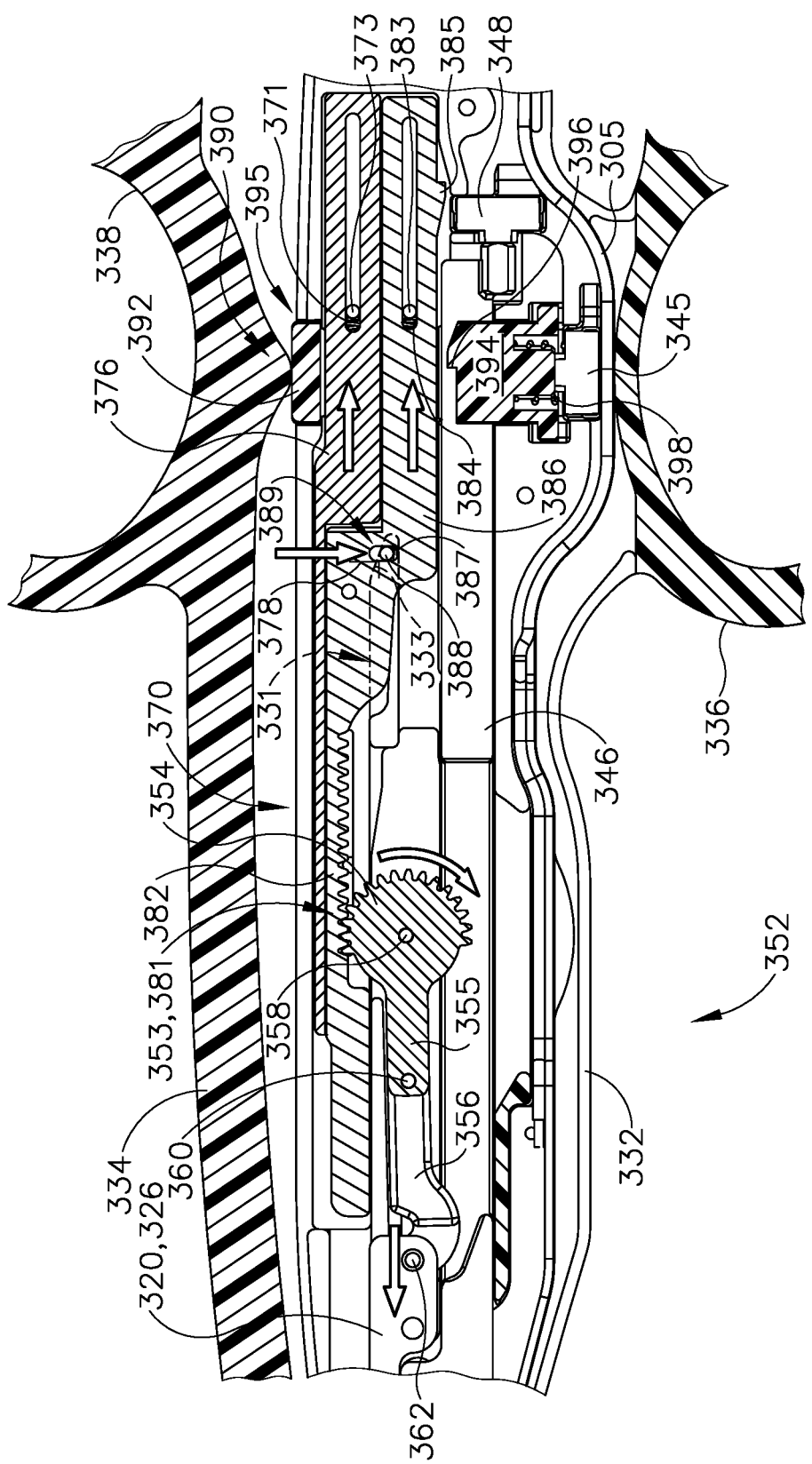
FIG. 27E depicts a side elevation view of a portion of the instrument of FIG. 17, with a portion of the handle assembly of FIG. 18 omitted for clarity, where the firing assembly is in a third fired position.

Because grounding pins (373, 383) are fixed relative to housing (332), movement of sliding bodies (376, 386) compresses biasing members (371, 384) between grounding pins (373, 383) and the interior of sliding bodies (376, 386), respectively. As mentioned above, transverse driving pin (388) is partially housed within slotted pathway (331) defined within housing (332). FIG. 27D shows transverse driving pin (388) at a position just distal to cam surface (333) of slotted pathway (331). If the operator pulls trigger (351) further in the proximal direction, as shown in FIG. 27E, transverse driving pin (388) will come into contact with cam surface (333) of slotted pathway (331). Cam surface (333) will push transverse driving pin (388) downwards within slot (389) overcoming the biasing force of second biasing member (387).

Figure 27F:
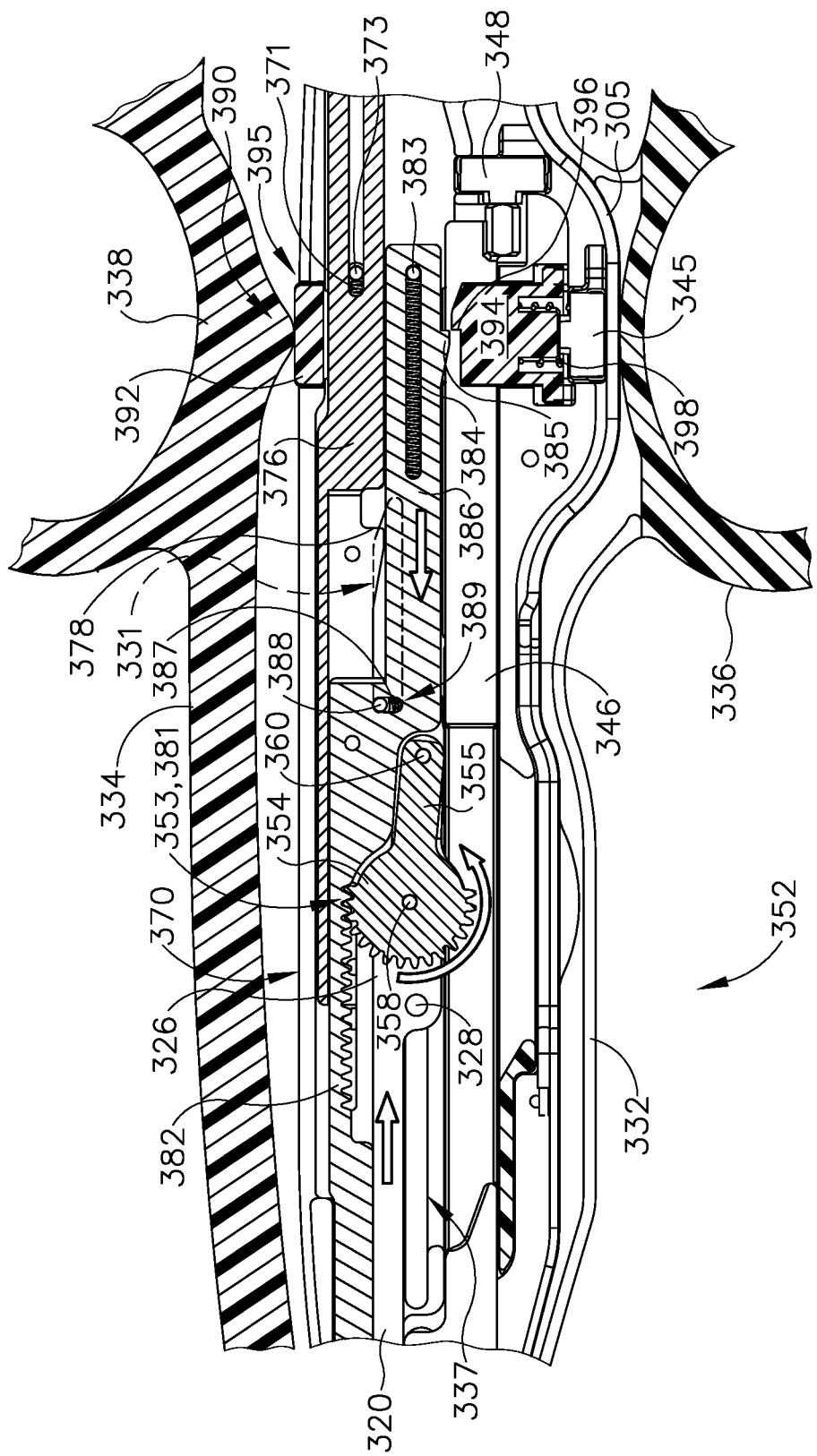
FIG. 27F depicts a side elevation view of a portion of the instrument of FIG. 17, with a portion of the handle assembly of FIG. 18 omitted for clarity, where the firing assembly is in a pre-returned, post-fired position.

As also shown in FIG. 27E, cam surface (333) may push transverse driving pin (388) downwards until pin (388) is no longer engaged with projections (378). With pin (388) no longer engaged with projections (378), first biasing member (384) may push against grounding pin (383), therefore actuating second sliding member (380) in the distal direction, as shown in FIG. 27F. Actuation of second sliding member (380) rotates rotary gear (354) about pin (358) in the second angular direction, which in turn causes link (356) to rotate about lateral projection (362) in the first angular direction such that proximal body (326) is retracted proximally within second slotted pathway (337). In particular, knife (320) may travel all the way back to the pre-fired position. Once actuated proximally past cam surface (333), biasing member (387) may bias transverse pin (388) back within slot (389). Projections (378) may also interact with transverse driving pin (388) and second biasing member (387) such that projections (378) may push pin (388) downward out of engagement with projections (378) when knife (320) experiences an excess load, such as when knife (320) encounters an undesirable object. For example, if knife (330) encounters an object difficult to cut, projections (378) may overcome the biasing force of second biasing member (387) such that transverse driving pin (388) actuates downward within slot (389). In other words, if knife (320) encounters an object too difficult to cut, contact between projections (338) and transverse driving pin (388) may generate a force the actuates pin (388) within slot (389) such that pin (388) and projection (378) are no longer in engagement, instead of proximally driving second sliding member (380). Therefore, second sliding member (380) decouples with first sliding member (372) prior to knife (320) reaching the fired position, and knife (320) automatically travels back to the pre-fired position due to first biasing member (384) driving sliding body (386) distally. This may help prevent knife (320) from being damaged.

It should be understood that second sliding member (380) returns to the pre-fired position even though first sliding member (372) is still in the fired position. Therefore, once the operator pulls trigger (253) far enough proximally to complete the distal actuation of knife (320), second sliding member (380) may disengage with first sliding member (372) and automatically return knife (320) to the pre-fired position, regardless if the operator holds trigger (351) in the proximal position. In other words, cam surface (333) of slotted pathway (331), transverse pin (388), and biasing members (384, 387) may act as an automatic knife return mechanism to return knife (320) to the pre-fired poison automatically after reaching a predetermined distal location.

Figure 27G:
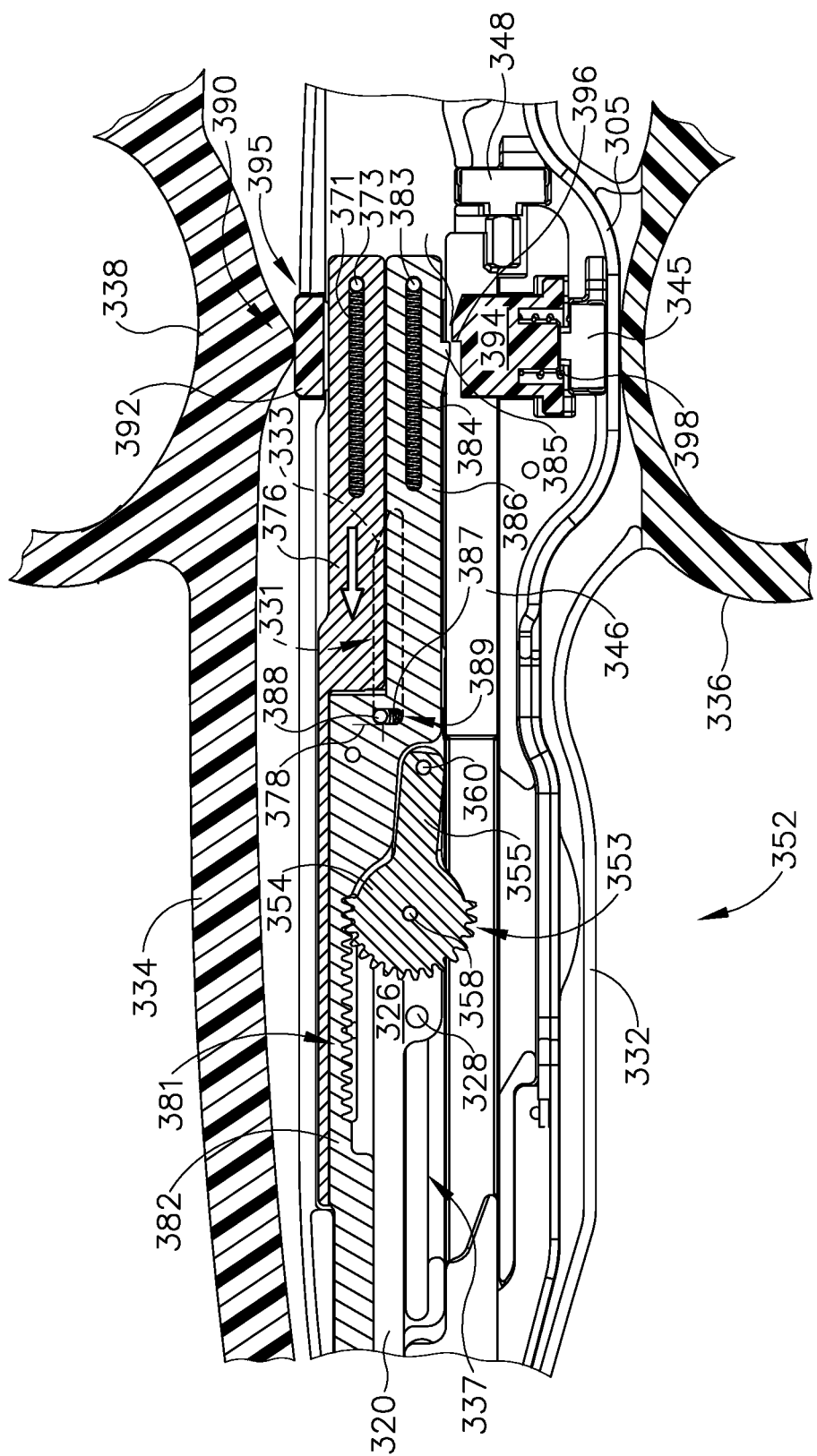
FIG. 27G depicts a side elevational view of a portion of the instrument of FIG. 17, with a portion of the handle assembly of FIG. 18 omitted for clarity, where the firing assembly is fully returned to the first pre-fired position.

As shown between FIGS. 27F-27G, the operator may release trigger (351) such that biasing member (371) pushes first sliding member (372) back to the position shown in FIG. 27A. The operator may then re-fire knife (320) in accordance with the description herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to transition between an open position and a closed position, (iii) a knife configured to actuate between a pre-fired position to a fired position, and (iv) an electrode assembly configured to apply RF energy to tissue; (b) a handle assembly, wherein the handle assembly comprises: (i) a housing associated with the first jaw, (ii) an arm associated with the second jaw, wherein the arm is pivotably coupled with the housing, wherein the arm is configured to pivot the second jaw between the open position and the closed position; (c) a knife drive assembly configured to actuate the knife between the pre-fired position and the fired position; (d) an electrode activation assembly configured to activate the electrode assembly; and (e) a lockout assembly configured to transition between a locked configuration and an unlocked configuration, wherein the lockout assembly is configured to prevent activation of the electrode and prevent actuation of the knife drive assembly while in the locked configuration, wherein the lockout assembly is configured to allow activation of the electrode and allow actuation of the knife drive assembly while in the unlocked configuration.

Example 2

The surgical instrument of Example 1, wherein the arm comprises a resilient member configured to transition between a relaxed configuration and a flexed configuration while the second jaw is in the closed position.

Example 3

The surgical instrument of Example 2, wherein the arm is configured to drive the lockout assembly into the unlocked configuration when the resilient member is in the flexed configuration.

Example 4

The surgical instrument of any one or more of Examples 1 through 3, wherein the lockout assembly comprises a translating body resiliently biased toward the locked configuration.

Example 5

The surgical instrument of Example 4, wherein the electrode activation assembly comprises an activation button and a lockout button, wherein the electrode activation assembly is configured to activate the electrode assembly only when both the activation button and the lockout button are activated.

Example 6

The surgical instrument of Example 5, wherein the translating body of the lockout assembly is configured to activate the lockout button while in the unlocked configuration.

Example 7

The surgical instrument of Example 6, wherein the electrode activation assembly comprises a sliding body configured to activate the activation button.

Example 8

The surgical instrument of Example 7, wherein the sliding body is biased to not activate the activation button.

Example 9

The surgical instrument of any one or more of Examples 6 through 8, wherein the electrode activation assembly comprises a circuit board.

Example 10

The surgical instrument Example 9, wherein the activation button is in communication with the circuit board.

Example 11

The surgical instrument of Example 10, wherein the lockout button is in communication with the circuit board.

Example 12

The surgical instrument of any one or more of Examples 10 through 11, wherein the lockout button acts as a switch for the activation button.

Example 13

The surgical instrument of any one or more of Examples 4 through 12, wherein the translating body comprises a lockout ledge configured to abut against a portion of the knife drive assembly in the locked configuration.

Example 14

The surgical instrument of Example 13, wherein the knife drive assembly comprises a proximal presented surface configured to abut against the lockout ledge while the translating body is in the locked configuration and the knife is in the pre-fired position.

Example 15

The surgical instrument of any one or more of Examples 4 through 14, wherein the translating body defines a through hole configured to receive a portion of the electrode activation assembly.

Example 16

The surgical instrument of Example 15, wherein the through hole is configured to receive a portion of the knife drive assembly.

Example 17

A surgical instrument comprising: (a) a housing extending distally into a first jaw; (b) an arm pivotably coupled with the housing, wherein the arm extends distally into a second jaw, wherein the arm is operable to drive the second jaw between an open position and a closed position; (c) an electrode associated with the first jaw or the second jaw, wherein the electrode is configured to apply RF energy to tissue; (d) a knife configured to actuate within the first jaw and the second jaw between a pre-fired position and a fired position; (e) an electrode activation assembly configured to activate the electrode, (f) an indicator assembly configured to generate a signal in response to the arm moving to a first position associated with the second jaw in the closed position; (g) a knife actuation assembly configured to actuate the knife between the pre-fired position and the fired position; and (h) a lockout assembly configured to prevent actuation of the knife actuation assembly when the arm is in the first position.

Example 18

The surgical instrument of Example 17, wherein the knife actuation assembly comprises a rotary gear and a link, wherein the rotary gear is pivotably coupled with the housing, wherein the link is pivotably coupled with the knife and the rotary gear.

Example 19

The surgical instrument of any one or more of Examples 17 through 18, wherein the electrode activation assembly comprises an activation button, wherein the electrode activation assembly is configured to activate the electrode only if both the activation button is depressed and the indicator assembly has generated the signal.

Example 20

A surgical instrument comprising: (a) a housing extending distally into a first jaw; (b) an arm pivotably coupled with the housing, wherein the arm extends distally into a second jaw, wherein the arm is operable to drive the second jaw between an open position and a closed position; (c) an electrode associated with the first jaw or the second jaw, wherein the electrode is configured to apply RF energy to tissue; (d) a knife configured to actuate within the first jaw and the second jaw between a pre-fired position and a fired position; (e) an electrode activation assembly configured to activate the electrode in response to the arm actuating to a first position while the second jaw is in the closed position; (f) a knife actuation assembly configured to actuate the knife between the pre-fire position and the fired position; and (g) a lockout assembly configured to prevent actuation of the knife actuation assembly when the resilient arm is in the relaxed state, wherein the lockout assembly is configured to allow actuation of the knife actuation assembly when the resilient arm is in the flexed state.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. App. Ser. No. 15/989,424, entitled "Method and Apparatus for Open Electrosurgical Shears," filed on Mar. 25, 2018, published as U.S. Pub. No. 2019/0357962 on Nov. 28, 2019; U.S. App. Ser. No. 15/989,433, entitled "Knife Drive Assembly for Electrosurgical Shears," filed on Mar. 25, 2018, published as U.S. Pub. No. 2019/0357963 on Nov. 28, 2019; U.S. App. Ser. No. 15/989,438, entitled "Knife Auto-Return Assembly for Electrosurgical Shears," filed on Mar. 25, 2018, issued as U.S. Pat. No. 10,898,259 on Jan. 26, 2021; U.S. App. Ser. No. 15/989,442, entitled "Compound Screw Knife Drive for Electrosurgical Shears," filed on Mar. 25, 2018, issued as U.S. Pat. No. 10,856,931 on Dec. 8, 2020; U.S. App. Ser. No. 15/989,448, entitled "Firing and Lockout Assembly for Knife for Electrosurgical Shears," filed on Mar. 25, 2018, published as U.S. Pub. No. 2019/0357966 on Nov. 28, 2019; U.S. App. Ser. No. 15/989,452, entitled "Dual Stage Energy Activation for Electrosurgical Shears," filed on Mar. 25, 2018, published as U.S. Pub. No. 2019/0357967 on Nov. 28, 2019; and U.S. App. Ser. No. 15/989,455, entitled "Latching Clamp Arm for Electrosurgical Shears," filed on Mar. 25, 2018, published as U.S. Pat. No. 2019/0357968 on Nov. 28, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument comprising:
    (a) an end effector, wherein the end effector comprises:
        (i) a first jaw,
        (ii) a second jaw pivotably coupled with the first jaw, wherein the second jaw is operable to transition between an open position and a closed position,
        (iii) a knife configured to actuate between a pre-fired position to a fired position, and
        (iv) an electrode assembly configured to apply RF energy to tissue;
    (b) a handle assembly, wherein the handle assembly comprises:
        (i) a housing associated with the first jaw,
        (ii) an arm associated with the second jaw, wherein the arm is pivotably coupled with the housing, wherein the arm is configured to pivot the second jaw between the open position and the closed position;
    (c) a knife drive assembly configured to actuate the knife between the pre-fired position and the fired position;
    (d) an electrode activation assembly configured to activate the electrode assembly; and
    (e) a lockout assembly configured to transition between a locked configuration and an unlocked configuration, wherein the lockout assembly is configured to inhibit activation of the electrode assembly and inhibit actuation of the knife drive assembly while in the locked configuration, wherein the lockout assembly is configured to allow activation of the electrode assembly and allow actuation of the knife drive assembly while in the unlocked configuration, wherein the lockout assembly comprises a translating body resiliently biased toward the locked configuration, wherein the translating body comprises a lockout ledge configured to abut against a portion of the knife drive assembly in the locked configuration.

2. The surgical instrument of claim 1, wherein the arm comprises a resilient member configured to transition between a relaxed configuration and a flexed configuration while the second jaw is in the closed position.

3. The surgical instrument of claim 2, wherein the arm is configured to drive the lockout assembly into the unlocked configuration when the resilient member is in the flexed configuration.

4. The surgical instrument of claim 1, wherein the electrode activation assembly comprises an activation button and a lockout button, wherein the electrode activation assembly is configured to activate the electrode assembly only when both the activation button and the lockout button are activated.

5. The surgical instrument of claim 4, wherein the translating body of the lockout assembly is configured to activate the lockout button while in the unlocked configuration.

6. The surgical instrument of claim 5, wherein the electrode activation assembly comprises a sliding body configured to activate the activation button.

7. The surgical instrument of claim 6, wherein the sliding body is biased to not activate the activation button.

8. The surgical instrument of claim 5, wherein the electrode activation assembly comprises a circuit board.

9. The surgical instrument of claim 8, wherein the activation button is in communication with the circuit board.

10. The surgical instrument of claim 9, wherein the lockout button is in communication with the circuit board.

11. The surgical instrument of claim 9, wherein the lockout button acts as a switch for the activation button.

12. The surgical instrument of claim 1, wherein the knife drive assembly comprises a proximal presented surface configured to abut against the lockout ledge while the translating body is in the locked configuration and the knife is in the pre-fired position.

13. The surgical instrument of claim 1, wherein the translating body defines a through hole configured to receive a portion of the electrode activation assembly.

14. The surgical instrument of claim 13, wherein the through hole is configured to receive a portion of the knife drive assembly.

15. A surgical instrument comprising:
    (a) a housing extending distally into a first jaw;
    (b) an arm pivotably coupled with the housing, wherein the arm extends distally into a second jaw, wherein the arm is operable to drive the second jaw between an open position and a closed position, wherein the arm is operable to transition between a first position and a second position while the second jaw is in the closed position;
    (c) an electrode associated with the first jaw or the second jaw, wherein the electrode is configured to apply RF energy to tissue;
    (d) a knife configured to actuate within the first jaw and the second jaw between a pre-fired position and a fired position;
    (e) an electrode activation assembly configured to activate the electrode,
    (f) an indicator assembly comprising a button configured to generate a signal;
    (g) a knife actuation assembly configured to actuate the knife between the pre-fired position and the fired position; and
    (h) a lockout assembly comprising a lockout body configurated to actuate between an unlocked configuration and a locked configuration in response to the arm moving between the first position and the second position, respectively, wherein the lockout assembly is configured to inhibit actuation of the knife actuation assembly in the locked configuration, wherein the lockout body is configured to allow actuation of the knife actuation assembly and activate the button in the unlocked configuration.

16. The surgical instrument of claim 15, wherein the knife actuation assembly comprises a rotary gear and a link, wherein the rotary gear is pivotably coupled with the housing, wherein the link is pivotably coupled with the knife and the rotary gear.

17. The surgical instrument of claim 15, wherein the electrode activation assembly comprises an activation button, wherein the electrode activation assembly is configured to activate the electrode only if both the activation button is depressed and the indicator assembly has generated the signal.

18. A surgical instrument comprising:
(a) a housing extending distally into a first jaw;
(b) an arm pivotably coupled with the housing, wherein the arm extends distally into a second jaw, wherein the arm is operable to drive the second jaw between an open position and a closed position, wherein the arm is configured to transition between a relaxed state and a flexed state while the second jaw is in the closed position;
(c) an electrode associated with the first jaw or the second jaw, wherein the electrode is configured to apply RF energy to tissue;
(d) a knife configured to actuate within the first jaw and the second jaw between a pre-fired position and a fired position;
(e) an electrode activation assembly configured to activate the electrode, wherein the electrode activation assembly comprises a button in communication with the electrode;
(f) a knife actuation assembly configured to actuate the knife between the pre-fire position and the fired position; and
(g) a lockout assembly comprising a lockout body configured to actuate between a locked position and an unlocked position in response to the arm transitioning between the relaxed state and the flexed state, respectively, wherein the lockout body is configured to prevent actuation of the knife actuation assembly in the locked position, wherein the lockout body is configured to allow actuation of the knife actuation assembly and activate the button of the electrode activation assembly in the unlocked position.

19. The surgical instrument of claim 18, wherein the button, while activated by the lockout body, is configured to directly activate the electrode.

20. The surgical instrument of claim 18, wherein the electrode activate assembly comprises a trigger configured to activate the electrode, wherein the button is configured to inhibit the trigger from activating the electrode while the lockout body is in the locked position.

* * * * *